United States Patent
Haseba et al.

(12)

(10) Patent No.: US 6,235,355 B1
(45) Date of Patent: May 22, 2001

(54) DIOXANE DERIVATIVES, LIQUID-CRYSTAL COMPOSITIONS CONTAINING THE SAME, AND LIQUID-CRYSTAL DISPLAY DEVICES MADE BY USING THE SAME

(75) Inventors: Yasuhiro Haseba, Matsudo; Tomoyuki Kondou, Ichihara; Shuichi Matsui, Ichihara; Kazutoshi Miyazawa, Ichihara; Hiroyuki Takeuchi, Ichihara; Yasusuke Hisatsune, Ichihara; Fusayuki Takeshita, Kimitsu; Etsuo Nakagawa, Ichihara, all of (JP)

(73) Assignee: Chisso Corporation, Osaka (JP)

( * ) Notice: Subject to any disclaimer, the term of this patent is extended or adjusted under 35 U.S.C. 154(b) by 0 days.

(21) Appl. No.: 09/101,999

(22) PCT Filed: Jun. 30, 1997

(86) PCT No.: PCT/JP97/02257

§ 371 Date: Jul. 21, 1998

§ 102(e) Date: Jul. 21, 1998

(87) PCT Pub. No.: WO98/17664

PCT Pub. Date: Apr. 30, 1998

(30) Foreign Application Priority Data

Oct. 22, 1996 (JP) .................................................. 8-297984

(51) Int. Cl.$^7$ .......................... C09K 19/34; C09K 19/42; C07D 319/06
(52) U.S. Cl. ................ 428/1.1; 252/299.61; 252/299.63; 549/369
(58) Field of Search .......................... 252/299.61, 299.63; 428/1.1; 549/369; 570/129, 131

(56) References Cited

U.S. PATENT DOCUMENTS

| | | | |
|---|---|---|---|
| 5,250,220 | * 10/1993 | Wachtler et al. | 252/299.61 |
| 5,254,698 | * 10/1993 | Coates et al. | 549/369 |
| 5,322,638 | * 6/1994 | Schdat et al. | 252/299.61 |
| 5,478,497 | * 12/1995 | Buchecker et al. | 252/299.61 |
| 5,667,721 | * 9/1997 | Buchecker et al. | 252/299.61 |
| 5,800,735 | * 9/1998 | Poetsch et al. | 252/299.61 |

* cited by examiner

*Primary Examiner*—Shean C. Wu
(74) *Attorney, Agent, or Firm*—Wenderoth, Lind & Ponack, L.L.P.

(57) ABSTRACT

The present invention provides liquid crystalline compounds having a high voltage holding ratio and a remarkably high $\Delta\epsilon$ value, electric and chemical stability, and having good compatibility with known liquid crystalline compounds, liquid crystal compositions containing the compound, and liquid crystal display devices constituted by using the compounds.

The liquid crystalline compounds of the present invention are particular dioxane derivatives represented by general formula (1). Further, the present invention relates to liquid crystal compositions characterized in that the compositions comprise at least one of the derivatives, and liquid crystal display devices constituted by using the compositions.

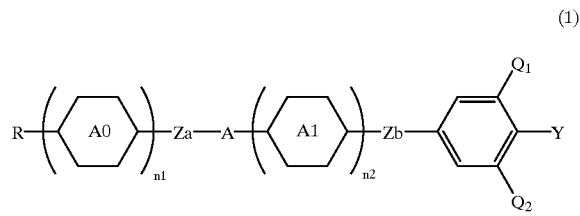

(1)

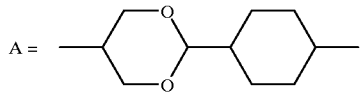

(a)

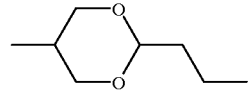

(b)

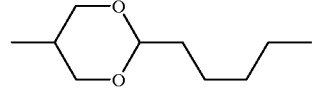

(c)

21 Claims, No Drawings

DIOXANE DERIVATIVES, LIQUID-CRYSTAL COMPOSITIONS CONTAINING THE SAME, AND LIQUID-CRYSTAL DISPLAY DEVICES MADE BY USING THE SAME

This application is a 371 of PCT/SP 97/02257, filed Jun. 30, 1997.

BACKGROUND OF THE INVENTION

1. Field of the Invention

The present invention relates to liquid crystalline compounds effective as components of liquid crystal compositions, particularly, dioxane derivatives preferably used as liquid crystal compositions for TFT, liquid crystal compositions containing them, and liquid crystal display devices constituted by using these derivatives.

2. Description of the Prior Art

Liquid crystal display devices are obtained by using liquid crystal materials having properties of optical anisotropy and dielectric anisotropy. The display modes are twist nematic (TN) mode, dinamic scattering (DS) mode, guest-host (G.H) mode, deformation of aligned phases (DAP) mode, super twist nematic (STN) mode and the like. The properties of liquid crystal materials are different in each mode. Lately, in particular, liquid crystal devices having high display quality are demanded. In response to the demand, a display device of an active matrix mode represented by a thin film transistor (TFT) mode have been used increasingly.

The liquid crystalline compounds used for any display devices should be stable to moisture, air, heat, light and the like. These compounds also should have a liquid crystal phase over a wide range of temperatures around room temperature, and have low viscosity, good compatibility to the other liquid crystalline compounds and liquid crystal compositions, a high dielectric anisotropy value ($\Delta\epsilon$), and proper optical anisotropy ($\Delta n$). These compounds should be stable chemically and electrically. Particularly, the display device of the active matrix mode represented by the TFT mode requires a high voltage holding ratio. However, there are no materials satisfying these conditions, so that liquid crystal compositions, which are obtained by mixing several kinds of liquid crystalline compounds or liquid crystalline compounds, are used under existing circumstances.

Lately, low voltage driving is demanded to the liquid crystal device of the TFT mode. In response to the demand, liquid crystalline compounds and liquid crystal compositions, which have $\Delta\epsilon$ higher than that of the liquid crystal materials used for conventional liquid crystal display devices of the TFT mode, are required. As a result, liquid crystal materials having a high voltage holding ratio and high $\Delta\epsilon$ are actively developed. Hitherto, it has been generally known that liquid crystal materials of fluorine types show a high voltage holding ratio, and Japanese Patent Publication No. 01-04496 discloses the following compound (10).

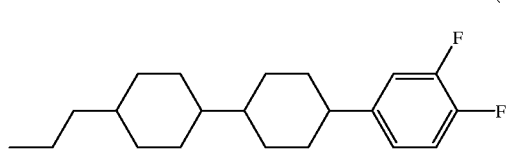

(10)

Since the above compound (10) has a voltage holding ratio higher than that of a liquid crystalline compound having a cyano group, it is mainly used as a component of the liquid crystal composition for TFT. However, extrapolated $\Delta\epsilon$ of compound (10) (extrapolated $\Delta\epsilon$ means that it is calculated from the value of $\Delta\epsilon$ of the composition, dissolving the compounds in a mother liquid crystal having a nematic phase, the value of $\Delta\epsilon$ of the mother liquid crystal and the mixture ratio, and the $\Delta\epsilon$ described hereinafter shows the extrapolated $\Delta\epsilon$) is small as 8.5. The compound can not be used as liquid crystal materials for low voltage driving, which is represented by 2.5 V driving and demanded in practice.

As a compound having $\Delta\epsilon$ higher than that of compound (10), Japanese Patent Laid-Open Publication No. 02-233626 discloses the trifluorophenyl compound (11) represented by the following formula:

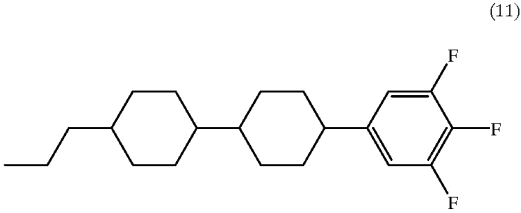

(11)

Although $\Delta\epsilon$ of compound (11) is 11.0 and higher than that of compound (10), the value is still too small to satisfy the demand of lower voltage like the above described value.

Japanese Patent Laid-Open Publication No. 04-506361 discloses trifluoromethylphenyl derivative (12) and trifluoromethoxyphenyl derivative (13).

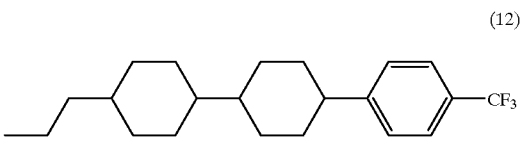

(12)

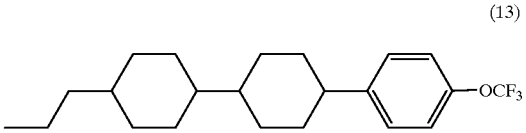

(13)

However, $\Delta\epsilon$ of these compounds can not satisfy the demand of lower voltage in the market like compounds (10) and (11). (For example, $\Delta\epsilon$ of compound (13) is about 5 (IDY (Televigakugihou) 95).

As a compound having higher $\Delta\epsilon$, Japanese Patent Laid-Open Publication No. 02-233626 discloses a dioxane derivative represented by the following formula (14):

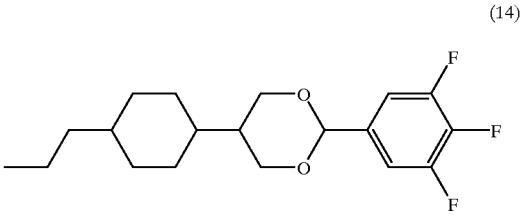

(14)

Although $\Delta\epsilon$ of the compound is high 15.7, it is impossible to lower the driving voltage into a necessary level. Moreover, the voltage holding ratio is smaller than that of liquid crystalline compounds of fluoric types not having a dioxane ring, so that the compound can not be contained in the materials for a liquid crystal display devices demanding higher voltage holding ratio As an example, the voltage holding ratio of compound (11) is 98% at a temperature of 25° C. and 96% at 100° C., while that of compound (14) is 98% at 25° C. and 92% at 100° C.

Accordingly, liquid crystalline compounds and liquid crystalline compounds having both higher Δε and higher voltage ratio have been desired eagerly.

The inventors of the present invention has studied earnestly to find a liquid crystalline compound most suitable for liquid crystal materials for the TFT low voltage driving represented by 2.5V driving, and they have found that the liquid crystalline compound, in which a Sp3 carbon is bound to the 2-position of a 1,3-dioxane-2,5-diyl group, and the molecular end has an electron-attracting group of a fluorine or chlorine type, has specifically high Δε and high voltage holding ratio.

DISCLOSURE OF INVENTION

The object of the present invention is to provide a liquid crystalline compound having a remarkably high Δε value and high voltage holding ratio, and having good compatibility with known liquid crystalline compounds, a liquid crystal composition containing the compound, and liquid crystal display device constituted by using the compound.

The present inventors have earnestly studied to accomplish the object, and have found the present invention. Namely, the present invention is as follows:

(1) A dioxane derivative represented by general formula (1):

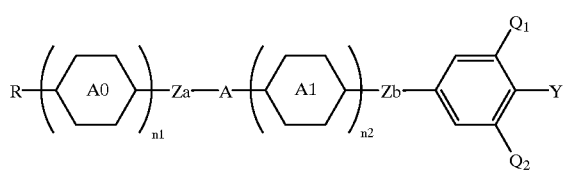

(1)

wherein R represents an alkyl group of 1–20 carbon atoms or a hydrogen atom,
n1 and n2, each independently, are an integer of 0–2, n1+n2 ≦2,
$Q_1$ and $Q_2$, each independently, are a hydrogen atom, fluorine atom or chlorine atom,
A represents (a), (b) or (c),

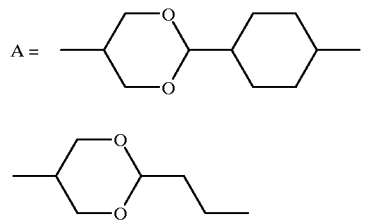

(a)

(b)

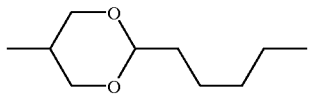

(c)

ring A0 and A1 represent a 1,4-cyclohexylene group or a 1,4-phenylene group, in which 1 or more hydrogen atoms may be replaced by a fluorine atom or a chlorine atom, and one or two carbon atoms may be replaced by a silicon atom in the 1,4-cyclohexylene in A, ring A0 and ring A1, Za and Zb, each independently, represent a single bond, —CH$_2$CH$_2$—, —CH$_2$CH$_2$CH$_2$CH$_2$—, OCH$_2$, —CH$_2$O—, COO— or —CF$_2$O—, Y represents a hydrogen atom, a halogen atom, or a halogenated alkyl group of 1–5 carbon atoms, in which one or more not-adjacent methylene groups may be replaced by an oxygen atom or a sulfur group, in the case of n1=0 and n2=1, and A is (b) and ring A1 is 1,4-phenylene, and Za and Zb are a single bond, or in the case of n1=n2=0 and A is (a) and Zb is a single bond, at least one of Q1 and Q2 represents a fluorine atom or a chlorine atom; in the case of Y is a fluorine atom or a chlorine atom, Q1 and Q2, each independently, represent a fluorine atom or a chlorine atom.

Further, each element constituting the compound may be replaced by its isotope.

(2) A dioxane derivative according to (1), wherein n1=n2=0, Za is a single bond, and A=(b).

(3) A dioxane derivative according to (1), wherein n1=n2=0, Za is a single bond, and A=(a).

(4) A dioxane derivative according to (1), wherein n1+n2=1, and A=(b).

(5) A dioxane derivative according to (1), wherein n1+n2=1, and A=(a).

(6) A dioxane derivative according to (1), wherein n1+n2=2, and A=(b).

(7) A dioxane derivative according to (1), wherein in the case of A=(c), or Zb is —CH$_2$CH$_2$CH$_2$CH$_2$—, or n1 is not 0, Za is —CH$_2$CH$_2$CH$_2$CH$_2$—.

(8) A dioxane derivative according to (1), wherein Q1 and Q2 both are a fluorine atom.

(9) A liquid crystal composition comprising at least one dioxane derivative according to any one of (1) to (8).

(10) A liquid crystal composition comprising at least one dioxane derivative according to any one of (1) to (8) as the first component, and at least one compound selected from the compound group comprising compounds represented by general formulas (2), (3) and (4) as the second component,

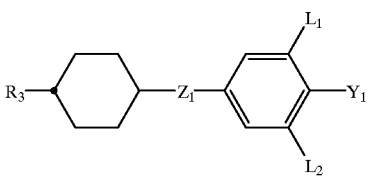

(2)

-continued (3)

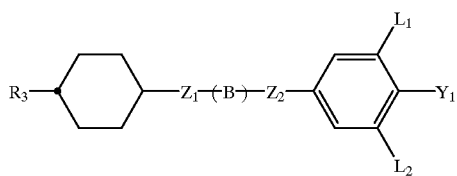

(4)

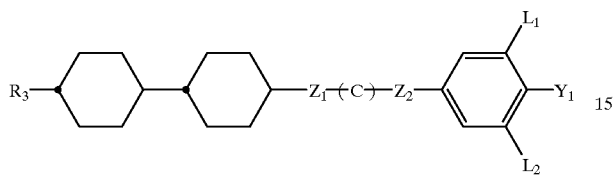

wherein $R_3$ is an alkyl group of 1–10 carbon atoms, in the alkyl group, at least one not-adjacent methylene group may be replaced by an oxygen atom or —CH=CH—, and any hydrogen atom may be replaced by a fluorine atom, $Y_1$ represents a fluorine atom, a chlorine atom, $OCF_3$, $OCF_2H$, $CF_3$, $CF_2H$, $CFH_2$, $OCF_2CF_2H$ or $OCF_2CFHCF_3$, $L_1$ and $L_2$, each independently, represent a hydrogen atom or a fluorine atom, $Z_1$ and $Z_2$, each independently, —$CH_2CH_2$—, —$CH_2CH_2CH_2CH_2$—, —COO—, —$CF_2O$—, —$OCF_2$—, —CH=CH— or a single bond, ring B represents trans-1,4-cyclohexylene, 1,3-dioxane-2,5-diyl or 1,4-phenylene, wherein the hydrogen atom may be replaced by a fluorine atom, ring C represents trans-1,4-cyclohexylene or 1,4-phenylene, wherein the hydrogen atom may be replaced by a fluorine atom, and each element constituting the compound in each formula may be replaced by its isotope.

(11) A liquid crystal composition comprising at least one dioxane derivative according to any one of (1) to (8) as the first component, and at least one compound selected from the compound group comprising compounds represented by general formulas (5) and (6) as the second component, (5)

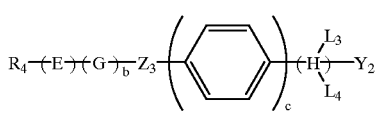

(6)

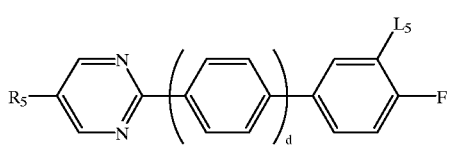

wherein $R_4$ and $R_5$, each independently, represent an alkyl group of 1–10 carbon atoms, in the alkyl group, one or more not-adjacent methylene groups may be replaced by an oxygen atom or —CH=CH—, and any hydrogen atom may be replaced by a fluorine atom, $Y_2$ represents —CN or —C≡C—CN, ring E represents trans-1,4-cyclohexylene, 1,4-phenylene, 1,3-dioxane-2,5-diyl or pyrimidine-2,5-diyl, ring G represents trans-1,4-cyclohexylene, pyrimidine-2,5-diyl, or 1,4-phenylene, wherein the hydrogen atom may be replaced by a fluorine atom, ring H represents trans-1,4-cyclohexylene or 1,4-phenylene, $Z_3$ represents —$CH_2CH_2$—, —COO— or a single bond, $L_3$, $L_4$ and $L_5$, each independently, represent a hydrogen atom or a fluorine atom, b, c and d, each independently, are 0 or 1, and each element constituting the compound in each formula may be replaced by its isotope.

(12) A liquid crystal composition comprising at least one dioxane derivative according to any one of (1) to (8) as the first component, and at least one compound selected from the compound group comprising compounds represented by the said general formulas (2), (3) and (4) as the second component, and at least one compound selected from the compound group comprising compounds represented by general formulas (7), (8) and (9) as the third component, (7)

(8)

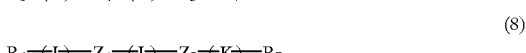

(9)

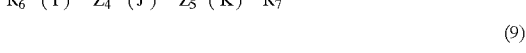

wherein $R_6$ and $R_7$, each independently, represent an alkyl group of 1–10 carbon atoms, in the alkyl group, one or more not-adjacent methylene groups may be replaced by an oxygen atom or —CH=CH—, and any hydrogen atom may be replaced by a fluorine atom, I, J and K, each independently, represent trans-1,4-cyclohexylene, pyrimidine-2,5-diyl or 1,4-phenylene, wherein the hydrogen atom may be replaced by a fluorine atom, $Z_4$ and $Z_5$, each independently, represent —C≡C—, —COO—, —$CH_2C_2$—, —CH=CH— or a single bond, and each element constituting the compound in each formula may be replaced by its isotope

(13) A liquid crystal composition comprising at least one dioxane derivative according to any one of (1) to (8) as the first component, and at least one compound selected from the compound group comprising compounds represented by the said general formulas (5) and (6) as the second component, and at least one compound selected from the compound group comprising compounds represented by the said general formulas (7), (8) and (9) as the third component.

(14) A liquid crystal composition comprising at least one dioxane derivative according to any one of (1) to (8) as the first component, and at least one compound selected from the compound group comprising compounds represented by the said general formulas (2), (3) and (4) as a part of the second component, and at least one compound selected from the compound group comprising compounds represented by the said general formulas (5) and (6) as another part of the second component, and at least one compound selected from the compound group comprising compounds represented by the said general formulas (7), (8) and (9) as the third component.

(15) A liquid crystal composition according to any one of (9) to (14), wherein the liquid crystal composition further contains an optical active compound.

(16) A liquid crystal device constituted by a using liquid crystal composition according to any one of (9) to (14).

(17) A liquid crystal display device constituted by using the liquid crystal composition according to (15).

The compound represented by general formula (1) is a liquid crystalline compound having 3 rings to 5 rings including a dioxane ring, 2-position of the dioxane ring is bound to the Sp3 carbon, and the compound has a fluorine or chlorine electrophilic group at the molecular end. By such constitution, the compound has high voltage holding ratio and specifically high Δε.

For example, although compound (No. 21) of the present invention has the same alkyl chain and substituent group of the end benzene ring as those of compound (14), the former has specifically high Δε and high voltage holding ratio as described below. The Δε of compound (14) is 15.7, while the Δε of compound (No. 21) of the present invention is 23.7. The voltage holding ratio of compound (14) is 98% at 25° C. and 92% at 100° C., while that of compound (No. 21) is 98% at 25° C. and 94% at 100° C.

Considering the dipole of each part constitution of the molecule and the angle formed between the dipole and the main axe of moment of inertia, an ordinary person skill in the art may expect that compound (14) and compound (No. 21) of the present invention have the same degree of Δε. However, the Δε of compound (No. 21) of the present invention is 50% higher than that of compound (14). The fact is unexpected surprising characteristics.

Moreover, the following is an example of the compound of the present invention having specifically high Δε.

For example, the Δε of compound (11) is 11.0, while the Δε of compounds (15) and (16) having ethylene as a bonding group are 9.7 which is generally less than the former.

(15)

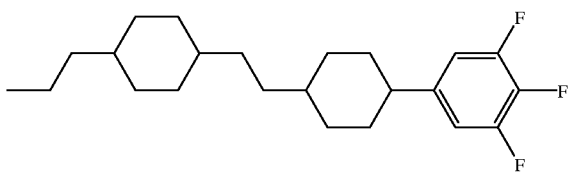

(16)

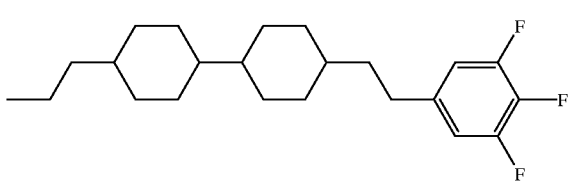

Compound (No. 98) of the present invention is obtained by introducing an ethylene group as a bonding group to 2-position of the dioxane ring of compound (17). The Δε of compound (17) is 25.7, while that of compound (No. 98) is 28.3 higher than that of compound (17) surprisingly.

(17)

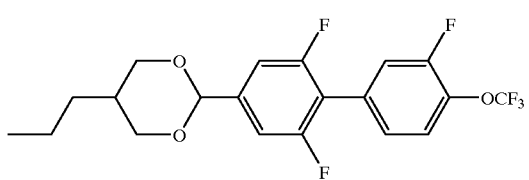

Such effects are shown only by the liquid crystalline compound having Sp3 carbon bound to 2-position of the dioxane ring and an electrophilic group of a fluorine or chlorine at the molecular end. Hitherto, the liquid crystalline compounds having a dioxane ring as shown in the following are disclosed in Japanese Patent Laid-Open Publication Nos. 4-503678 and 4-501272.

(18)

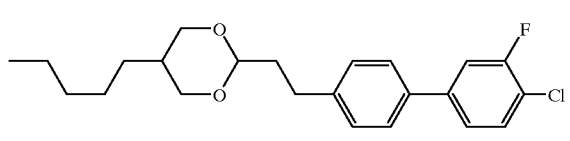

(19)

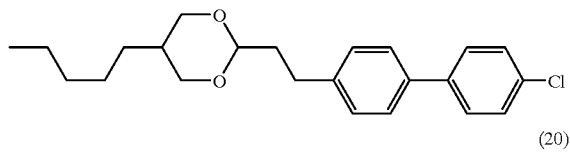

(20)

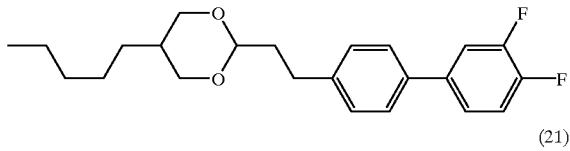

(21)

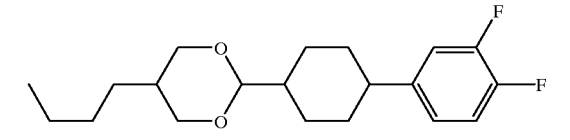

(22)

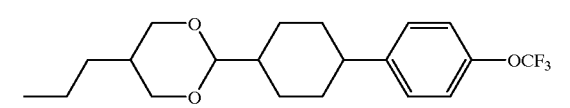

From a form, the compound of the present invention is included in a part of the said prior arts However, the description of the compound of the present invention is not practically found in the specification of these prior arts. Further, there is no description that the above-mentioned excellent properties, namely, specifically high Δε and high voltage holding ratio can be foreknown, and the physical values of the said compounds are not shown.

US005494606A describes about the dioxane derivative replaced by a halogen atom at the end of an alkyl group, but excellent properties of the compound of the present invention can not be foreknown.

The compound represented by general formula (1), which has a Sp3 carbon bound to 2-position of the dioxane ring and a fulorine or chlorine electrophilic group at the molecular end, has a high voltage holding ratio and specifically high Δε. The liquid crystal composition prepared by using the compound represented by general formula (1) of the present invention has high Δε and high voltage holding ratio, and it is useful for lowering the driving voltage of the liquid crystal display device of the TFT type.

It has been mentioned that the compounds of the present invention represented by general formula (1) show a high voltage holding ratio and a specifically high Δε, and the compounds of the present invention are described in detail in the following. Although the compound replaced the element constituting the compound by the isotope is not described in the following, such a compound has the same properties as those of the following compounds.

R represents an alkyl group of 1–20 carbon atoms or a hydrogen atom, and the alkyl group of preferably 1–7 carbon atoms, more preferably 2–5 carbon atoms, is balanced between the viscosity and the temperature region of the liquid crystal phase, more preferably, 2–5 carbon atoms.

Bonding groups Za and Zb, each independently, is a single bond, —CH$_2$CH$_2$—, —CH$_2$CH$_2$CH$_2$CH$_2$—, —CH₂O—, —OCH₂—, —COO— or —CF₂O—, and the following shows each characteristic.

The compound, whose bonding groups Za and Zb are both single bonds, shows a relative high transpalent point, low viscosity, good compatibility to other liquid crystalline compounds or liquid crystal compositions, and chemical and electrical stability. When one of bonding groups Za and Zb is a single bond, and the other bond is —CH₂CH₂—, in comparison with the compound having single bonds, the compound shows less viscosity and better compatibility. When at least one of bonding groups Za and Zb is —CH₂CH₂CH₂CH₂—, in comparison with the compound having a single bond and —CH₂CH₂, the compound shows less viscosity and better compatibility. When at least one of bonding groups Za and Zb is —COO—, in comparison with the compounds having the said 5 kinds of other bonding groups, the compound shows less chemical and physical stability and higher Δε. When at least one of bonding groups Za and Zb is —CF₂O—, the compound shows low viscosity and better chemical and physical stability.

Preferable constitution of end-substituting group Y and characteristics of the compound having the group are then shown. When Y is fluorine, the compound has relative high Δε and low viscosity, and good compatibility with the other liquid crystalline compounds or liquid crystal compositions When Y is CF₃, the compound shows high Δε. When Y is OCF₃, or OCF₂H, the compound shows low viscosity. When Y is Cl, —OCF₂CF₂H, or —OCF₂CFHCF₃, the compound has high Δn and a high clearing point. When Y is —OCH₂CF₂H, —OCH₂CF₃ or —OCFHCF₃, the compound has a high clearing point, and relative low viscosity. These substituting groups each have the said characteristics, and very useful. Further, as the other substituting groups, Y is preferably —CF₂H, —CF₂Cl, —CH₂CF₃, —CH₂CH₂F, —CH₂CH₂CH₂F, —CH₂CH₂CH₂CH₂F, —OCFH₂, —OCF₂Cl, —OCF₂CF₃, or —OCF₂CF₂CF₃.

The compound of the present invention may have fluorine or chlorine-replaced phenylene groups. The compound having more fluorine or chlorine-replaced groups at lateral positions of the phenylene group has higher Δε. On the other hand, the compound having less-replaced groups has a higher clearing point and lower viscosity.

The compounds of the present invention having 1-sila-1,4-cyclohexylene group and 4-sila-1,4-cyclohexylene group are better compatibility with the other liquid crystalline compounds and liquid crystal compositions at a low temperature than that of the compound having 1,4-cyclohexylene group.

The compounds of the present invention have high voltage holding ratio, and have the characteristics aforesaid. Moreover, the compounds represented by general formulas (1-A)-(1-S) have more preferable characteristics.

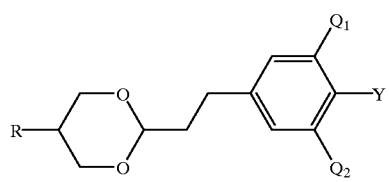

(1-A)

(1-B)

(1-C)

(1-D)

(1-E)

(1-F)

(1-G)

(1-H)

(1-I)

(1-J)
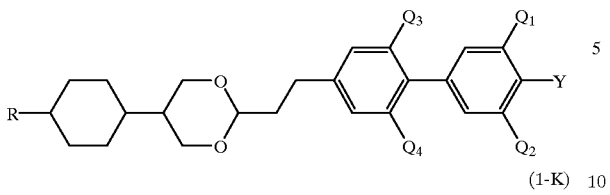

(1-K)
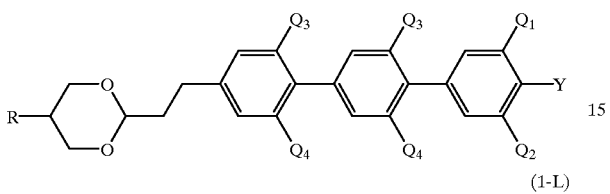

(1-L)
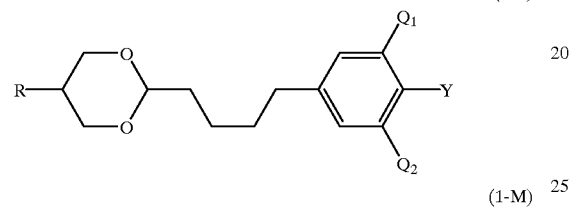

(1-M)
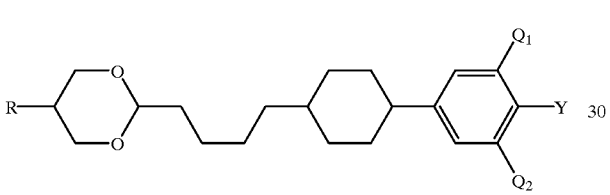

(1-N)
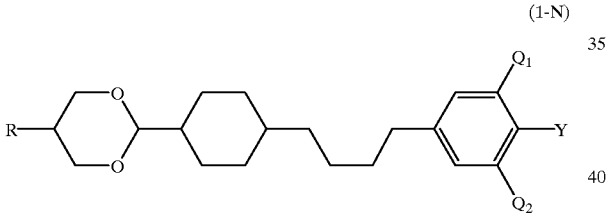

(1-O)
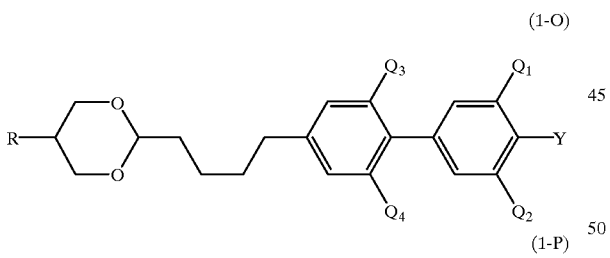

(1-P)
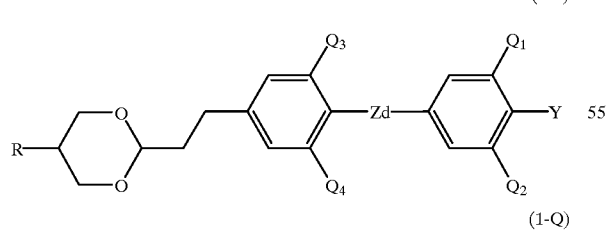

(1-Q)
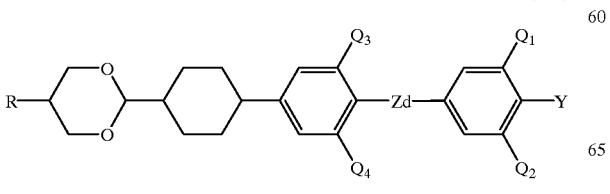

(1-R)
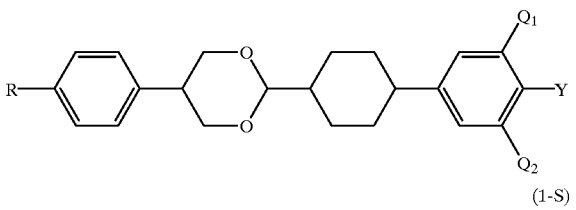

(1-S)
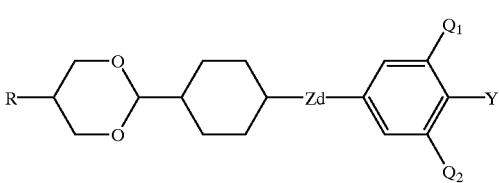

The compound represented by formula (1-A), is that, in general formula (1), n1 and n2 both are 0, Za and Zb both are a single bond, A is (b).

The compound represented by formula (1-B), is that, in general formula (1), n1 and n2 both are 0, Za and Zb both are a single bond, A is (a).

The compound represented by formula (1-C), is that, in general formula (1), n1 is 0, n2 is 1, ring A1 is 1,4-cyclohexylene, Za and Zb both are a single bond, and A is (b)

The compound represented by formula (1-D), is that, in general formula (1), n1 and n2 both are 0, Za is a single bond, Zb is —$CH_2CH_2$—, A is (a).

The compound represented by formula (1-E), is that, in general formula (1), n1 is 0, n2 is 1, ring A1 is replaced or not replaced 1,4-phenylene, Za and Zb both are a single bond, and A is (b).

The compound represented by formula (1-F), wherein $Zc_2$ is a single bond, is that, in general formula (1), n1 is 0, n2 is 1, ring A1 is 1,4-cyclohexylene, Za is a single bond, and A is (a).

The compound represented by formula (1-F), wherein $Zc_2$ is —$CH_2CH_2$—, is that, in general formula (1), n1 is 0, n2 is 2, ring A1 is 1,4-cyclohexylene, Za is a single bond, and A is (b).

The compound represented by formula (1-G), wherein $Zc_2$ is a single bond, is that, in general formula (1), n1 is 1, n2 is 0, ring A0 is 1,4-cyclohexylene, and A is (a).

The compound represented by formula (1-G), wherein $Zc_2$ is —$CH_2CH_2$—, is that, in general formula (1), n1 and n2 both are 1, ring A0 and A1 both are 1,4-cyclohexylene, and A is (b).

The compound represented by formula (1-H), is that, in general formula (1), n1 is 2, n2 is 0, ring A0 is 1,4-cyclohexylene, Za and Zb both are a single bond, and A is (b).

The compound represented by formula (1-I), is that, in general formula (1), n1 is 0, n2 is 1, ring A1 is replaced or not replaced 1,4-phenylene, Za and Zb both are a single bond, and A is (a).

The compound represented by formula (1-J), is that, in general formula (1), n1 and n2 both are 1, ring A0 is 1,4-phenylene, ring A1 is replaced or not replaced 1,4-phenylene, Za and Zb both are a single bond, and A is (b).

The compound represented by formula (1-K), is that, in general formula (1), n1 is 0, n2 is 2, ring A1 is replaced or not replaced 1,4-phenylene, Za and Zb both are a single bond, and A is (b).

The compound represented by formula (1-L), is that, in general formula (1), n1 and n2 both are 0, Za and Zb both are a single bond, and A is (c).

The compound represented by formula (1-M), is that, in general formula (1), n1 is 0, n2 is 1, ring A1 is 1,4-cyclohexylene, Za and Zb both are a single bond, and A is (c).

The compound represented by formula (1-N), is that, in general formula (1), n1 and n2 both are 0, Za is a single bond, Zb is —CH$_2$CH$_2$CH$_2$CH$_2$—, and A is (a).

The compound represented by formula (1-O), is that, in general formula (1), n1 is 0, n2 is 1, ring A1 is replaced or not replaced 1,4-phenylene, Za and Zb both are a single bond, and A is (c).

The compound represented by formula (1-P), is that, in general formula (1), n1 is 0, n2 is 1, ring A1 is replaced or not replaced 1,4-phenylene, Za is a single bond, Zb is —COO— or —CF$_2$O—, and A is (b).

The compound represented by formula (1-Q), is that, in general formula (1), n1 is 0, n2 is 1, ring A1 is replaced or not replaced 1,4-phenylene, Za is a single bond, Zb is —COO— or —CF$_2$O, and A is (a).

The compound represented by formula (1-R), is that, in general formula (1), n1 is 1, n2 is 0, ring A0 is replaced or not replaced 1,4-phenylene, Za and Zb both are a single bond, and A is (a).

The compound represented by formula (1-S), is that, in general formula (1), n1 and n2 both are 0, Za is a single bond, Zb is —COO— or CF$_2$O, A is (a).

However, R, Q$_1$, Q$_2$ and Y show the same meaning as described above, Q3 and Q4, each independently, represent a hydrogen atom or a fluorine atom, Zc$_1$–Zc$_3$ each represent single bond or —CH$_2$CH$_2$—, Zd represents —CF$_2$O— or —COO—.

Preferable compounds represented by general formulas (1-A)–(1-S) have the following characteristics. Generally speaking, the voltage holding ratio of the compounds represented by general formula (1-O), (1-P) and (1-S), wherein Zd is —COO—, is less than that of the other compounds of the present invention, but it is higher than that of conventional compounds having a benzene ring connected to 2-position of a dioxane ring and having —COO—. The other compound of the present invention all similarly have high voltage holding ratio. The compounds of the present invention can be driven at low voltage because these compounds have specifically high Δε.

Characteristics exclusive of those of voltage holding ratio and Δε are described in the following.

The compound represented by general formula (1-A) has very low viscosity and very good compatibility. The compound is useful to liquid crystal materials for rapid response and components constituting liquid crystal materials which can display at a low temperature.

The compound represented by general formula (1-B) has a high clearing point and low viscosity.

The compound represented by general formula (1-C) and (1-D) has a relatively high clearing point and good compatibility.

The compounds represented by general formulas (1-B)–(l-D) are well balanced in a high clearing point, viscosity and compatibility.

The compound represented by general formula (1-E) has relatively low viscosity and high Δn. By using the compound, it becomes possible to easily control the An value of a liquid crystal composition to a desired value and drive at low voltage.

Since the compounds represented by formulas (1-F)–(1-H) have a very high clearing point, these are useful for components constituting liquid crystal materials, which are able to display at a high temperature.

The compounds represented by general formulas (1-I)–(1-K) and (1R) have a high clearing point and high An. Particularly, An of (1-K) is very high. These compounds also are useful for components constituting liquid crystal materials, which are able to display at a high temperature.

The compounds represented by general formula (1-L)–(1-O) each having a bonding group of —CH$_2$CH$_2$CH$_2$CH$_2$—, have good compatibility.

The compounds represented by general formulas (1-P), (1-Q) and (1-S), wherein Zd is —COO—, have high clearing point and the compounds, wherein Zd is —CF$_2$O—, have low viscosity.

Conventional compounds do not have such high voltage holding ratio and high Δε.

The compounds of the present invention have the said merits, it allows to drive at low voltage in the liquid crystal display elements that require particular high voltage holding ratio.

The compounds of the present invention are preferably used for liquid crystal compositions for TFT, and they are used for various other purposes. For example, there are liquid crystal compositions for TN, a guest-host mode, a liquid crystal display element of a polymer dispersion type, a dynamic scattering mode and STN, ferroelectric liquid crystal compositions, anti-ferroelectric liquid crystal compositions, and liquid crystal compositions for inplane switching, an OCB mode and a R-OCB mode.

The term of liquid crystalline compound in the present invention means a compound having a liquid crystal phase and non-liquid crystalline compound which gives no damage to liquid crystal phase by mixing with the other liquid crystals.

The liquid crystal compositions of the present invention, which have one or more compounds represented by general formula (1) of 0.1–99.9% by weight, preferably 1–50% by weight and more preferably 3–20% by weight, are preferred to develop good characteristics.

The liquid crystal compositions provided in the present invention are obtained by adding the first component containing at least one compound represented by general formula (1), and mixing the compound selected from the compound group represented by general formulas (2)–(9) according to the object.

As the compounds represented by general formulas (2)–(4), the following compounds are preferably exemplified (R$_3$ and Y$_1$ show the same meaning as described above).

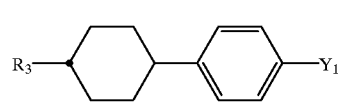

(2-1)

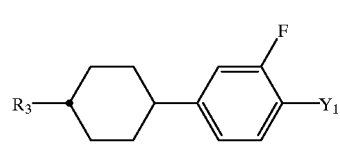

(2-2)

-continued
(2-3)
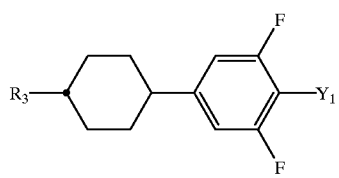
(2-4)
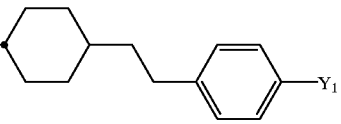
(2-5)
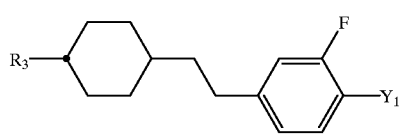
(2-6)
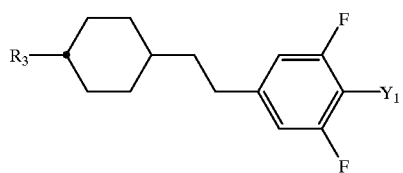
(2-7)
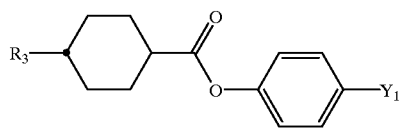
(2-8)
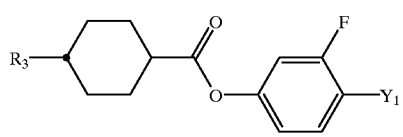
(2-9)
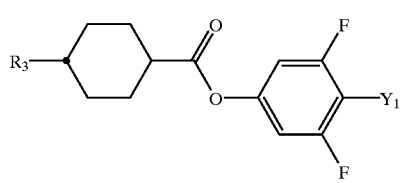
(3-1)
(3-2)
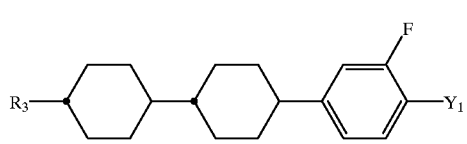
-continued
(3-3)
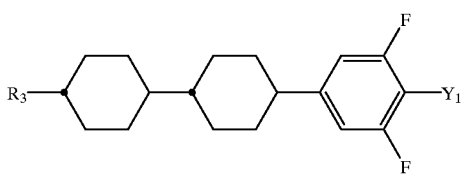
(3-4)
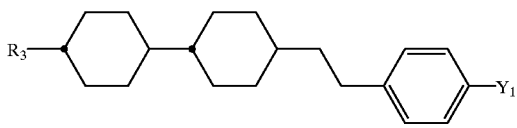
(3-5)
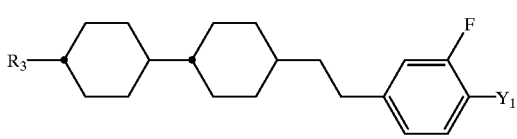
(3-6)
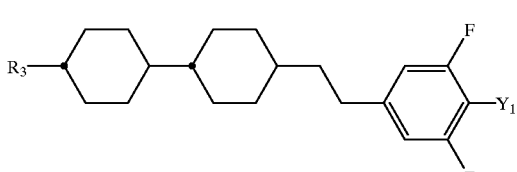
(3-7)
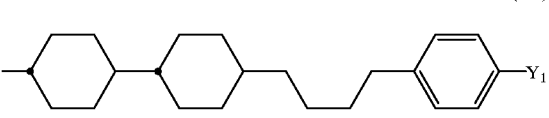
(3-8)
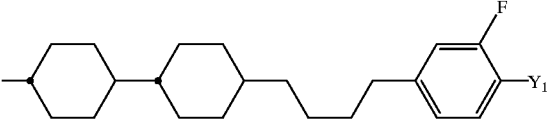
(3-9)
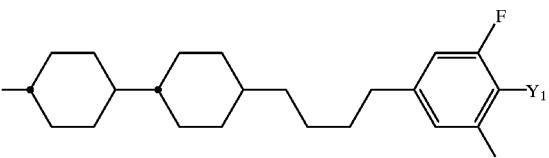
(3-10)
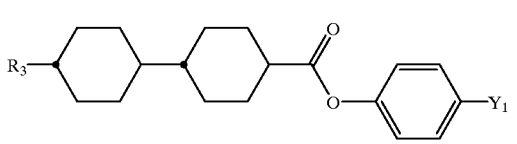
(3-11)
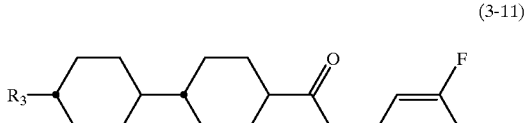

(3-12) 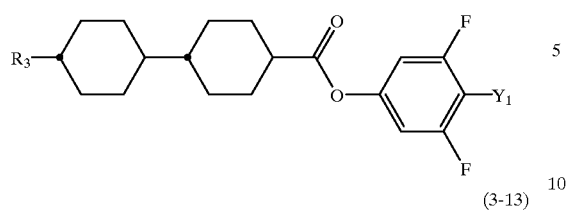
(3-13) 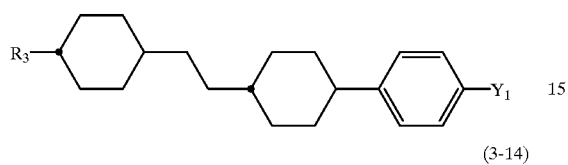
(3-14) 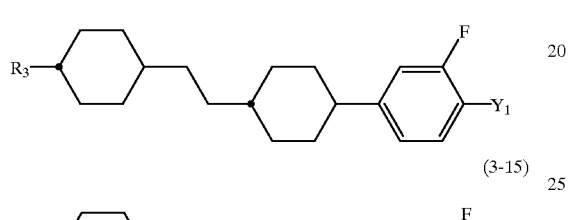
(3-15) 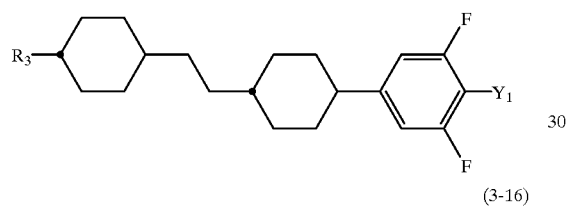
(3-16) 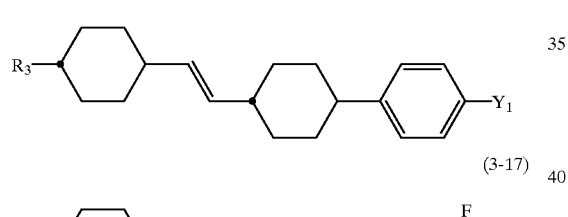
(3-17) 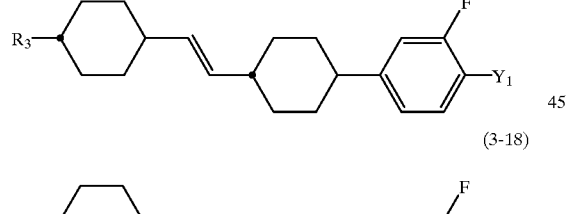
(3-18) 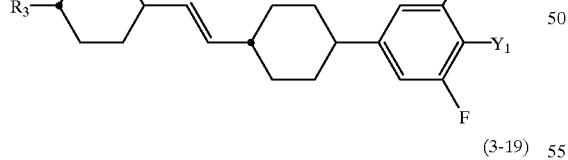
(3-19) 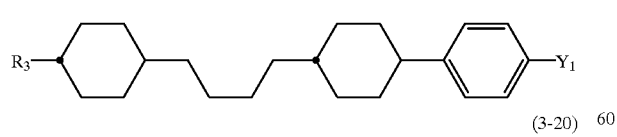
(3-20) 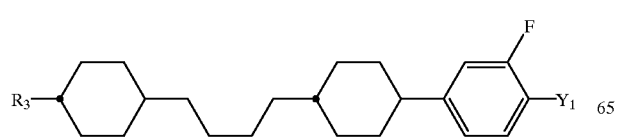
(3-21) 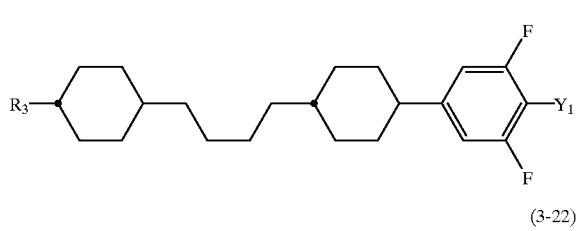
(3-22) 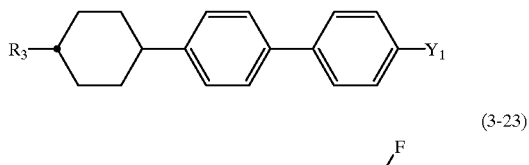
(3-23) 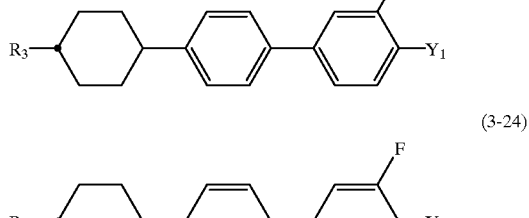
(3-24) 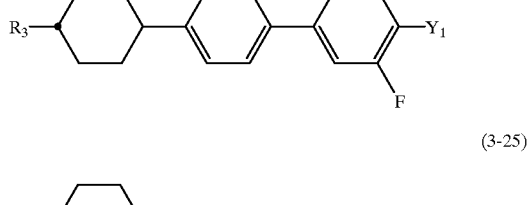
(3-25) 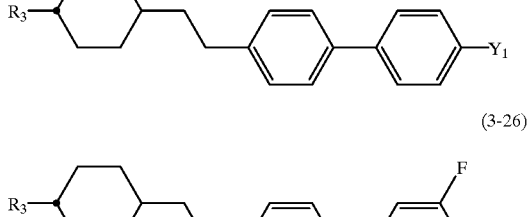
(3-26) 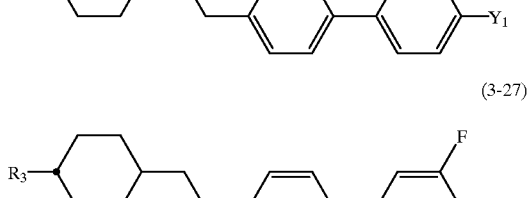
(3-27) 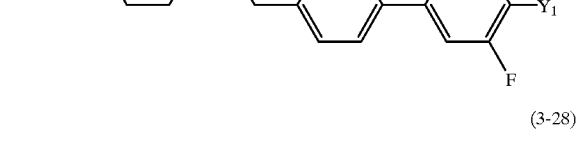
(3-28) 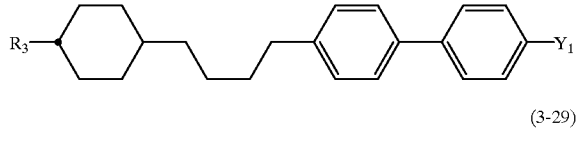
(3-29) 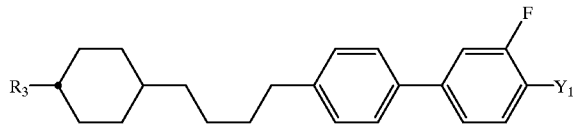

-continued
(3-30)
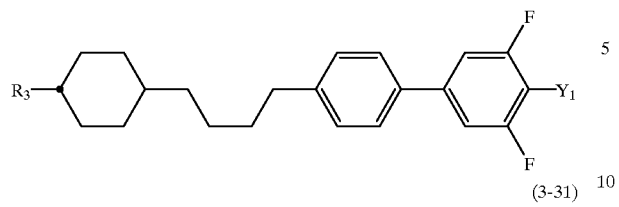
(3-31)
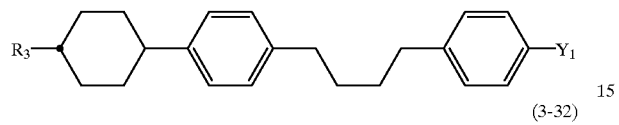
(3-32)
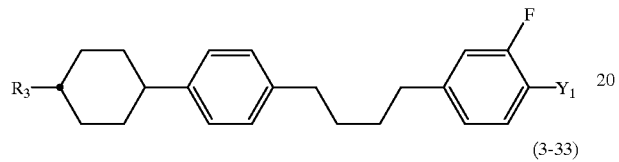
(3-33)
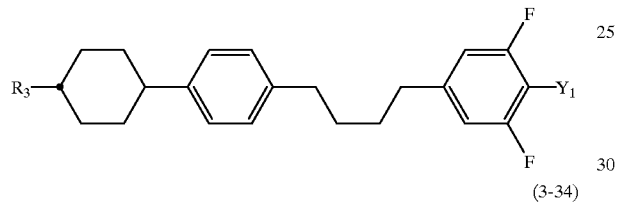
(3-34)
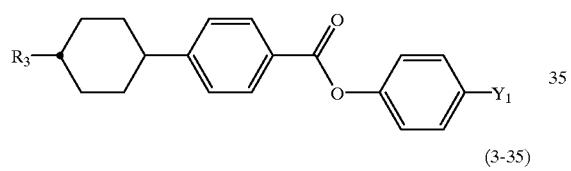
(3-35)
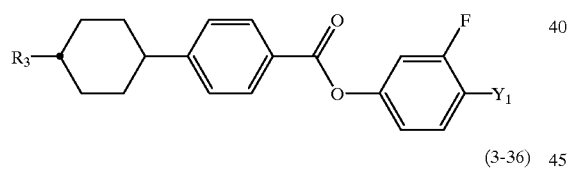
(3-36)
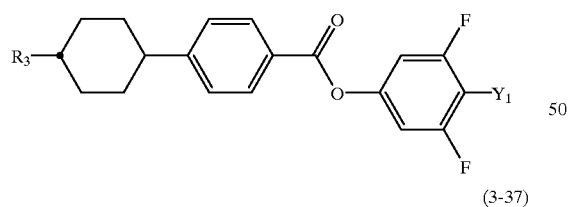
(3-37)
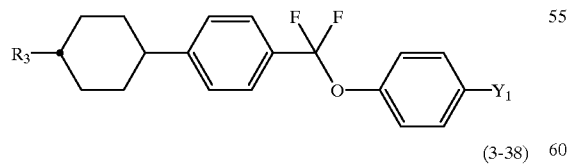
(3-38)
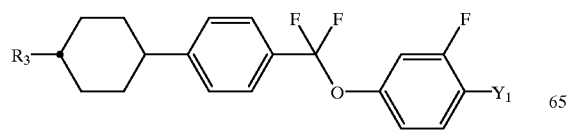
-continued
(3-39)
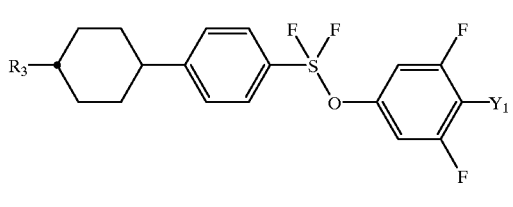
(3-40)
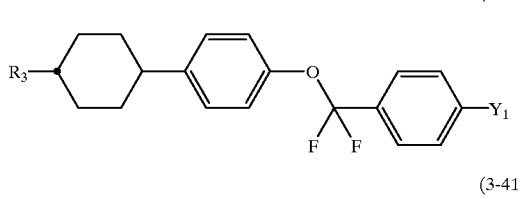
(3-41)
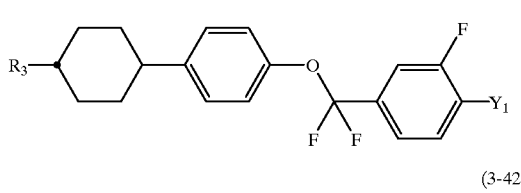
(3-42)
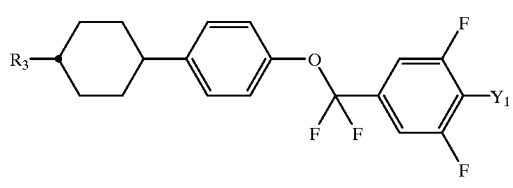
(3-43)
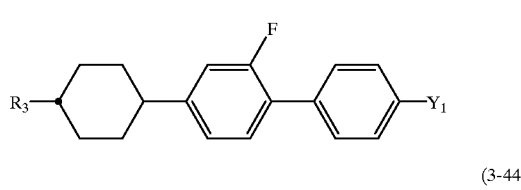
(3-44)
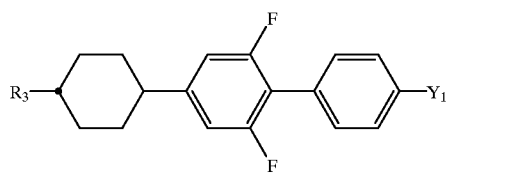
(3-45)
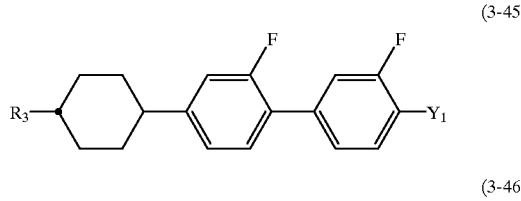
(3-46)
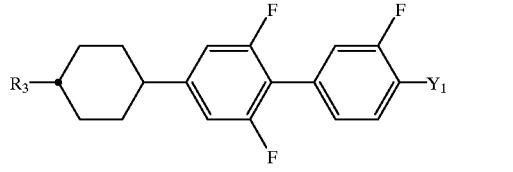

(3-47)
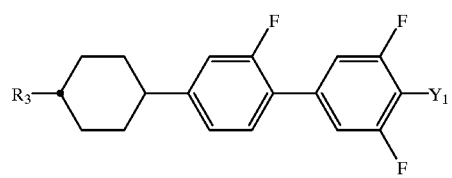
(3-48)
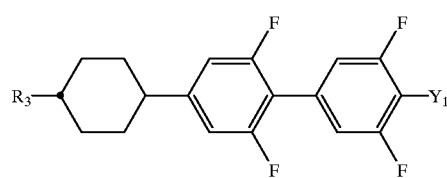
(3-49)
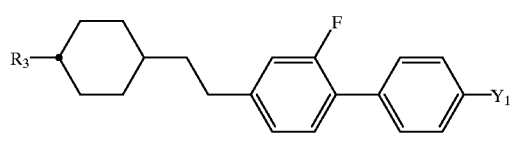
(3-50)
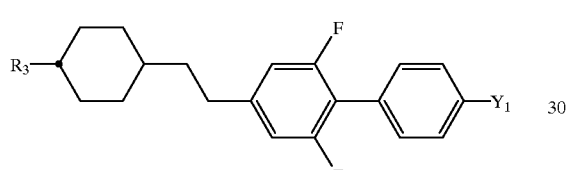
(3-51)
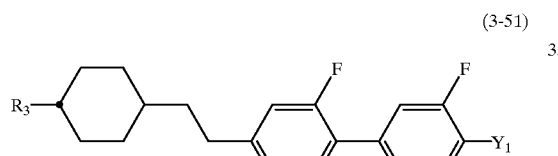
(3-52)
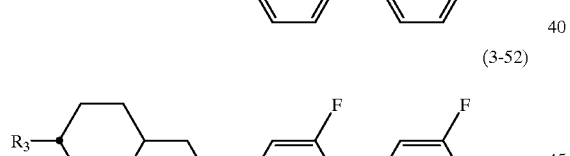
(3-53)
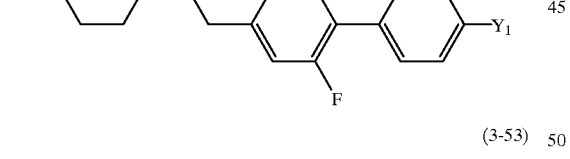
(3-54)
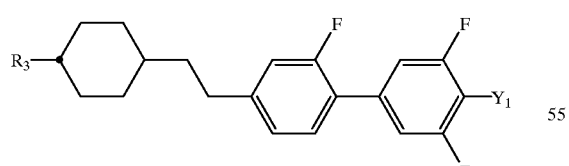
(3-55)
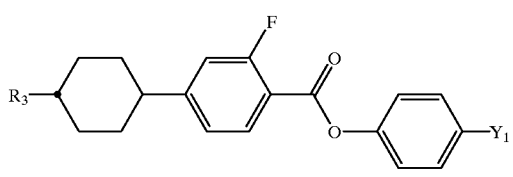
(3-56)
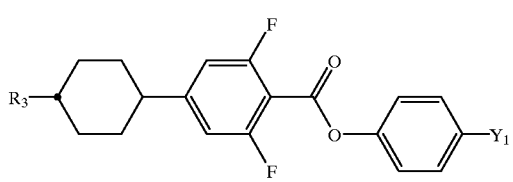
(3-57)
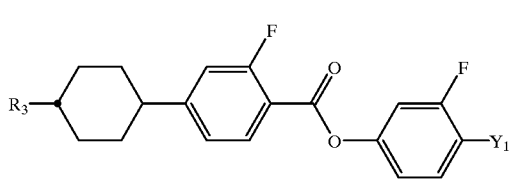
(3-58)
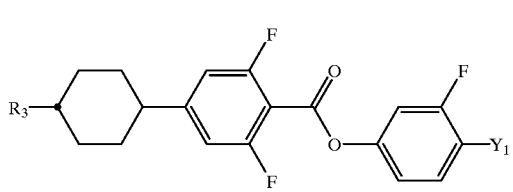
(3-59)
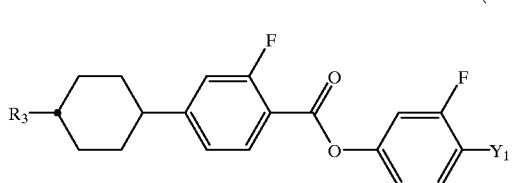
(3-60)
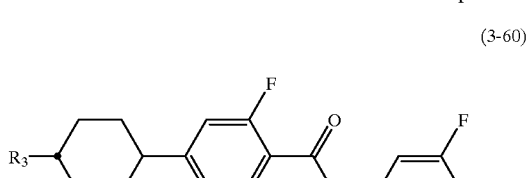
(3-61)
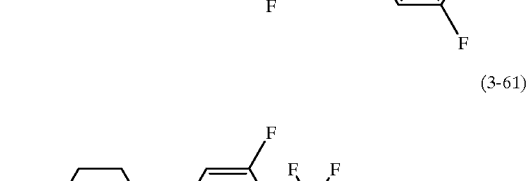

(3-62)
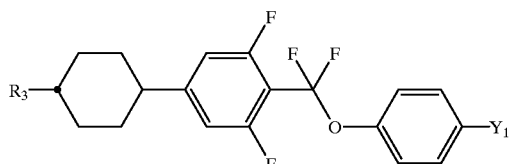
(3-63)
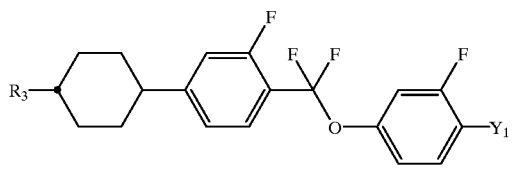
(3-64)
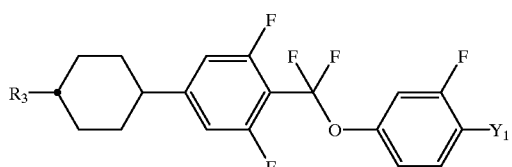
(3-65)
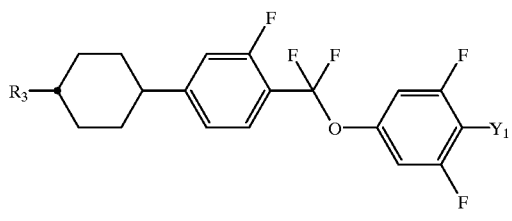
(3-66)
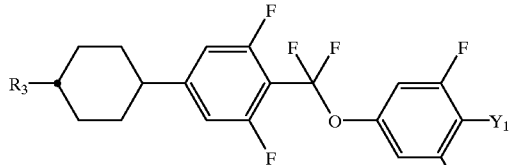
(3-67)
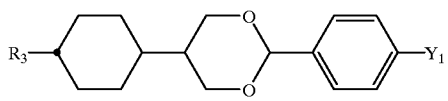
(3-68)
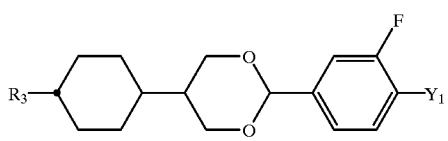
(3-69)
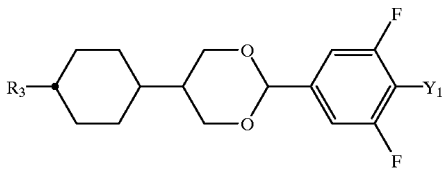
(4-1)
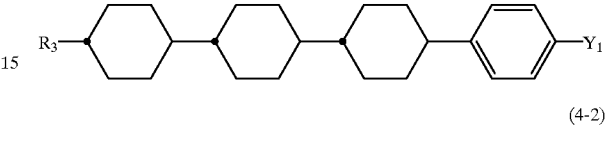
(4-2)
(4-3)
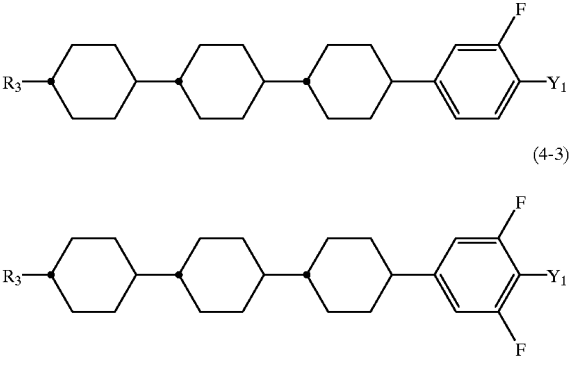
(4-4)
(4-5)
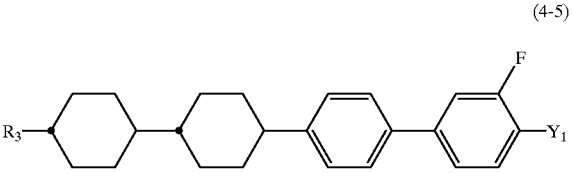
(4-6)
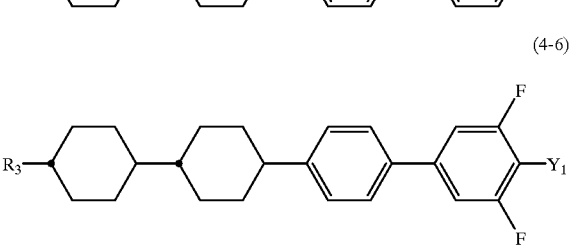
(4-7)
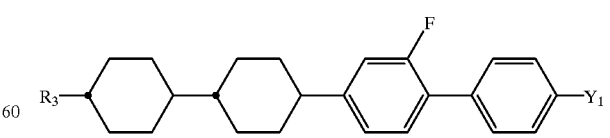

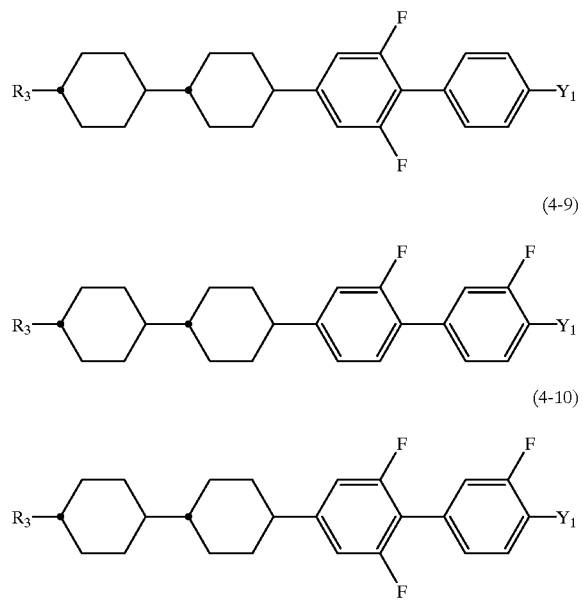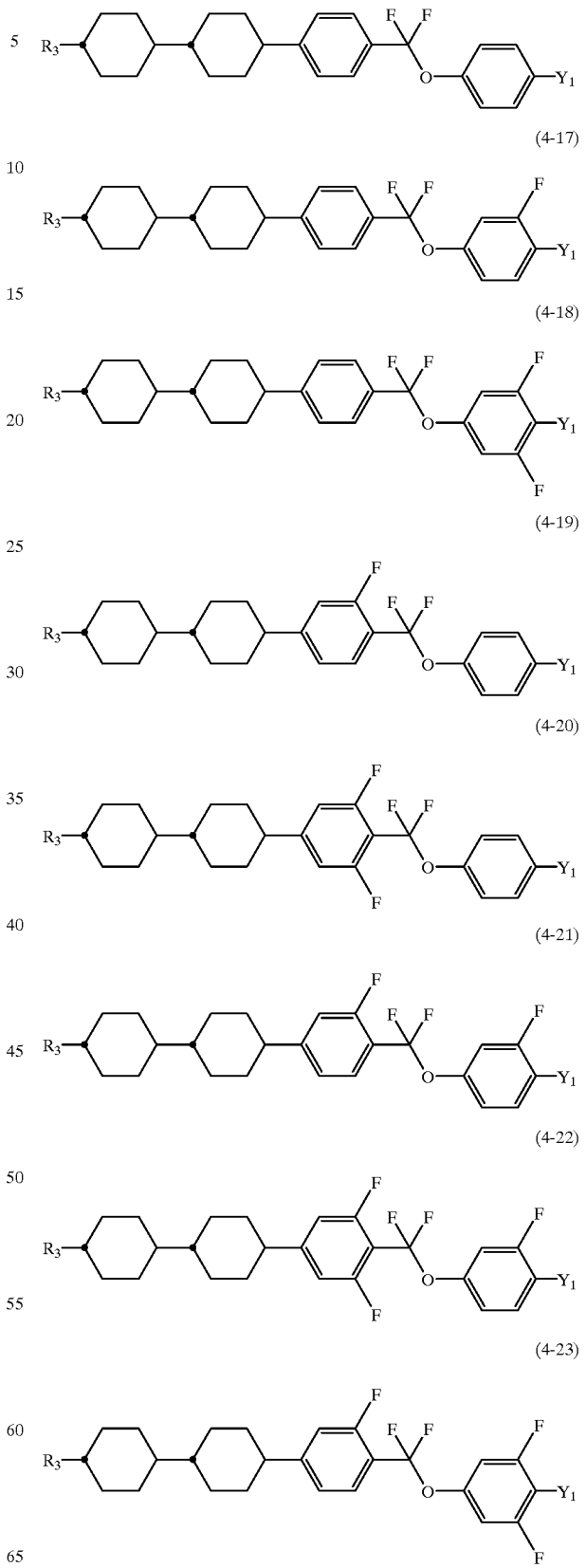

(4-24)

The compounds represented by general formulas (2)–(4) are useful compounds in the case of preparation of liquid crystal compositions for TFT which require high reliability, such as a positive dielectric anisotropy value, good thermal stability and chemical stability, and high voltage holding ratio.

The usage of the compounds represented by general formulas (2)–(4), in the case of preparation of a liquid crystal composition for TFT, is within any range of 1–99% by weight, preferably 10–97% by weight, more preferably 40–95% by weight. Moreover, in this case, the compounds represented by general formulas (7)–(9) may be contained. In the case of preparation of liquid crystal compositions for a TN display mode, the compounds represented by general formulas (2)–(4) also can be used As the compounds represented by general formulas (5) and (6), wherein $R_4$, $R_5$ and $Y_2$ have the same meaning as described above, the following compounds are preferably exemplified.

(5-1)
(5-2)
(5-3)
(5-4)
(5-5)
(5-6)
(5-7)
(5-8)
(5-9)
(5-10)
(5-11)
(5-12)
(5-13)
(5-14)
(5-15)
(5-16)

(5-17)
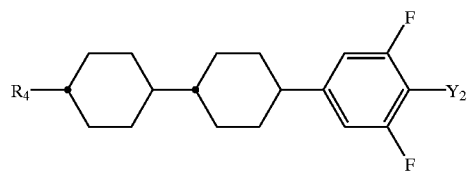
(5-18)
(5-19)
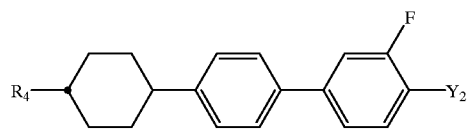
(5-20)
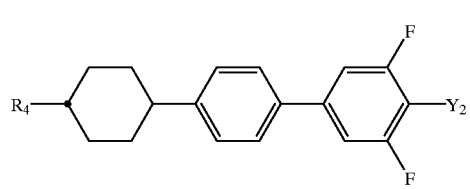
(5-21)
(5-22)
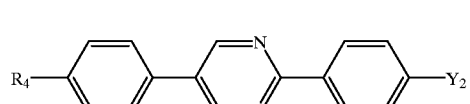
(5-23)
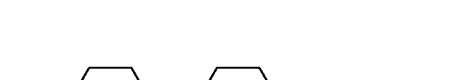
(5-24)
(5-25)
(5-26)
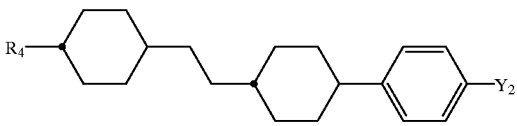
(5-27)
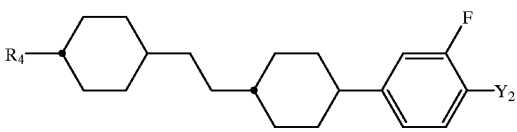
(5-28)
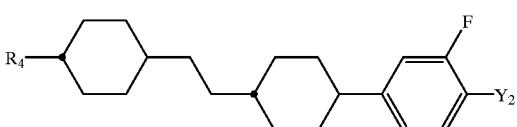
(5-29)
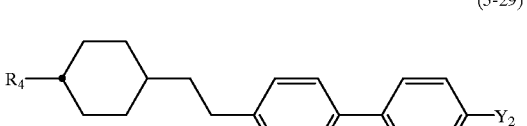
(5-30)
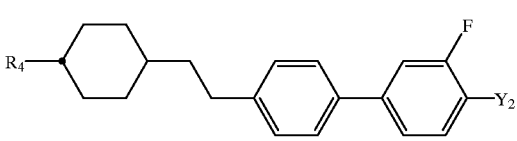
(5-31)
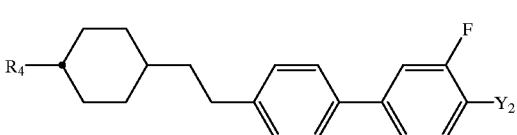
(5-32)
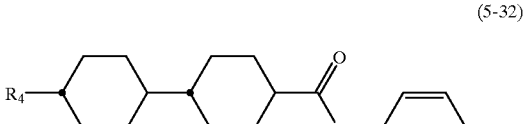
(5-33)
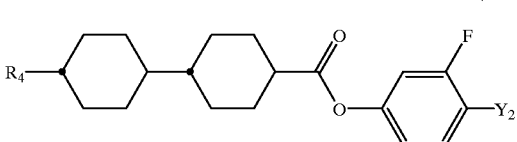

(5-34)
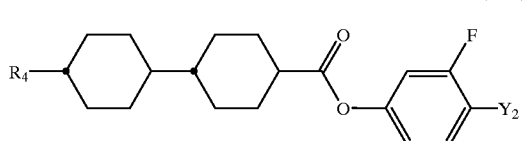

(5-35)
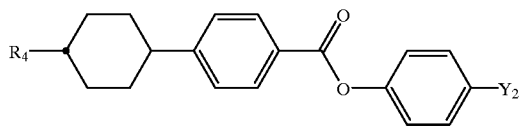

(5-36)
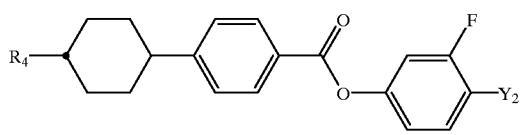

(5-37)
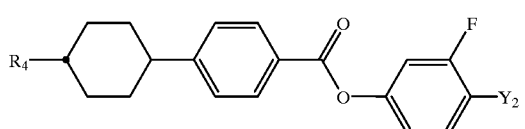

(5-38)

(5-39)
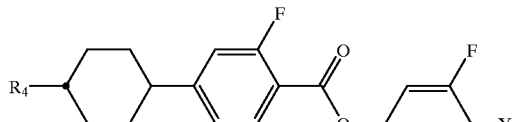

(5-40)
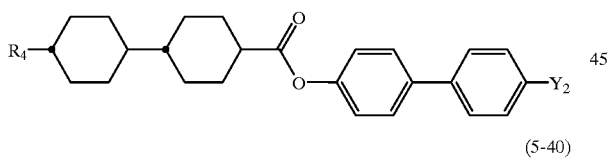

(6-1)
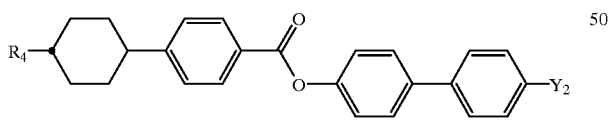

(6-2)
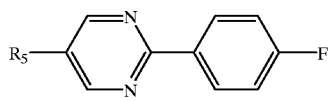

(6-3)
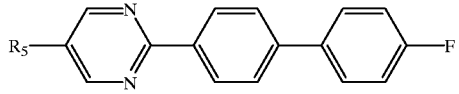

The compounds represented by general formulas (5) and (6) are used for obtaining a high positive dielectric anisotropy value and low threshold voltage. Further, they are used for controlling an optical anisotropy value, and expanding the nematic range, for example, to obtain a high clearing point. Moreover, they are used for improving the steepness of a transmission-voltage curve of liquid crystal compositions for a STN display mode and a TN display mode.

The compounds represented by general formulas (5) and (6) are particularly useful for preparing liquid crystal composition for a STN display mode and a TN display mode.

The usage of the compound represented by general formulas (5) and (6) is increased, then, the threshold voltage of the liquid crystal composition, and the viscosity is increased Accordingly, in low voltage driving, it is advantageous to use in large quantities so far as the viscosity of the liquid crystal composition satisfy the desired characteristic value. The usage of the compound represented by general formulas (5) and (6), for preparing the liquid crystal composition of the STN display mode or the TN display mode, it is able to use in the range of 0.1–99.9% by weight, preferably 10–97% by weight, more preferably 40–95% by weight.

As the compounds represented by general formulas (7)–(9), wherein $R_6$ and $R_7$ represents the same meaning as described above, the following compounds are preferred.

(7-1)

(7-2)
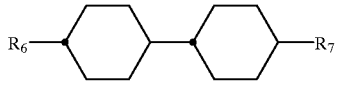

(7-3)
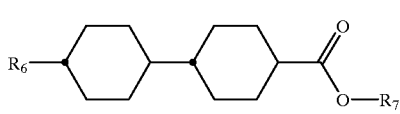

(7-4)
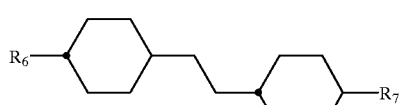

(7-5)
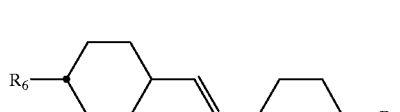

(7-6)
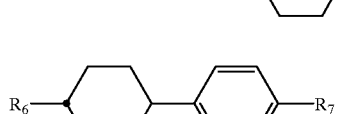

(7-7) 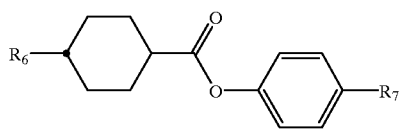
(7-8) 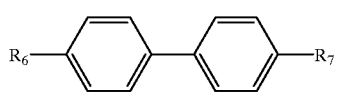
(7-9) 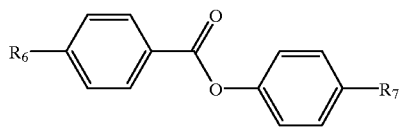
(7-10) 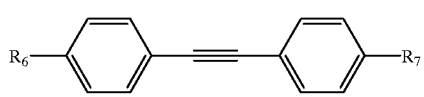
(7-11) 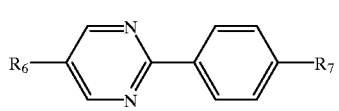
(8-1) 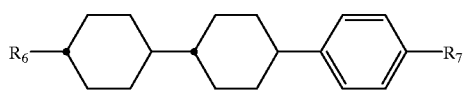
(8-2) 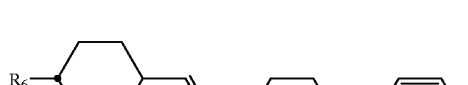
(8-3) 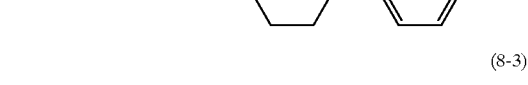
(8-4) 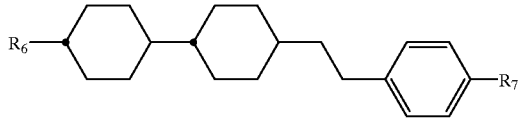
(8-5) 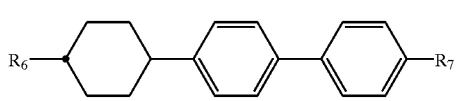
(8-6) 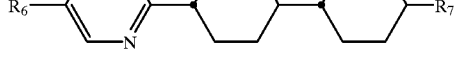
(8-7) 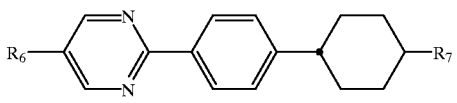
(8-8) 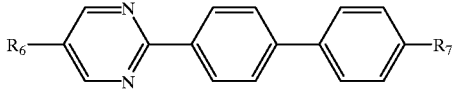
(8-9) 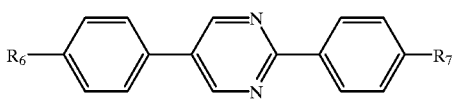
(8-10) 
(8-11) 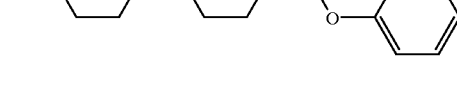
(8-12) 
(8-13) 
(8-14) 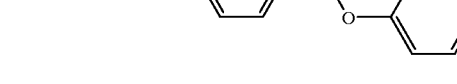
(8-15) 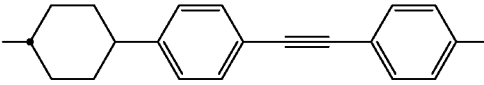
(8-16) 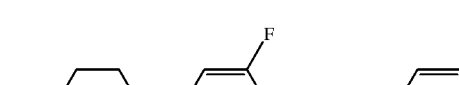

(8-17)
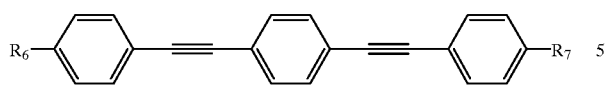

(8-18)
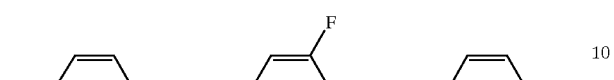

(9-1)
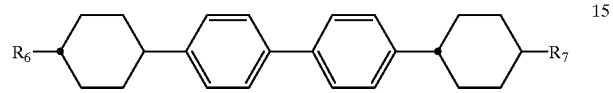

(9-2)
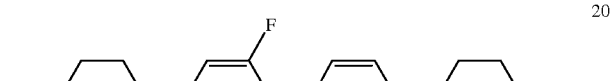

(9-3)

(9-4)

(9-5)
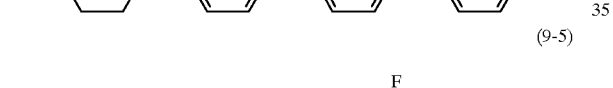

(9-6)
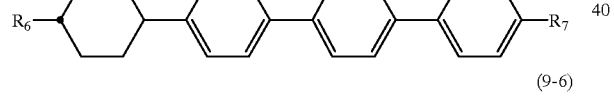

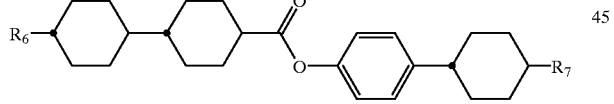

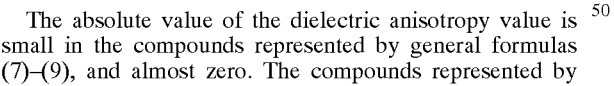

The absolute value of the dielectric anisotropy value is small in the compounds represented by general formulas (7)–(9), and almost zero. The compounds represented by general formula (7) are used to control the viscosity or optical anisotropy value of compositions. The compounds represented by general formulas (8) and (9) are used for spreading the nematic range to elevate the clearing point and the like and for controlling the optical anisotropy value of compositions.

When the usage of the compounds represented by general formulas (7)–(9) is increased, the threshold voltage becomes high, but the viscosity becomes low. Accordingly, so long as the threshold voltage of the liquid crystal compositions satisfies the necessary value, the usage in large quantities is preferred The usage of the compounds represented by general formulas (7)–(9) is less than 40% by weight in the preparation of liquid crystal compositions for the TFT display mode, and more preferably less than 35% by weight.

Further, in the preparation of liquid crystal compositions for the STN display mode or the TN display mode, the usage is less than 70% by weight and more preferably less than 60% by weight.

Moreover, in the present invention, except special cases such as liquid crystal compositions for a OCB (Optically Compensated Birefringence) mode, generally, for inducing a spiral configuration of the liquid crystal compositions to control the necessary twist angle and to inhibit the reverse twist, an optically active compound is added. In the liquid crystal compositions of the present invention, although any well-known optically active compounds can be used, preferably the following optically active compounds represented by formulas (OP-1)–(Op-8) can be exemplified.

(Op-1)
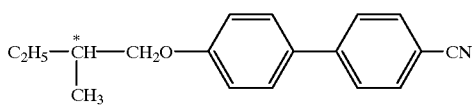

(Op-2)
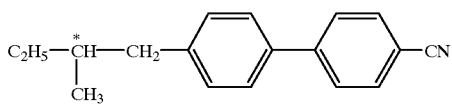

(Op-3)
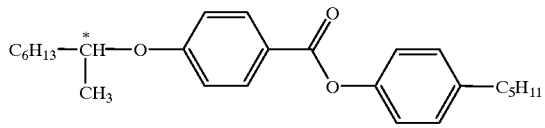

(Op-4)
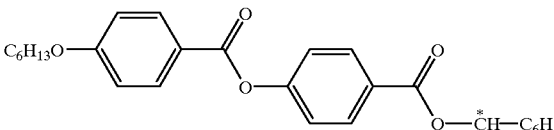

(Op-5)

$C_3H_7$—⟨cyclohexyl⟩—⟨cyclohexyl⟩—⟨phenyl⟩—$CH_2$—$\overset{*}{C}H$—$C_2H_5$
                                                        |
                                                        $CH_3$ (Op-6)

$C_5H_{11}$—⟨phenyl⟩—⟨phenyl⟩—C(=O)—O—$\overset{*}{C}H$—⟨phenyl⟩
                                           |
                                           $C_2H_5$ (Op-7)

$C_8H_{17}O$—⟨phenyl⟩—⟨phenyl⟩—C(=O)—O—$\overset{*}{C}H$—⟨phenyl⟩
                                             |
                                             $C_2H_5$

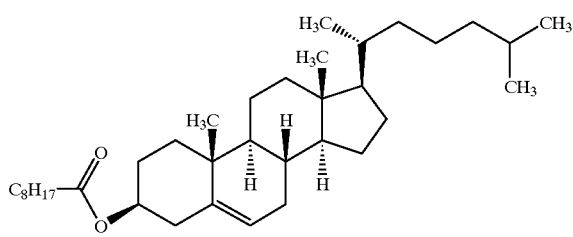
(Op-8)

The twist pitch of the liquid crystal compositions of the present invention is generally controlled by adding the said optically active compounds. The twist pitch is preferably adjusted to 40–200 μm in the liquid crystal compositions for TFT or TN. In the liquid crystal compositions for STN, 6–20 μm are preferred. In addition, in a bistable TN mode, 1.5–4 μm is preferred. Moreover, to control the temperature dependency of the pitch, two or more optically active compounds may be added.

The liquid crystal compositions of the present invention can be produced by conventional methods. In general, the compositions are obtained by dissolving several kinds of components each other at a high temperature.

Further, the liquid crystal compositions of the present invention can be used as those of the guest-host (GH) mode by adding dichroic dye such as a merocyanin type, a styryl type, an azo type, an azomethyne type, an azoxy type, a quinophthalon type, an anthraquinone type, and tetrazine type. Otherwise, the compositions can be used for NCAP prepared by micro-capsulation of a nematic liquid crystal or for a polymer dispersion liquid crystal display PDLCD represented by a polymer network liquid crystal device (PNLCD). In addition, the compositions can be used for an electrically controlled birefringence (ECB) mode or a dynamic scattering (DS) mode.

Any compounds represented by general formula (1) can be prepared by well-known method as described in, for example, 4th edition, Jikken Kagaku Kouza, (Maruzen), J. Oig. Chem., 42, 1821 (1977), J. Chem. Soc. Perkin Trans. 2, 2041 (1989).

Preferable synthetic process of representative compounds are described in the following.

The synthetic process of the compound represented by general formula (1-A):

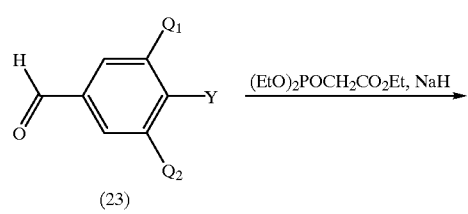

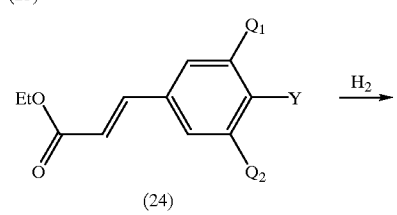

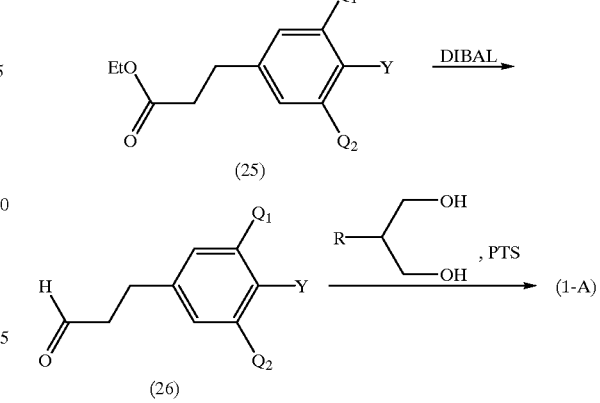

Benzaldehyde derivative (23) is reacted to a reactant solution of ethyl diethylphosphono acetate and sodium hydride to obtain compound (24). The compound (24) is hydrogenated by using a catalyst such as palladium, the resulting ester derivative (25) is reduced by using di-isobutyl aluminum hydride (abbreviated by DIBAL, hereinafter) to obtain aldehyde derivative (26). This aldehyde derivative (26) and 2-alkyl-1,3-propandiol are refluxed under dehydration in the presence of an acidic catalyst such as para-toluene sulfonic acid (abbreviated by PTS, hereinafter) or acidic ion exchange resin (Amberlyst R) to obtain the compound represented by general formula (1-A).

The synthetic process of the compound represented by general formula (1-B).

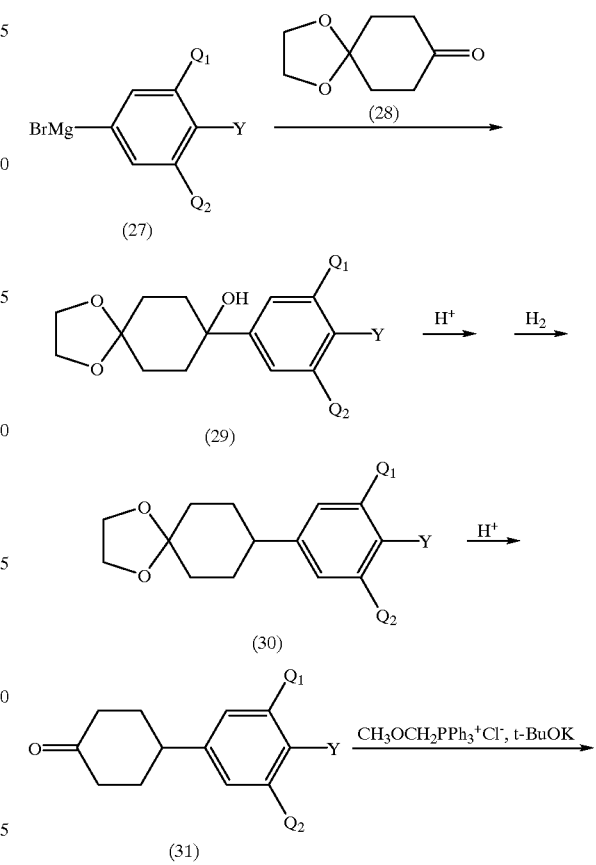

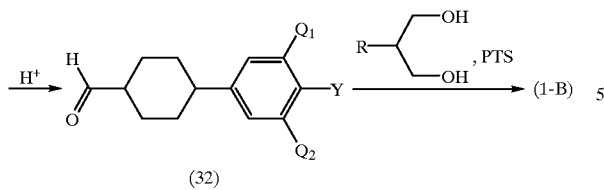

Cyclohexanedion monoethylene ketal (28) is reacted to Grignard reagent (27) to obtain tertiary alcohol (29). The resulting compound is dehydrated and hydrogenated, and then deprotected under acidic conditions to obtain a cyclohexanone derivative (31). To this compound, methoxymethyl triphenylphosphonium chloride is reacted, and then deprotected under acidic conditions to obtain aldehyde derivative (32). This compound is reacted with 2-alkyl-1,3-propan-diol under acidic conditions to obtain the compound represented by general formula (1-B).

The synthetic process of the compound represented by general formula (1-C):

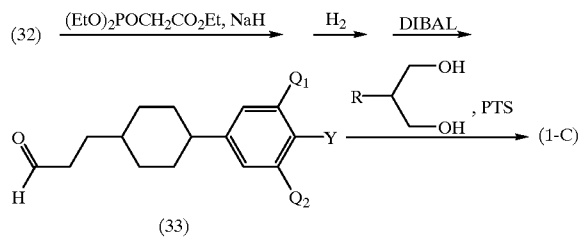

The compound represented by general formula (1-C) can be obtained by using the same method as described in the synthetic process of the compound represented by general formula (1-A) except replacing aldehyde derivative (23) by aldehyde derivative (32).

The synthetic process of the compound represented by general formula (1-D):

(34) MgBr—[ring with $Q_1$, $Q_2$, Y] $\xrightarrow{(28)}$ ----→ (1-D)

The compound represented by general formula (1-D) can be obtained by using the same method as described in the synthetic process of the compound represented by general formula (1-B) except replacing Grignard reagent (27) by Grignard reagent (34).

The synthetic process of the compound represented by general formula (1-E):

(35) [dioxane-ring-CH$_2$CH$_2$-aryl with $Q_3$, $Q_4$, R] $\xrightarrow{\text{BuLi}}$ Br—[ring with $Q_1$, $Q_2$, Y] (36)

$\xrightarrow{\text{ZnCl}_2, \text{Pd(0)}}$ (1-E)

Compound (35) represented by general formula (1-A), wherein Y is a hydrogen atom, is synthesized. Compound (35) is reacted with butyllithium to obtain a lithio compound, and then reacted with zinc chloride, palladium (0) and compound (36) in order, to obtain the compound represented by general formula (1-E). This process is applied by the method described in J. Org. Chem., 42, 1821 (1977). Further, the method described in J. Chem. Soc. Perkin Trans. 2, 2041 (1989) can be applied.

The synthetic process of the compound represented by general formula (1-L):

(26) $\xrightarrow{(\text{EtO})_2\text{POCH}_2\text{CO}_2\text{Et, NaH}}$

(37) EtO-C(=O)-CH=CH-CH$_2$CH$_2$-[ring with $Q_1$, $Q_2$, Y] $\xrightarrow{\text{H}_2}$ $\xrightarrow{\text{DIBAL}}$

(38) H-C(=O)-CH$_2$CH$_2$CH$_2$-[ring with $Q_1$, $Q_2$, Y] + R-CH(OH)-CH$_2$-OH, PTS → (1-L)

The compound represented by general formula (1-L) can be obtained by using the same method as described in the synthetic process of the compound represented by general formula (1-A) except replacing aldehyde derivative (23) by compound (26).

The synthetic process of the compound represented by general formula (1-M):

(33) $\xrightarrow{(\text{EtO})_2\text{POCH}_2\text{CO}_2\text{Et, NaH}}$ $\xrightarrow{\text{H}_2}$ $\xrightarrow{\text{DIBAL}}$

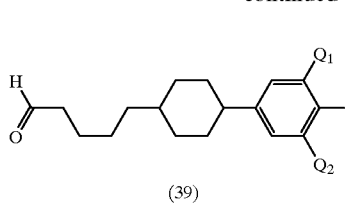

(39) → (1-M)

The compound represented by general formula (1-M;) can be obtained by using the same method as described in the synthetic process of the compound represented by general formula (1-A) except replacing aldehyde derivative (23) by compound (33).

The synthetic process of the compound represented by general formula (1-N):

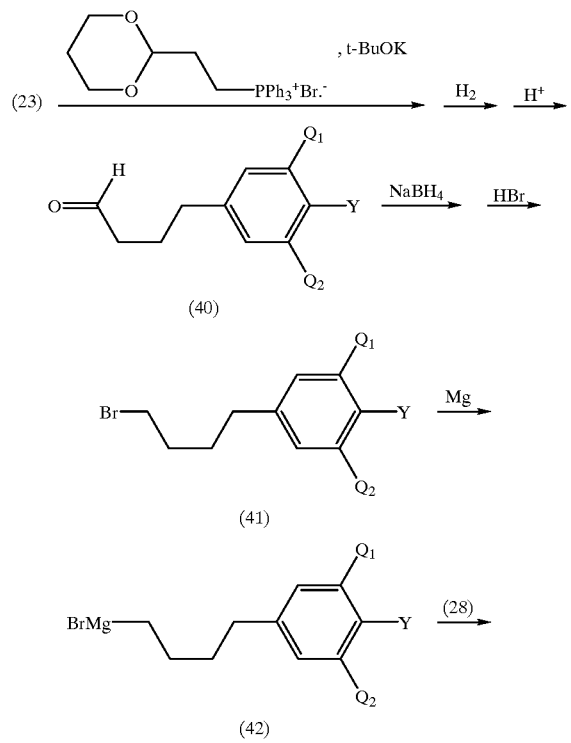

- - - → (1-N)

Aldehyde derivative (23) is reacted to a ylide prepared from a base such as 1,3-dioxane-2-yl ethyltriphenylphosphonium bromide and potassium-t-butoxide, and the resulting product is hydrogenated, and then it is deprotected by an add to obtain aldehyde derivative (40). A reduction agent such as sodium boron hydride is reacted to the derivative, the resulting alcohol derivative is brominated with hydrobromic acid or the like to obtain compound (41), and then it is reacted with magnesium to prepare Grignard reagent (42). The compound represented by general formula (1-N) can be obtained by using the same method as described in the synthetic process of the compound represented by general formula (1-B) except replacing Grignard reagent (27) by Grignard reagent (42).

The synthetic process of the compound represented by general formula (1-O):

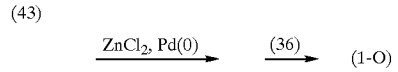

(43) → (1-O)

Compound (43) represented by general formula (1-L), wherein Y is a hydrogen atom, is synthesized. The compound represented by general formula (1-O) can be obtained by using the same method as described in the synthesis of the compound represented by general formula (1-E) except replacing compound (35) by compound (43).

The synthetic process of the compound represented by general formula (1-P):

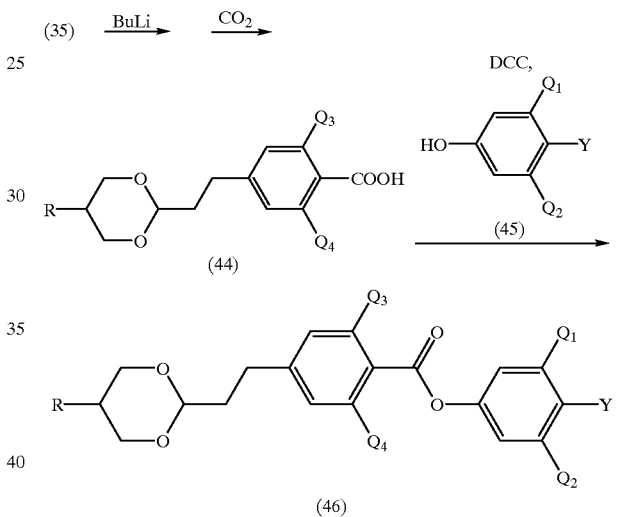

Compound (35) is reacted with butyl lithium, the resulting lithio compound is reacted with carbon dioxide as described in 4th edition, Jikken Kagaku Kouza Maruzen), Vol.22, page 16, and a carboxylic acid derivative (44) is obtained. To this carboxylic acid derivative (44), by using a method described in the said Jikken Kagaku Kouza, Vol.22, page 46, phenol derivative (45) is reacted in the presence of 4-dimethylaminopyridine and 1,3-dicyclohexylcarbodiimide (abbreviated as DCC, hereinafter), and ester derivative (46) can be obtained. This compound is represented by general formula (1-P) wherein Zd is —COO—.

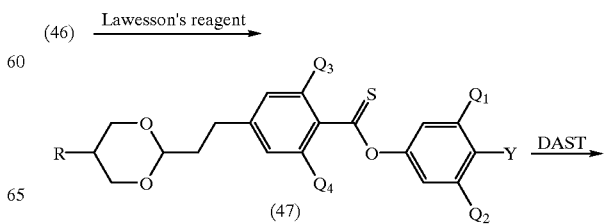

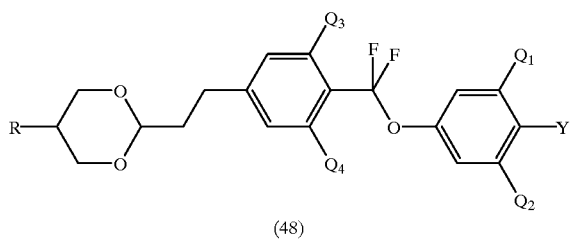

(48)

As described in Bull. Soc. Chim. Belg., 87, 293 (1978), ester compound (46) is reacted with a Lawesson's reagent, the resulting thionester (47) is reacted with diethylamino sulfur trifluoride (abbreviated as DAST, hereinafter) in methylene chloride or glyme solvent, or as described in Japanese Patent Laid-Open Publication No. 6-263679, it is reacted with tetra-butyl ammonium di-hydrogen tri-fluoride (abbreviated as TBAH2F3, hereinafter) and N-iodo succinimide (abbreviated as NIS hereinafter) in the presence of mehtylene chloride and 1,2-dichloroethane, and difluoromethylether (48) can be obtained. The compound is represented by general formula (1-P) wherein Zd is —CF$_2$O—.

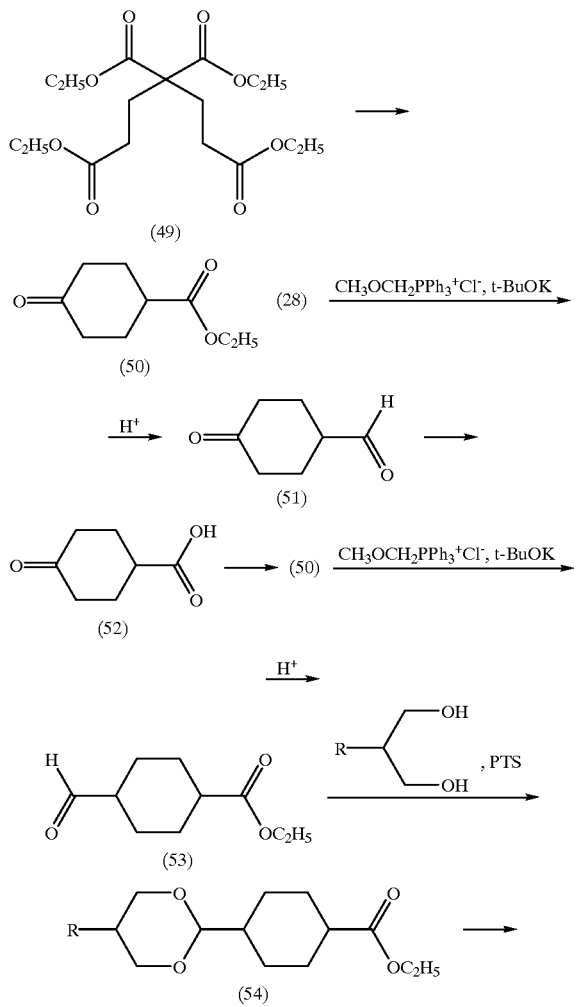

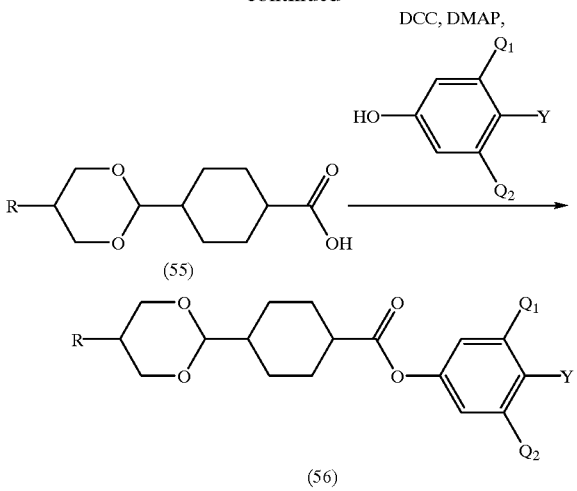

Using a method described in Helv. Chim. Acta., 27, 793 (1944), cyclohexanone-4-carboxylic acid ethyl ester (50) can be synthesized from pentane-1,3,3,5-tetracrboxylic acid tetraethyl ester (49). Otherwise, cyclohexanedione monoethylene ketal is reacted with methoxymethyltriphenyl phosphonium chloride, and deprotected under acidic conditions, and aldehyde derivative (51) is obtained. The resulting compound is oxidized by a method described in 4th edition, Jikken Kagaku Kouza, Vol. 22, pages 3–4, to obtain carboxylic acid derivative (52). Then, by a method described in 4th edition, Jikken Kagaku Kouza, Vol. 22, pages 44–47, the derivative is reacted to obtain ester compound (50). This compound is reacted with methoxy methyl triphenyl phosphonium chloride, and the resulting product is deprotected under acidic conditions to obtain aldehyde derivative (53). Except replacing compound (26) by compound (53), using the same method as described in the synthesis of the compound represented by general formula (1-A), compound (54) can be obtained. From the compound (54), compound (55) is synthesized by using a hydrolysis method under alkali or neutral conditions as described in 4th edition, Jikken Kagaku Kouza, Vol. 22, pages 8–11. And then ester compound (56) can be synthesized by a method described in 4th edition, Jikken Kagaku Kouza, Vol. 22, pages 45–47. This compound is represented by general formula (1-S) wherein Zd is —COO—.

By using the same method as described in the synthesis of compound (48) except replacing compound (46) by compound (56), the compound represented by general formula (1-S), wherein Zd is —CF$_2$O—, can be obtained.

The compounds having four rings represented by general formulas (1-F)–(1-K and (1-Q), and (1-R) can be easily produced by using the above synthetic method of the tricyclic compounds.

The compounds having a 1-sila-1,4-cyclohexylene group and a 4-sila-4-cyclohexylene group in the present invention can be prepared by applying the method described in Japanese Patent Laid-open Publication 7-70148.

As examples of the liquid crystal compositions containing the compounds of the present invention, the following composition examples Composition examples 1–49) can be represented In each composition example, each compound is represented by a symbol based on the abbreviation method described in the following Table 1, and groups represented in each column of left end groups, bonding groups, ring structure, and right end group correspond to those in the column of symbolized examples. As an example, in the following constitutional formula, when hydrogen atoms of trans-1,4-cyclohexylene and trans, trans-bicyclohexane-4,4'-diyl are replaced at the positions of $J_1$, $J_2$ and $J_3$, the symbol is read as H[1D, 2D, 3D], when the hydrogen atoms are replaced at the positions of $J_5$, $J_6$ and $J_7$, the symbol is read as H[5D, 6D, 7D], and the numbers in [ ] show the positions replaced by heavy hydrogen atoms.

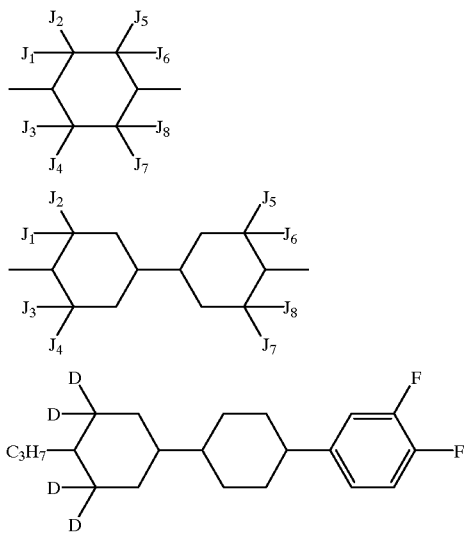

The compound Nos. are the same as in those of the examples described in the following, and the content of the compounds means % by weight, except special mention.

The data of characteristics in using examples are shown by $T_{N1}$ (nematic-isotropy liquid transition temperature or clearing point), η (viscosity: measured temperature 20.0° C.), Δn(optical anisotropy: measured temperature 25.0° C., Δε1(dielectric anisotropy: measured temperature 25.0° C.) and $V_{th}$ (threshold voltage: measured temperature 25.0° C.).

TABLE 1

Representation of compounds by using symbols
R—(A₁)—Z₁—Zₙ—(Aₙ)—X

| 1) Left end groups R— | Symbols | 3) Bonding groups —Z₁—, —Zₙ— | Symbols |
|---|---|---|---|
| $C_nH_{2n+1}$— | n- | —$C_2H_4$— | 2 |
| $C_nH_{2n+1}OC_mH_{2m}$— | nOm- | —COO— | E |
| | | —$CF_2O$— | CF2O |

| 2) Ring Structure —(A₁), —(Aₙ)— | Symbols | 4) Right end groups —X | Symbols |
|---|---|---|---|
| (benzene) | B | —F | —F |
| (fluorobenzene) | B(F) | —Cl | —CL |

TABLE 1-continued

Representation of compounds by using symbols
R—(A₁)—Z₁—Zₙ—(Aₙ)—X

| | | | |
|---|---|---|---|
| (difluorobenzene) | B(F,F) | —$OCF_3$ | —OCF3 |
| (cyclohexane) | H | —$C_nH_{2n+1}$ | -n |
| (pyrimidine) | Py | | |
| (dioxane) | D | | |
| (cyclohexene) | Ch | | |

5) Symbolized examples

Example 1  3-H2B(F,F)B(F)—F

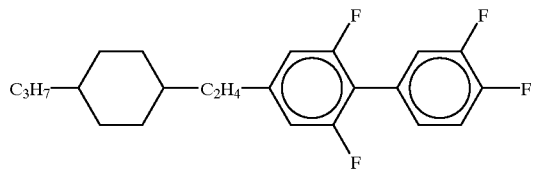

Example 2  3-HB(F)TB-2

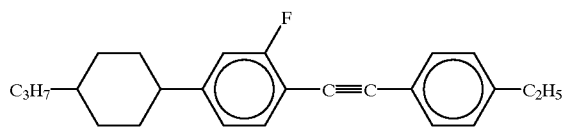

Example 3  IV2-BEB(F,F)—C

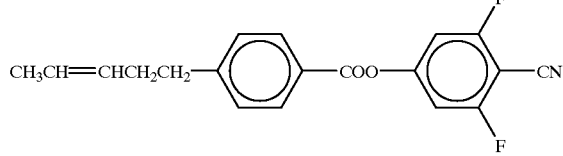

Composition Example 1

| 3-DHB(F,F)—F | 3.0% |
|---|---|
| (Compound No. 21) | |
| 3-D2B(F,F)B(F)—OCF3 | 3.0% |

-continued

| | |
|---|---|
| (Compound No. 98) | |
| 1V2-BEB(F,F)—C | 5.0% |
| 3-HB—C | 25.0% |
| 1-BTB-3 | 5.0% |
| 2-BTB-1 | 10.0% |
| 3-HH-4 | 11.0% |
| 3-HHB-1 | 5.0% |
| 3-HHB-3 | 9.0% |
| 3-H2BTB-2 | 4.0% |
| 3-H2BTB-3 | 4.0% |
| 3-H2BTB-4 | 4.0% |
| 3-HB(F)TB-2 | 6.0% |
| 3-HB(F)TB-3 | 6.0% |
| Op-4 | 0.8 part |

$T_{n1} = 83.5(°C.)$
$\eta = 17.5 \text{ (mPa·s)}$
$\Delta n = 0.159$
$\Delta \epsilon 1 = 8.1$
$V_{th} = 1.98(V)$
$P = 11 \mu m$

Composition Example 2

| | |
|---|---|
| 3-D2B—CF3 (Compound No. 11) | 2.0% |
| 3-D4B—CF3 (Compound No. 261) | 2.0% |
| 3-DHB(F,F)B(F)—CL (Compound No. 175) | 4.0% |
| V2-HB—C | 10.0% |
| 1V2-HB—C | 10.0% |
| 3-HB—C | 11.0% |
| 3-H[1D,2D,3D]B—C | 9.0% |
| 3-HB(F)—C | 5.0% |
| 2-BTB-1 | 2.0% |
| 3-HH-4 | 8.0% |
| 3-HH—VFF | 6.0% |
| 2-H[1D,2D,3D]HB—C | 3.0% |
| 3-HHB—C | 6.0% |
| 3-HB(F)TB-2 | 8.0% |
| 3-H2BTB-2 | 5.0% |
| 3-H2BTB-3 | 5.0% |
| 3-H2BTB-4 | 4.0% |

$T_{n1} = 89.2(°C.)$
$\eta = 19.0 \text{ (mPa·s)}$
$\Delta n = 0.151$
$\Delta \epsilon 1 = 8.8$
$V_{th} = 1.98(V)$

Composition Example 3

| | |
|---|---|
| 3-DHB(F)—OCF3 (Compound No. 22) | 5.0% |
| 2O1-BEB(F)—C | 5.0% |
| 3O1-BEB(F)—C | 15.0% |
| 4O1-BEB(F)—C | 13.0% |
| 5O1-BEB(F)—C | 10.0% |
| 2-HHB(F)—C | 15.0% |
| 3-HHB(F)—C | 15.0% |
| 3-HB(F)TB-2 | 4.0% |
| 3-HB(F)TB-3 | 4.0% |
| 3-HB(F)TB-4 | 4.0% |
| 3-HHB-1 | 6.0% |
| 3-HHB—O1 | 4.0% |

$T_{n1} = 92.6(°C.)$
$\eta = 86.5 \text{ (mPa·s)}$
$\Delta n = 0.148$
$\Delta \epsilon 1 = 31.2$
$V_{th} = 0.86(V)$

Composition Example 4

| | |
|---|---|
| 3-DHB(F,F)—F (Compound No. 21) | 3.0% |
| 3-DHB(F)—OCF3 (Compound No. 22) | 3.0% |
| 5-PyB—F | 4.0% |
| 3-PyB(F)—F | 4.0% |
| 2-BB—C | 5.0% |
| 4-BB—C | 4.0% |
| 5-BB—C | 5.0% |
| 2-PyB-2 | 2.0% |
| 3-PyB-2 | 2.0% |
| 4-PyB-2 | 2.0% |
| 6-PyB—O5 | 3.0% |
| 6-PyB—O6 | 3.0% |
| 6-PyB—O7 | 3.0% |
| 3-PyBB—F | 6.0% |
| 4-PyBB—F | 6.0% |
| 5-PyBB—F | 3.0% |
| 3-HHB-1 | 6.0% |
| 3-HHB-3 | 8.0% |
| 2-H2BTB-2 | 4.0% |
| 2-H2BTB-3 | 4.0% |
| 2-H2BTB-4 | 5.0% |
| 3-H2BTB-2 | 5.0% |
| 3-H2BTB-3 | 5.0% |
| 3-H2BTB-4 | 5.0% |

$T_{n1} = 91.7(°C.)$
$\eta = 35.1 \text{ (mPa·s)}$
$\Delta n = 0.195$
$\Delta \epsilon 1 = 7.6$
$V_{th} = 2.19(V)$

Composition Example 5

| | |
|---|---|
| 3-D2B(F,F)B(F)—OCF3 (Compound No. 98) | 5.0% |
| 3-D2B—CF3 (Compound No. 11) | 3.0% |
| 3-D4B—CF3 (Compound No. 261) | 2.0% |
| 3-DB—C | 8.0% |
| 4-DB—C | 5.0% |
| 2-BEB—C | 12.0% |
| 3-BEB—C | 4.0% |
| 3-PyB(F)—F | 3.0% |
| 3-HEB—O4 | 8.0% |
| 4-HEB—O2 | 6.0% |
| 5-HEB—O1 | 6.0% |
| 3-HEB—O2 | 5.0% |
| 5-HEB—O2 | 4.0% |
| 5-HEB-5 | 5.0% |
| 4-HEB-5 | 5.0% |
| 1O—BEB-2 | 4.0% |
| 3-HHB-1 | 6.0% |
| 3-HHEBB—C | 3.0% |
| 3-HBEBB—C | 3.0% |
| 5-HBEBB—C | 3.0% |

$T_{n1} = 67.4(°C.)$
$\eta = 39.9 \text{ (mPa·s)}$
$\Delta n = 0.119$ $\Delta\epsilon_1 = 11.1$
$V_{th} = 1.37(V)$

Composition Example 6

| | |
|---|---|
| 3-DHB(F,F)—F | 3.0% |
| (Compound No. 21) | |
| 3-D2B(F,F)B(F)—OCF3 | 3.0% |
| (Compound No. 98) | |
| 3-DHB(F)—OCF3 | 3.0% |
| (Compound No. 22) | |
| 3-HB—C | 13.0% |
| 7-HB—C | 3.0% |
| 1O1-HB—C | 6.0% |
| 3-HB(F)—C | 10.0% |
| 2-PyB-2 | 2.0% |
| 3-PyB-2 | 2.0% |
| 4-PyB-2 | 2.0% |
| 1O1-HH-3 | 7.0% |
| 2-BTB—O1 | 7.0% |
| 3-HHB-1 | 7.0% |
| 3-HHB—F | 4.0% |
| 3-HHB—O1 | 4.0% |
| 3-HHB-3 | 8.0% |
| 3-H2BTB-2 | 3.0% |
| 3-H2BTB-3 | 3.0% |
| 2-PyBH-3 | 4.0% |
| 3-PyBH-3 | 3.0% |
| 3-PyBB-2 | 3.0% |

$T_{n1} = 79.6(°\ C.)$
$\eta = 21.1\ (mPa \cdot s)$
$\Delta n = 0.137$
$\Delta\epsilon_1 = 8.5$
$V_{th} = 1.68(V)$

Composition Example 7

| | |
|---|---|
| 3-D2B—CF3 | 4.0% |
| (Compound No. 11) | |
| 3-DHB(F)—OCF3 | 5.0% |
| (Compound No. 22) | |
| 2O1-BEB(F)—C | 5.0% |
| 3O1-BEB(F)—C | 10.0% |
| 1V2-BEB(F,F)—C | 10.0% |
| 3-HH—EMe | 10.0% |
| 3-HB—O2 | 18.0% |
| 7-HEB—F | 2.0% |
| 3-HHEB—F | 2.0% |
| 5-HHEB—F | 2.0% |
| 3-HBEB—F | 4.0% |
| 2O1-HBEB(F)—C | 2.0% |
| 3-HB(F)EB(F)—C | 2.0% |
| 3-HBEB(F,F)—C | 2.0% |
| 3-HHB—F | 4.0% |
| 3-HHB—O1 | 4.0% |
| 3-HHB-3 | 10.0% |
| 3-HEBEB—F | 2.0% |
| 3-HEBEB-1 | 2.0% |

$T_{n1} = 74.5(°\ C.)$
$\eta = 33.7\ (mPa \cdot s)$
$\Delta n = 0.110$
$\Delta\epsilon_1 = 22.9$
$V_{th} = 1.01(V)$

Composition Example 8

| | |
|---|---|
| 3-DHB(F,F)—F | 3.0% |
| (Compound No. 21) | |
| 3-DHB(F,F)B(F)—CL | 3.0% |
| (Compound No. 175) | |
| 5-BEB(F)—C | 5.0% |
| V—HB—C | 11.0% |
| 5-PyB—C | 6.0% |
| 4-BB-3 | 11.0% |
| 3-HH-2V | 10.0% |
| 5-HH—V | 8.0% |
| V—HHB-1 | 7.0% |
| V2-HHB-1 | 15.0% |
| 3-HHB-1 | 9.0% |
| 1V2-HBB-2 | 7.0% |
| 3-HHEBH-3 | 5.0% |

$T_{n1} = 91.0(°\ C.)$
$\eta = 19.2\ (mPa \cdot s)$
$\Delta n = 0.116$
$\Delta\epsilon_1 = 6.1$
$V_{th} = 2.19(V)$

Composition Example 9

| | |
|---|---|
| 3-D2B—(F,F)B(F)—OCF3 | 5.0% |
| (Compound No. 98) | |
| 3-D2B—CF3 | 2.0% |
| (Compound No. 11) | |
| 3-D4B—CF3 | 3.0% |
| (Compound No. 261) | |
| 3-DHB(F,F)B(F)—CL | 5.0% |
| (Compound no. 175) | |
| 2O1-BEB(F)—C | 5.0% |
| 3O1-BEB(F)—C | 8.0% |
| 1V2-BEB(F,F)—C | 16.0% |
| 3-HB—O2 | 10.0% |
| 3-HH-4 | 3.0% |
| 3-HHB—F | 3.0% |
| 3-HHB-1 | 5.0% |
| 3-HHB—O1 | 4.0% |
| 3-HBEB—F | 4.0% |
| 3-HHEB—F | 7.0% |
| 5-HHEB—F | 7.0% |
| 3-H2BTB-3 | 4.0% |
| 3-H2BTB-4 | 4.0% |
| 3-HB(F)TB-2 | 5.0% |

$T_{n1} = 87.5(°\ C.)$
$\eta = 41.7\ (mPa \cdot s)$
$\Delta n = 0.133$
$\Delta\epsilon_1 = 28.2$
$V_{th} = 1.02(V)$

Composition Example 10

| | |
|---|---|
| 3-D2B—(F,F)B(F)—OCF3 | 5.0% |
| (Compound No. 98) | |
| 3-DHB(F)—OCF3 | 5.0% |
| (Compound No. 22) | |
| 2-BEB—C | 12.0% |
| 4-BEB—C | 6.0% |
| 3-HB—C | 22.0% |
| 3-HEB—O4 | 12.0% |
| 4-HEB—O2 | 8.0% |
| 5-HEB—O1 | 8.0% |
| 3-HEB—O2 | 6.0% |
| 5-HEB—O2 | 5.0% |
| 3-HHB-1 | 7.0% |
| 3-HHB—O1 | 4.0% |

$T_{n1} = 61.5(°\ C.)$

-continued $\eta$ = 29.0 (mPa · s)
$\Delta n$ = 0.107
$\Delta \epsilon 1$ = 10.3
$V_{th}$ = 1.32(V)

Composition Example 11

| | |
|---|---|
| 3-D4B—CF3 | 4.0% |
| (Compound No. 261) | |
| 3-DHB(F,F)—B(F)—CL | 4.0% |
| (Compound No. 175) | |
| 2-BEB—C | 10.0% |
| 5-BB—C | 8.0% |
| 7-BB—C | 7.0% |
| 1-BTB-3 | 7.0% |
| 2-BTB-1 | 10.0% |
| 1O—BEB-2 | 10.0% |
| 1O—BEB-5 | 12.0% |
| 2-HHB-1 | 4.0% |
| 3-HHB—F | 4.0% |
| 3-HHB-1 | 7.0% |
| 3-HHB—O1 | 4.0% |
| 3-HHB-3 | 9.0% |

$T_{n1}$ = 64.9(° C.)
$\eta$ = 20.8 (mPa · s)
$\Delta n$ = 0.155
$\Delta \epsilon 1$ = 6.9
$V_{th}$ = 1.72(V)

Composition Example 12

| | |
|---|---|
| 3-DHB(F,F)—F | 5.0% |
| (Compound No. 21) | |
| 3-D2B(F,F)—B(F)—OCF3 | 5.0% |
| (Compound No. 98) | |
| 1V2-BEB(F,F)—C | 6.0% |
| 3-HB—C | 10.0% |
| V2V—HB—C | 14.0% |
| V2V—HH-3 | 19.0% |
| 3-HB—O2 | 4.0% |
| 3-HHB-1 | 7.0% |
| 3-HHB-3 | 10.0% |
| 3-HB(F)TB-2 | 4.0% |
| 3-HB(F)TB-3 | 4.0% |
| 3-H2BTB-2 | 4.0% |
| 3-H2BTB-3 | 4.0% |
| 3-H2BTB-4 | 4.0% |

$T_{n1}$ = 92.6(° C.)
$\eta$ = 21.4 (mPa · s)
$\Delta n$ = 0.126
$\Delta \epsilon 1$ = 8.9
$V_{th}$ = 1.97(V)

Composition Example 13

| | |
|---|---|
| 3-D2B(F,F)B(F)—OCF3 | 5.0% |
| (Compound No. 98) | |
| 3-DHB(F)—OCF3 | 5.0% |
| (Compound No. 22) | |
| 5-BTB(F)TB-3 | 10.0% |
| V2-HB—TC | 10.0% |
| 3-HB—TC | 10.0% |
| 3-HB—C | 10.0% |
| 5-HB—C | 7.0% |
| 5-BB—C | 3.0% |
| 2-BTB-1 | 10.0% |
| 2-BTB—O1 | 5.0% |
| 3-HH-4 | 5.0% |
| 3-HHB-3 | 11.0% |
| 3-H2BTB-2 | 3.0% |
| 3-H2BTB-3 | 3.0% |
| 3-HB(F)TB-2 | 3.0% |

$T_{n1}$ = 89.4(° C.)
$\eta$ = 18.6 (mPa · s)
$\Delta n$ = 0.201
$\Delta \epsilon 1$ = 8.7
$V_{th}$ = 1.81(V)

Composition Example 14

| | |
|---|---|
| 3-DHB(F,F)—F | 3.0% |
| (Compound No. 21) | |
| 3-D4B—CF3 | 3.0% |
| (Compound No. 261) | |
| 3-DHB(F,F)B(F)—CL | 3.0% |
| (Compound No. 175) | |
| 1V2-BEB(F,F)—C | 6.0% |
| 3-HB—C | 18.0% |
| 2-BTB-1 | 10.0% |
| 5-HH—VFF | 25.0% |
| 1-BHH—VFF | 8.0% |
| 1-BHH-2VFF | 11.0% |
| 3-H2BTB-2 | 5.0% |
| 3-H2BTB-3 | 4.0% |
| 3-HHB-1 | 4.0% |

$T_{n1}$ = 77.6(° C.)
$\eta$ = 15.6 (mPa · s)
$\Delta n$ = 0.125
$\Delta \epsilon 1$ = 7.9
$V_{th}$ = 1.90(V)

Composition Example 15

| | |
|---|---|
| 3-DHB(F,F)—F | 4.0% |
| (Compound No. 21) | |
| 3-D2B—CF3 | 4.0% |
| (Compound No. 11) | |
| 3-DHB(F)—OCF3 | 4.0% |
| (Compound No. 22) | |
| 3-DHB(F,F)B(F)—CL | 4.0% |
| (compound No. 175) | |
| 2-HB—C | 5.0% |
| 3-HB—C | 7.0% |
| 3-HB—O2 | 15.0% |
| 2-BTB-1 | 3.0% |
| 3-HHB-1 | 8.0% |
| 3-HHB—F | 4.0% |
| 3-HHB—O1 | 5.0% |
| 3-HHB-3 | 14.0% |
| 3-HHEB—F | 4.0% |
| 2-HHB(F)—F | 7.0% |
| 3-HHB(F)—F | 7.0% |
| 3-HHB(F,F)—F | 5.0% |

$T_{n1}$ = 86.6(° C.)
$\eta$ = 23.9 (mPa · s)
$\Delta n$ = 0.092
$\Delta \epsilon 1$ = 6.9
$V_{th}$ = 2.12(V)

Composition Example 16

| | |
|---|---|
| 3-D2B-CF3 | 5.0% |
| (Compound No.11) | |
| 3-D4B-CF3 | 5.0% |
| (Compound No.261) | |
| 3-DHB(F, F)-F | 10.0% |
| (Compound No.21) | |
| 3-D2B(F, F)B(F)-OCF3 | 10.0% |
| (Compound No.98) | |
| 3-DHB(F)-OCF3 | 10.0% |
| (Compound No.22) | |
| 3-DHB(F, F)B(F)-CL | 5.0% |
| (Compound No.175) | |
| 2O1-BEB(F)-C | 5.0% |
| 3O1-BEB(F)-C | 12.0% |
| 1V2-BEB(F, F)-C | 7.0% |
| 3-HB-O2 | 10.0% |
| 3-HHB-F | 3.0% |
| 3-HBEB-F | 4.0% |
| 3-HHEB-F | 7.0% |
| 5-HHEB-F | 7.0% |
| $T_{N1}$ = 57.8(° C.) | |
| $\eta$ = 50.4 (mPa.s) | |
| $\Delta n$ = 0.095 | |
| $\Delta \epsilon 1$ = 28.9 | |
| $V_{th}$ = 0.98(V) | |

Composition Example 17

| | |
|---|---|
| 3-D2B(F, F)B(F)-OCF3 | 5.0% |
| (Compound No.98) | |
| 3-DHB(F)-OCF3 | 5.0% |
| (Compound No.22) | |
| 2-HHB(F)-F | 17.0% |
| 3-HHB(F)-F | 17.0% |
| 5-HHB(F)-F | 16.0% |
| 2-H2HB(F)-F | 6.0% |
| 3-H2HB(F)-F | 5.0% |
| 5-H2HB(F)-F | 10.0% |
| 3-HBB(F)-F | 6.0% |
| 5-HBB(F)-F | 13.0% |
| Op-8 | 0.3 part |
| $T_{N1}$ = 98.6(° C.) | |
| $\eta$ = 28.3 (mPa.s) | |
| $\Delta n$ = 0.094 | |
| $\Delta \epsilon 1$ = 6.8 | |
| $V_{th}$ = 1.99(V) | |
| P = 79 $\mu$m | |

Composition Example 18

| | |
|---|---|
| 3-D2B-CF3 | 4.0% |
| (Compound No.11) | |
| 3-DHB(F)-OCF3 | 4.0% |
| (Compound No.22) | |
| 7-HB(F)-F | 3.0% |
| 5-H2B(F)-F | 3.0% |
| 3-HB-O2 | 10.0% |
| 3-HH-4 | 2.0% |
| 3-HH[5D, 6D, 7D]-4 | 3.0% |
| 2-HHB(F)-F | 6.0% |
| 3-HHB(F)-F | 10.0% |
| 5-HH[5D, 6D, 7D]B(F)-F | 10.0% |
| 3-H2HB(F)-F | 5.0% |
| 2-HBB(F)-F | 3.0% |
| 3-HBB(F)-F | 3.0% |

-continued

| | |
|---|---|
| 5-HBB(F)-F | 6.0% |
| 2-H2BB(F)-F | 5.0% |
| 3-H2BB(F)-F | 6.0% |
| 3-HHB-1 | 8.0% |
| 3-HHB-O1 | 5.0% |
| 3-HHB-3 | 4.0% |
| $T_{N1}$ = 88.4(° C.) | |
| $\eta$ = 19.3 (mPa.s) | |
| $\Delta n$ = 0.094 | |
| $\Delta \epsilon 1$ = 4.0 | |
| $V_{th}$ = 2.50(V) | |

Composition Example 19

| | |
|---|---|
| 3-D2B-CF3 | 5.0% |
| (Compound No.11) | |
| 3-D4B-CF3 | 5.0% |
| (Compound No.261) | |
| 3-DHB(F, F)B(F)-CL | 4.0% |
| (Compound No.175) | |
| 7-HB(F, F)-F | 3.0% |
| 3-HB-O2 | 7.0% |
| 3-HHB(F)-F | 10.0% |
| 5-HHB(F)-F | 10.0% |
| 2-HBB(F)-F | 9.0% |
| 3-HBB(F)-F | 9.0% |
| 5-HBB(F)-F | 16.0% |
| 2-HBB-F | 4.0% |
| 3-HBB-F | 4.0% |
| 5-HBB-F | 3.0% |
| 3-HBB(F, F)-F | 5.0% |
| 5-HBB(F, F)-F | 6.0% |
| $T_{N1}$ = 78.8(° C.) | |
| $\eta$ = 24.3 (mPa.s) | |
| $\Delta n$ = 0.111 | |
| $\Delta \epsilon 1$ = 6.6 | |
| $V_{th}$ = 1.90(V) | |

Composition Example 20

| | |
|---|---|
| 3-D2B(F, F)B(F)-OCF3 | 5.0% |
| (Compound No.98) | |
| 3-DHB(F, F)B(F)-CL | 3.0% |
| (Compound No.175) | |
| 7-HB(F, F)-F | 3.0% |
| 3-H2HB(F, F)-F | 12.0% |
| 4-H2HB(F, F)-F | 10.0% |
| 5-H2HB(F, F)-F | 10.0% |
| 3-HHB(F, F)-F | 5.0% |
| 4-HHB(F, F)-F | 5.0% |
| 3-HH2B(F, F)-F | 7.0% |
| 5-HH2B(F, F)-F | 10.0% |
| 3-HBB(F, F)-F | 12.0% |
| 5-HBB(F, F)-F | 12.0% |
| 3-HBCF2OB(F, F)-F | 6.0% |
| $T_{N1}$ = 71.8(° C.) | |
| $\eta$ = 28.9 (mPa.s) | |
| $\Delta n$ = 0.089 | |
| $\Delta \epsilon 1$ = 10.0 | |
| $V_{th}$ = 1.46(V) | |

Composition Example 21

| | |
|---|---|
| 3-D4B-CF3 | 5.0% |
| (Compound No.261) | |
| 3-DHB(F)-OCF3 | 5.0% |
| (Compound No.22) | |
| 3-DHB(F, F)B(F)-CL | 5.0% |
| (Compound No.175) | |
| 7-HB(F, F)-F | 5.0% |
| 3-H2HB(F, F)-F | 12.0% |
| 4-H2HB(F, F)-F | 10.0% |
| 3-HHB(F, F)-F | 10.0% |
| 3-HBB(F, F)-F | 10.0% |
| 3-HHEB(F, F)-F | 10.0% |
| 4-HHEB(F, F)-F | 3.0% |
| 5-HHEB(F, F)-F | 3.0% |
| 2-HBEB(F, F)-F | 3.0% |
| 3-HBEB(F, F)-F | 5.0% |
| 5-HBEB(F, F)-F | 3.0% |
| 3-HDB(F, F)-F | 5.0% |
| 3-HHBB(F, F)-F | 6.0% |

$T_{N1} = 76.6$ (° C.)
$\eta = 36.0$ (mPa.s)
$\Delta n = 0.088$
$\Delta \epsilon 1 = 13.7$
$V_{th} = 1.26$ (V)

Composition Example 22

| | |
|---|---|
| 3-D2B-CF3 | 5.0% |
| (Compound No.11) | |
| 3-DHB(F, F)B(F)-CL | 5.0% |
| (Compound No.175) | |
| 3-HB-CL | 10.0% |
| 5-HB-CL | 4.0% |
| 7-HB-CL | 4.0% |
| 1O1-HH-5 | 5.0% |
| 2-HBB(F)-F | 3.0% |
| 3-HBB(F)-F | 8.0% |
| 5-HBB(F)-F | 14.0% |
| 4-HHB-CL | 8.0% |
| 5-HHB-CL | 3.0% |
| 3-H2HB(F)-CL | 4.0% |
| 3-HBB(F, F)-F | 10.0% |
| 5-H2BB(F, F)-F | 9.0% |
| 3-HB(F)VB-2 | 4.0% |
| 3-HB(F)VB-3 | 4.0% |

$T_{N1} = 87.4$ (° C.)
$\eta = 21.3$ (mPa.s)
$\Delta n = 0.126$
$\Delta \epsilon 1 = 5.9$
$V_{th} = 2.18$ (V)

Composition Example 23

| | |
|---|---|
| 3-D2B(F, F)B(F)-OCF3 | 7.0% |
| (Compound No.98) | |
| 3-D2B-CF3 | 5.0% |
| (Compound No.11) | |
| 3-D4B-CF3 | 5.0% |
| (Compound No.261) | |
| 3-DHB(F)-OCF3 | 8.0% |
| (Compound No.22) | |
| 3-DHB(F, F)B(F)-CL | 5.0% |
| (Compound No.175) | |
| 3-HHB(F, F)-F | 9.0% |
| 3-H2HB(F, F)-F | 8.0% |
| 4-H2HB(F, F)-F | 8.0% |
| 3-HBB(F, F)-F | 13.0% |
| 5-HBB(F, F)-F | 10.0% |
| 3-H2BB(F, F)-F | 10.0% |
| 5-HHBB(F, F)-F | 3.0% |
| 5-HHEBB-F | 2.0% |
| 3-HH2BB(F, F)-F | 3.0% |
| 1O1-HBBH-4 | 4.0% |

$T_{N1} = 82.4$ (° C.)
$\eta = 37.5$ (mPa.s)
$\Delta n = 0.105$
$\Delta \epsilon 1 = 12.2$
$V_{th} = 1.44$ (V)

Composition Example 24

| | |
|---|---|
| 3-D2B(F, F)B(F)-OCF3 | 5.0% |
| (Compound No.98) | |
| 5-HB-F | 12.0% |
| 6-HB-F | 9.0% |
| 7-HB-F | 7.0% |
| 2-HHB-OCF3 | 7.0% |
| 3-HHB-OCF3 | 7.0% |
| 4-HHB-OCF3 | 7.0% |
| 5-HHB-OCF3 | 5.0% |
| 3-HH2B-OCF3 | 4.0% |
| 5-HH2B-OCF3 | 4.0% |
| 3-HHB(F, F)-OCF3 | 5.0% |
| 3-HBB(F)-F | 5.0% |
| 5-HBB(F)-F | 10.0% |
| 3-HH2B(F)-F | 3.0% |
| 3-HB(F)BH-3 | 3.0% |
| 5-HBBH-3 | 3.0% |
| 3-HHB(F, F)-OCF2H | 4.0% |

$T_{N1} = 84.2$ (° C.)
$\eta = 16.5$ (mPa.s)
$\Delta n = 0.090$
$\Delta \epsilon 1 = 5.5$
$V_{th} = 2.25$ (V)

Composition Example 25

| | |
|---|---|
| 3-DHB(F)-OCF3 | 5.0% |
| (Compound No.22) | |
| 3-DHB(F, F)B(F)-CL | 3.0% |
| (Compound No.175) | |
| 5-H4HB(F, F)-F | 7.0% |
| 5-H4HB-OCF3 | 7.0% |
| 3-H4HB(F, F)-CF3 | 8.0% |
| 5-H4HB(F, F)-CF3 | 10.0% |
| 3-HB-CL | 6.0% |
| 5-HB-CL | 4.0% |
| 2-H2BB(F)-F | 5.0% |
| 3-H2BB(F)-F | 10.0% |
| 5-HVHB(F, F)-F | 5.0% |
| 3-HHB-OCF3 | 5.0% |
| 3-H2HB-OCF3 | 5.0% |
| V-HHB(F)-F | |
| 3-HHB(F)-F | 5.0% |
| 5-HHEB-OCF3 | 2.0% |
| 3-HBEB(F, F)-F | 5.0% |

-continued

| | |
|---|---|
| 5-HH-V2F | 3.0% |

$T_{N1} = 70.8(°\text{C.})$
$\eta = 28.1 \text{ (mPa.s)}$
$\Delta n = 0.096$
$\Delta \epsilon_1 = 9.5$
$V_{th} = 1.60(V)$

Composition Example 26

| | |
|---|---|
| 3-D2B(F, F)B(F)-OCF3 | 4.0% |
| (Compound No.98) | |
| 3-D4B-CF3 | 4.0% |
| (Compound No.261) | |
| 3-DHB(F, F)B(F)-CL | 4.0% |
| (Compound No.175) | |
| 2-HHB(F)-F | 2.0% |
| 3-HHB(F)-F | 2.0% |
| 5-HHB(F)-F | 2.0% |
| 2-HBB(F)-F | 6.0% |
| 3-HBB(F)-F | 6.0% |
| 5-HBB(F)-F | 4.0% |
| 2-H2BB(F)-F | 9.0% |
| 3-H2BB(F)-F | 3.0% |
| 3-HBB(F, F)-F | 25.0% |
| 5-HBB(F, F)-F | 19.0% |
| 1O1-HBBH-4 | 5.0% |
| 1O1-HBBH-5 | 5.0% |

$T_{N1} = 91.6(°\text{C.})$
$\eta = 36.5 \text{ (mPa.s)}$
$\Delta n = 0.129$
$\Delta \epsilon_1 = 9.0$
$V_{th} = 1.67(V)$

Composition Example 27

| | |
|---|---|
| 3-D2B(F, F)B(F)-OCF3 | 3.0% |
| (Compound No.98) | |
| 3-D2B-CF3 | 3.0% |
| (Compound No.11) | |
| 3-DHB(F)-OCF3 | 3.0% |
| (Compound No.22) | |
| 5-HB-CL | 8.0% |
| 3-HH-4 | 7.0% |
| 3-HB-O2 | 20.0% |
| 3-H2HB(F, F)-F | 8.0% |
| 3-HHB(F, F)-F | 8.0% |
| 3-HBB(F, F)-F | 6.0% |
| 3-HHB(F)-F | 5.0% |
| 5-HHB(F)-F | 5.0% |
| 2-H2HB(F)-F | 2.0% |
| 3-H2HB(F)-F | 1.0% |
| 5-H2HB(F)-F | 2.0% |
| 3-HHBB(F, F)-F | 4.0% |
| 3-HBCF2OB-OCF3 | 4.0% |
| 5-HBCF2OB(F, F)-CF3 | 4.0% |
| 3-HHB-1 | 3.0% |
| 3-HHB-O1 | 4.0% |

$T_{N1} = 69.5(°\text{C.})$
$\eta = 18.0 \text{ (mPa.s)}$
$\Delta n = 0.084$
$\Delta \epsilon_1 = 5.4$
$V_{th} = 2.03(V)$

Composition Example 28

| | |
|---|---|
| 3-D2B(F, F)B(F)-OCF3 | 5.0% |
| (Compound No.98) | |
| 3-BEB(F)-C | 8.0% |
| 3-HB-C | 8.0% |
| V-HB-C | 8.0% |
| 1V-HB-C | 8.0% |
| 3-HB-O2 | 3.0% |
| 3-HH-2V | 14.0% |
| 3-HH-2V1 | 7.0% |
| V2-HHB-1 | 15.0% |
| 3-HHB-1 | 5.0% |
| 3-HHEB-F | 7.0% |
| 3-H2BTB-2 | 6.0% |
| 3-H2BTB-3 | 6.0% |

$T_{N1} = 91.9(°\text{C.})$
$\eta = 18.7 \text{ (mPa.s)}$
$\Delta n = 0.126$
$\Delta \epsilon_1 = 9.6$
$V_{th} = 1.98(V)$

Composition Example 29

| | |
|---|---|
| 3-D4B-CF3 | 4.0% |
| (Compound No.261) | |
| 3-DHB(F)-OCF3 | 5.0% |
| (Compound No.22) | |
| 3-DHB(F, F)B(F)-CL | 3.0% |
| (Compound No.175) | |
| 3-H2HB(F, F)-F | 7.0% |
| 5-H2HB(F, F)-F | 8.0% |
| 3-HHB(F, F)-F | 10.0% |
| 3-HH2B(F, F)-F | 9.0% |
| 5-HH2B(F, F)-F | 9.0% |
| 3-HBB(F, F)-F | 15.0% |
| 5-HBB(F, F)-F | 10.0% |
| 4-HBEB(F, F)-F | 2.0% |
| 5-HBEB(F, F)-F | 2.0% |
| 3-HHEB(F, F)-F | 10.0% |
| 4-HHEB(F, F)-F | 3.0% |
| 5-HHEB(F, F)-F | 3.0% |

$T_{N1} = 79.3(°\text{C.})$
$\eta = 33.4 \text{ (mPa.s)}$
$\Delta n = 0.090$
$\Delta \epsilon_1 = 12.0$
$V_{th} = 1.65(V)$

Composition Example 30

| | |
|---|---|
| 2-DH2B(F)-F | 5.0% |
| (Compound No.51) | |
| 2-D2BEB-CL | 5.0% |
| (Compound No.311) | |
| 2-HHB(F)-F | 17.0% |
| 3-HHB(F)-F | 17.0% |
| 5-HHB(F)-F | 16.0% |
| 3-H2HB(F)-F | 5.0% |
| 5-H2HB(F)-F | 10.0% |
| 2-HBB(F)-F | 6.0% |
| 3-HBB(F)-F | 6.0% |
| 5-HBB(F)-F | 13.0% |

Composition Example 31

| | |
|---|---|
| 2-HD2B(F)-CF3 | 5.0% |
| (Compound No.46) | |
| 3-D2B(F)CF2OB(F)-CF3 | 5.0% |
| (Compound No.317) | |
| 7-HB(F)-F | 5.0% |
| 5-H2B(F)-F | 5.0% |
| 3-HB-O2 | 10.0% |
| 3-HH-4 | 2.0% |
| 3-HH[5D, 6D, 7D]-4 | 3.0% |
| 3-HHB(F)-F | 10.0% |
| 5-HH[5D, 6D, 7D]B(F)-F | 10.0% |
| 3-H2HB(F)-F | 5.0% |
| 2-HBB(F)-F | 3.0% |
| 3-HBB(F)-F | 3.0% |
| 5-HBB(F)-F | 6.0% |
| 2-H2BB(F)-F | 5.0% |
| 3-H2BB(F)-F | 6.0% |
| 3-HHB-1 | 8.0% |
| 3-HHB-O1 | 5.0% |
| 3-HHB-3 | 4.0% |

Composition Example 32

| | |
|---|---|
| 2-DH2B(F)-F | 5.0% |
| (Compound No.51) | |
| 3-D2HB(CL)-OCF2H | 5.0% |
| (Compound No.40) | |
| 7-HB(F, F)-F | 3.0% |
| 3-HB-O2 | 7.0% |
| 2-HHB(F)-F | 10.0% |
| 3-HHB(F)-F | 10.0% |
| 5-HHB(F)-F | 10.0% |
| 2-HBB(F)-F | 9.0% |
| 3-HBB(F)-F | 9.0% |
| 5-HBB(F)-F | 16.0% |
| 2-HBB-F | 4.0% |
| 3-HBB-F | 4.0% |
| 5-HBB-F | 3.0% |
| 3-HBB(F, F)-F | 3.0% |

Composition Example 33

| | |
|---|---|
| 2-HD2B(F)-CF3 | 5.0% |
| (Compound No.46) | |
| 2-D2BEB-CL | 5.0% |
| (Compound No.311) | |
| 3-D2HB(CL)-OCF2H | 5.0% |
| (Compound No.40) | |
| 7-HB(F, F)-F | 3.0% |
| 3-H2HB(F, F)-F | 12.0% |
| 4-H2HB(F, F)-F | 10.0% |
| 3-HHB(F, F)-F | 5.0% |
| 4-HHB(F, F)-F | 5.0% |
| 3-HH2B(F, F)-F | 15.0% |
| 5-HH2B(F, F)-F | 10.0% |
| 3-HBB(F, F)-F | 12.0% |
| 5-HBB(F, F)-F | 7.0% |
| 3-HBCF2OB(F, F)-F | 6.0% |

Composition Example 34

| | |
|---|---|
| 3-D2B(F)-CF2OB(F)-CF3 | 5.0% |
| (Compound No.317) | |
| 1-HD2B(F)B(F, F)-OCF2CFHCF3 | 3.0% |
| (Compound No.236) | |
| 7-HB(F, F)-F | 5.0% |
| 3-H2HB(F, F)-F | 12.0% |
| 4-H2HB(F, F)-F | 10.0% |
| 3-HHB(F, F)-F | 10.0% |
| 4-HHB(F, F)-F | 5.0% |
| 3-HHB(F, F)-F | 10.0% |
| 3-HHEB(F, F)-F | 10.0% |
| 4-HHEB(F, F)-F | 3.0% |
| 5-HHEB(F, F)-F | 3.0% |
| 2-HBEB(F, F)-F | 3.0% |
| 3-HBEB(F, F)-F | 5.0% |
| 5-HBEB(F, F)-F | 3.0% |
| 3-HDB(F, F)-F | 10.0% |
| 3-HHBB(F, F)-F | 3.0% |

Composition Example 35

| | |
|---|---|
| 2-DH2B(F)-F | 5.0% |
| (Compound No.51) | |
| 3-HB-CL | 10.0% |
| 5-HB-CL | 4.0% |
| 7-HB-CL | 4.0% |
| 1O1-HH-5 | 5.0% |
| 2-HBB(F)-F | 8.0% |
| 3-HBB(F)-F | 8.0% |
| 5-HBB(F)-F | 9.0% |
| 4-HHB-CL | 8.0% |
| 5-HHB-CL | 8.0% |
| 3-H2HB(F)-CL | 4.0% |
| 3-HBB(F, F)-F | 10.0% |
| 5-H2BB(F, F)-F | 9.0% |
| 3-HB(F)VB-2 | 4.0% |
| 3-HB (F)VB-3 | 4.0% |

Composition Example 36

| | |
|---|---|
| 2-HD2B(F)-CF3 | 4.0% |
| (Compound No. 46) | |
| 1-HD2B(F)B(F, F)-OCF2CFHCF3 | 3.0% |
| (Compound No. 236) | |
| 3-D2B(F, F)B(F)B(F)-OCF2H | 3.0% |
| (Compound No. 228) | |
| 3-HHB(F, F)-F | 9.0% |
| 3-H2HB(F, F)-F | 8.0% |
| 4-H2HB(F, F)-F | 8.0% |
| 5-H2HB(F, F)-F | 4.0% |
| 3-HBB(F, F)-F | 19.0% |
| 5-HBB(F, F)-F | 20.0% |
| 3-H2BB(F, F)-F | 10.0% |
| 5-HHBB(F, F)-F | 3.0% |
| 5-HHEBB-F | 2.0% |
| 3-HH2BB(F, F)-F | 3.0% |
| 1O1-HBBH-5 | 4.0% |

Composition Example 37

| | |
|---|---|
| 3-D2B(F)-CF2OB(F)-CF3 (Compound No. 317) | 5.0% |
| 3-D2HB(CL)-OCF2H (Compound No. 40) | 5.0% |
| 5-HB-F | 12.0% |
| 6-HB-F | 9.0% |
| 7-HB-F | 7.0% |
| 2-HHB-OCF3 | 7.0% |
| 3-HHB-OCF3 | 7.0% |
| 4-HHB-OCF3 | 7.0% |
| 5-HHB-OCF3 | 5.0% |
| 3-HH2B-OCF3 | 4.0% |
| 5-HH2B-OCF3 | 4.0% |
| 3-HHB(F, F)-OCF3 | 5.0% |
| 3-HBB(F)-F | 10.0% |
| 3-HH2B(F)-F | 3.0% |
| 3-HB(F)BH-3 | 3.0% |
| 5-HBBH-3 | 3.0% |
| 3-HHB(F, F)-OCF2H | 4.0% |

Composition Example 38

| | |
|---|---|
| 2-DH2B(F)-F (Compound No. 51) | 5.0% |
| 2-HD2B(F)-CF3 (Compound No. 46) | 5.0% |
| 2-D2BEB-CL (Compound No. 311) | 5.0% |
| 3-D2B(F)CF2OB(F)-CF3 (Compound No. 317) | 5.0% |
| 3-D2HB(CL)-OCF2H (Compound No. 40) | 5.0% |
| 1-HD2B(F)B(F, F)-OCF2CFHCF3 (Compound No. 236) | 3.0% |
| 3-D2B(F, F)B(F)B(F)-OCF2H (Compound No. 228) | 3.0% |
| 2-HHB(F)-F | 2.0% |
| 3-HHB(F)-F | 2.0% |
| 5-HHB(F)-F | 2.0% |
| 3-HBB(F)-F | 6.0% |
| 5-HBB(F)-F | 10.0% |
| 3-H2BB(F)-F | 9.0% |
| 3-HBB(F, F)-F | 20.0% |
| 5-HBB(F, F)-F | 14.0% |
| 1O1-HBBH-5 | 4.0% |

Composition Example 39

| | |
|---|---|
| 3-D2B-CF3 (Compound No. 11) | 5.0% |
| 3-D4B-CF3 (Compound No. 261) | 5.0% |
| 3-DHB(F)-OCF3 (Compound No. 22) | 8.0% |
| 2-HHB(F)-F | 11.0% |
| 3-HHB(F)-F | 11.0% |
| 5-HHB(F)-F | 10.0% |
| 2-H2HB(F)-F | 10.0% |
| 3-H2HB(F)-F | 5.0% |
| 5-H2HB(F)-F | 10.0% |
| 2-HBB(F)-F | 6.0% |
| 3-HBB(F)-F | 6.0% |
| 5-HBB(F)-F | 13.0% |

$T_{N1} = 77.3 (°C)$
$\eta = 27.8 \text{ (mPa.s)}$
$\Delta n = 0.085$
$\Delta \epsilon 1 = 6.6$
$V_{th} = 1.86(V)$

Composition Example 40

| | |
|---|---|
| 3-DHB(F)-OCF3 (Compound No. 22) | 6.0% |
| 3-DHB(F, F)B(F)-Cl (Compound No. 175) | 10.0% |
| 7-HB(F, F)-F | 3.0% |
| 3-HB-O2 | 7.0% |
| 2-HHB(F)-F | 8.0% |
| 3-HHB(F)-F | 8.0% |
| 5-HHB(F)-F | 8.0% |
| 2-HBB(F)-F | 8.0% |
| 3-HBB(F)-F | 8.0% |
| 5-HBB(F)-F | 8.0% |
| 2-HBB-F | 4.0% |
| 3-HBB-F | 4.0% |
| 5-HBB-F | 3.0% |
| 3-HBB(F, F)-F | 5.0% |
| 5-HBB(F, F)-F | 10.0% |

$T_{N1} = 89.2 (°C)$
$\eta = 35.8 \text{ (mPa.s)}$
$\Delta n = 0.119$
$\Delta \epsilon 1 = 9.0$
$V_{th} = 1.79(V)$

Composition Example 41

| | |
|---|---|
| 3-D2B-CF3 (Compound No. 11) | 3.0% |
| 3-D4B-CF3 (Compound No. 261) | 3.0% |
| 3-DHB(F, F)B(F)-Cl (Compound No. 175) | 9.0% |
| 3-HB-CL | 6.0% |
| 5-HB-CL | 4.0% |
| 7-HB-CL | 4.0% |
| 1O1-HH-5 | 5.0% |
| 2-HBB(F)-F | 7.0% |
| 3-HBB(F)-F | 7.0% |
| 5-HBB(F)-F | 7.0% |
| 4-HHB-CL | 8.0% |
| 5-HHB-CL | 8.0% |
| 3-H2HB(F)-CL | 4.0% |
| 3-HBB(F, F)-F | 8.0% |
| 5-H2BB(F, F)-F | 9.0% |
| 3-HB(F)VB-2 | 4.0% |
| 3-HB(F)VB-3 | 4.0% |

$T_{N1} = 90.3 (°C)$
$\eta = 33.1 \text{ (mPa.s)}$
$\Delta n = 0.127$
$\Delta \epsilon 1 = 6.9$
$V_{th} = 2.12(V)$

Composition Example 42

| | |
|---|---|
| 3-D2B-CF3 (Compound No. 11) | 5.0% |
| 3-D4B-CF3 (Compound No. 261) | 5.0% |
| 3-DHB(F)-OCF3 (Compound No. 22) | 10.0% |
| 3-DHB(F, F)B(F)-Cl (Compound No. 175) | 10.0% |
| 3-HBB(F, F)-F | 9.0% |
| 3-H2HB(F, F)-F | 6.0% |
| 4-H2HB(F, F)-F | 6.0% |
| 5-H2HB(F, F)-F | 6.0% |
| 3-HBB(F, F)-F | 11.0% |
| 5-HBB(F, F)-F | 8.0% |
| 3-H2BB(F, F)-F | 8.0% |
| 5-HHBB(F, F)-F | 3.0% |
| 5-HHEBB-F | 2.0% |
| 3-HH2BB(F, F)-F | 3.0% |
| 1O1-HBBH-4 | 4.0% |

-continued

| | |
|---|---|
| 1O1-HBBH-5 | 4.0% |
| $T_{N1}$ = 93.6(° C.) | |
| $\eta$ = 44.1 (mPa.s) | |
| $\Delta n$ = 0.112 | |
| $\Delta \epsilon 1$ = 12.3 | |
| $V_{th}$ = 1.57(V) | |

Composition Example 43

| | |
|---|---|
| 3-D2B-CF3(Compound No. 11) | 5.0% |
| 3-D4B-CF3(Compound No. 261) | 5.0% |
| 3-DHB(F)-OCF3 (Compound No. 22) | 12.0% |
| 5-HB-F | 7.0% |
| 6-HB-F | 4.0% |
| 7-HB-F | 7.0% |
| 2-HHB-OCF3 | 7.0% |
| 3-HHB-OCF3 | 7.0% |
| 3-HH2B-OCF3 | 4.0% |
| 5-HH2B-OCF3 | 4.0% |
| 3-HHB(F, F)-OCF3 | 5.0% |
| 3-HBB(F)-F | 10.0% |
| 5-HBB(F)-F | 10.0% |
| 3-HH2B(F)-F | 3.0% |
| 3-HB(F)BH-3 | 3.0% |
| 5-HBBH-3 | 3.0% |
| 3-HHB(F, F)-OCF2H | 4.0% |
| $T_{N1}$ = 65.0(° C.) | |
| $\eta$ = 21.5 (mPa.s) | |
| $\Delta n$ = 0.089 | |
| $\Delta \epsilon 1$ = 7.2 | |
| $V_{th}$ = 1.67(V) | |

Composition Example 44

| | |
|---|---|
| 3-DHB(F)-OCF3 (Compound No. 22) | 10.0% |
| 3-DHB(F, F)B(F)-Cl (Compound No. 175) | 5.0% |
| 2-HHB(F)-F | 2.0% |
| 3-HHB(F)-F | 2.0% |
| 5-HHB(F)-F | 2.0% |
| 2-HBB(F)-F | 6.0% |
| 3-HBB(F)-F | 6.0% |
| 5-HBB(F)-F | 10.0% |
| 2-H2BB(F)-F | 9.0% |
| 3-H2BB(F)-F | 9.0% |
| 3-HBB(F, F)-F | 15.0% |
| 5-HBB(F, F)-F | 19.0% |
| 1O1-HBBH-4 | 5.0% |
| $T_{N1}$ = 91.1(° C.) | |
| $\eta$ = 39.8 (mPa.s) | |
| $\Delta n$ = 0.130 | |
| $\Delta \epsilon 1$ = 9.4 | |
| $V_{th}$ = 1.75(V) | |

Composition Example 45

| | |
|---|---|
| 3-DHB(F)-OCF3 (Compound No. 22) | 15.0% |
| 3-H2HB(F, F)-F | 7.0% |
| 5-H2HB(F, F)-F | 8.0% |
| 3-HHB(F, F)-F | 10.0% |
| 4-HHB(F, F)-F | 5.0% |
| 3-HH2B(F, F)-F | 9.0% |
| 5-HH2B(F, F)-F | 9.0% |
| 3-HBB(F, F)-F | 15.0% |
| 3-HBEB(F, F)-F | 2.0% |
| 4-HBEB(F, F)-F | 2.0% |
| 5-HBEB(F, F)-F | 2.0% |
| 3-HHEB(F, F)-F | 10.0% |
| 4-HHEB(F, F)-F | 3.0% |
| 5-HHEB(F, F)-F | 3.0% |
| $T_{N1}$ = 81.0(° C.) | |
| $\eta$ = 33.4 (mPa.s) | |
| $\Delta n$ = 0.086 | |
| $\Delta \epsilon 1$ = 12.4 | |
| $V_{th}$ = 1.69(V) | |

Composition Example 46

| | |
|---|---|
| 3-DHB(F)-OCF3 (Compound No. 22) | 10.0% |
| 1V2-BEB(F, F)-C | 5.0% |
| 3-HB-C | 15.0% |
| 1-BTB-3 | 5.0% |
| 2-BTB-1 | 10.0% |
| 3-HH-4 | 11.0% |
| 3-HHB-1 | 11.0% |
| 3-HHB-3 | 9.0% |
| 3-H2BTB-2 | 4.0% |
| 3-H2BTB-3 | 4.0% |
| 3-H2BTB-4 | 4.0% |
| 3-HB(F)TB-2 | 6.0% |
| 3-HB(F)TB-3 | 6.0% |
| $T_{N1}$ = 90.7(° C.) | |
| $\eta$ = 23.1 (mPa.s) | |
| $\Delta n$ = 0.161 | |
| $\Delta \epsilon 1$ = 9.4 | |
| $V_{th}$ = 1.83(V) | |

Composition Example 47

| | |
|---|---|
| 3-D2B-CF3(Compound No. 11) | 5.0% |
| 3-D4B-CF3 (Compound No. 261) | 5.0% |
| 3-DHB(F)-OCF3 (Compound No. 22) | 4.0% |
| 3-O1-BEB(F)-C | 12.0% |
| 1V2-BEB(F, F)-C | 16.0% |
| 3-HB-O2 | 5.0% |
| 3-HH-4 | 3.0% |
| 3-HHB-F | 3.0% |
| 3-HHB-1 | 8.0% |
| 3-HHB-O1 | 4.0% |
| 3-HBEB-F | 4.0% |
| 3-HHEB-F | 7.0% |
| 5-HHEB-F | 7.0% |
| 3-H2BTB-2 | 4.0% |
| 3-H2BTB-3 | 4.0% |
| 3-H2BTB-4 | 4.0% |
| 3-HB(F)TB-2 | 5.0% |
| $T_{N1}$ = 80.6(° C.) | |
| $\eta$ = 39.6 (mPa.s) | |
| $\Delta n$ = 0.131 | |
| $\Delta \epsilon 1$ = 26.8 | |
| $V_{th}$ = 1.03(V) | |

Composition Example 48

| | |
|---|---|
| 3-D2B-CF3(Compound No. 11) | 5.0% |
| 3-DHB(F, F)B(F)-Cl (Compound No. 175) | 7.0% |
| 2-HB-C | 5.0% |
| 3-HB-C | 12.0% |
| 3-HB-O2 | 10.0% |
| 2-BTB-1 | 3.0% |
| 3-HHB-1 | 8.0% |
| 3-HHB-F | 4.0% |
| 3-HHB-O1 | 5.0% |
| 3-HHB-3 | 14.0% |
| 3-HHEB-F | 4.0% |
| 5-HHEB-F | 4.0% |
| 2-HHB(F)-F | 7.0% |
| 3-HHB(F)-F | 7.0% |
| 3-HHB(F, F)-F | 5.0% |

$T_{N1} = 96.8(° C.)$
$\eta = 25.7$ (mPa.s)
$\Delta n = 0.097$
$\Delta \epsilon 1 = 7.0$
$V_{th} = 1.98(V)$

Composition Example 49

| | |
|---|---|
| 3-DHB(F)-OCF3 (Compound No. 22) | 4.0% |
| 3-DHB(F, F)B(F)-Cl (Compound No. 175) | 5.0% |
| 3-BEB(F)-C | 8.0% |
| 3-HB-C | 4.0% |
| V-HB-C | 8.0% |
| 1V-HB-C | 8.0% |
| 3-HB-O2 | 3.0% |
| 3-HH-2V | 14.0% |
| 3-HH-2V1 | 7.0% |
| V2-HHB-1 | 15.0% |
| 3-HHB-1 | 5.0% |
| 3-HHEB-F | 7.0% |
| 3-H2BTB-2 | 6.0% |
| 3-H2BTB-3 | 6.0% |

$T_{N1} = 98.7(° C.)$
$\eta = 22.0$ (mPa.s)
$\Delta n = 0.128$
$\Delta \epsilon 1 = 10.0$
$V_{th} = 2.06(V)$

Description of the Preferred Embodiments

The following examples illustrate the present invention more specifically. In each example, C represents a crystal, S×1 and S×2, each independently, represent a smectic phase different each other, N represents a Nematic phase, and I represents a isotropic liquid phase.

EXAMPLE 1

Production of the compound (No. 21), 5-propyl-2-(4-(3, 4,5trifluorophenyl)-cyclohexyl)-1,3-dioxane (in formula (1), R=n-propyl group, n1=n2=0, A=(a), Za=Zb=a single bond, $Q_1=Q_2=$a fluorine atom, Y=a fluorine atom)

1st Step

To Grignard reagent prepared from 3,4,5-trifluorobromobenzene 100 g (474 mmol) and magnesium in 360 ml of dried tetrahydrofuran (abbreviated as THF, hereinafter) at room temperature, a THF (500 ml) solution of cyclohexanedione monoethyleneketal 74.0 g (474 mmol) was added dropwise at room temperature, and the mixture was stirred for 5 hours at room temperature. The reactant was added to one liter of 6N-hydrochloric acid, and the product was extracted with diethylether. The extract was washed with water, a saturated sodium bicarbonate aqueous solution, and then water, and dried over anhydrous magnesium sulfate, and the solvent was distilled off under reduced pressure. To the residue, para-toluene sulfonic acid (abbreviated as PTS, hereinafter) 5 g and toluene 600 ml were added. The mixture was refluxed with heating for 3 hours while removing water formed with Dien-Stark. The reactant was washed with water, a saturated sodium bicarbonate aqueous solution, and then water, and dried over anhydrous magnesium sulfate, and the solvent was distilled off under reduced pressure. The residue was purified by silica gel column chromatography (eluent: heptane/ethyl acetate=4/1). Such obtained purified material was hydrogenated in the presence of 5% palladium carbon 5 g as a catalyst in ethanol 300 ml. The catalyst was filtered off, the solvent was distilled off, and the residue was purified by silica gel column chromatography (eluent: heptane/ethyl acetate=3/1) to obtain 4-(3,4,5trifluorophenyl) cyclohexanone 52 g (228 mmol). The yield was 48.1% from 3,4,5-trifluorobromobenzene.

2nd Step

To dried methoxymethyltriphenylphosphonium chloride (abbreviated as MTP, hereinafter) 25 g (72.9 mmol), THF 300 ml was added, and potassium-t-butoxide 8.2 g (73.1 mmol) was added. The mixture was stirred for about one hour. To the reactant, a THF solution (150 ml) of the above 4-(3,4,5-trifluorophenyl)cyclohexanone 14.8 g (64.9 mmol) was added dropwise, and the mixture was stirred for 2 hours. Water 300 ml was added to the reactant, the product was extracted with toluene. The extract was washed with a sodium chloride aqueous solution, dried over anhydrous magnesium sulfate, and the solvent was distilled off. The residue was purified by silica gel column chromatography (eluent: toluene). The resulting purified material was stirred in mixture solvent of 3N-hydrochloric acid 200 ml and THF 200 ml for 5 hours, and the product was extracted with toluene. The extract was washed with a saturated sodium bicarbonate aqueous solution and then with water, and dried over anhydrous magnesium sulfate. Toluene was distilled off to obtain 4-(3,4,5-trifluorophenyl) cyclohexanecarboaldehyde 10.5 g (43.3 mmol). The yield was 66.7% from 4-(3,4,5-trifluorophenyl) cyclohexanone.

3rd Step 2-propyl-1,3-propanediol 5.2 g (44.0 mol) and 4(3,4,5-trifluoro phenyl) cyclohexanecarboaldehyde 10.5 g (43.3 mmol) were dissolved in toluene 100 ml, and PTS 1 g was added, and the mixture was refluxed with heating for 3 hours while removing water formed with Dien-Stark. The reactant was washed with a saturated sodium bicarbonate aqueous solution, and then with saturated sodium chloride aqueous solution, and dried over anhydrous magnesium sulfate, and the solvent was distilled off. The residue was recrystallized twice from heptane to obtain 5-propyl-2-(4-(3,4,5-trifluorophenyl)cyclohexyl-1,3-dioxane 2.0 g (5.8 mmol). The yield was 13% from 4-(3,4,5-trifluorophenyl) cyclohexane carboaldehyde.

$^1$H-NMR(CDCl$_3$) δ(ppm): 6.88–6.71 (m,2H), 4.23–4.00(m,3H), 3.42–3.17(m,2H), 2.48–0.82(m, 18H)

C-I point 92.8° C.

EXAMPLE 2

Production of the compound (No. 98), 5-propyl-2-(2-(4-(3-fluoro-4-trifluoromethoxyphenyl)-3,5-difluorophenyl)

ethyl)-1,3-dioxane (in general formula (1), R=n-propyl group, n1=0, n2=1, A=(b), Za=Zb=a single bond, ring A1=3,5-difluoro-1,4-phenylene, $Q_1$=a fluorine atom, $Q_2$=a hydrogen atom, Y=a trifluoromethoxy group)

1st Step

Dimethoxyethane 350 ml was added to 60% sodium hydride 14.4 g (360 mmol), the mixture was stirred at room temperature while a solution of ethyl diethylphosphonoacetate 80.7 g (360 mmol) in dimethoxyethane (50 ml) was added dropwise. After the generation of hydrogen gas was stopped, the solution was cooled to 15° C., and a solution of 3,5-difluorobenzaldehyde 50.0 g (352 mmol) in dimethoxyethane (50 ml) was added dropwise keeping the liquid temperature below 25° C. After addition, the mixture was stirred for 30 minutes, the reactant was added to water 300 ml, and the product was extracted with diethylether. The extract was washed with a sodium chloride aqueous solution, and dried over anhydrous magnesium sulfate, and the solvent was distilled off under reduced pressure. The residue was purified by silica gel column chromatography (eluent: heptane/ethyl acetate=3/1). Such obtained purified material was hydrogenated in the presence of 5% palladium carbon as a catalyst in ethanol 300 ml. After hydrogenation, the catalyst was filtered off, the solvent was distilled off under reduced pressure to obtain 3-(3,5-difluorophenyl) propionic acid ethyl ester 53.0 g (247 mmol). The yield was 70.2% from 3,5-difluorobenzaldehyde.

2nd Step

The above 3-(3,5-difluorophenyl)propionic ethyl ester 53.0 g (247 mmol) was dissolved in toluene 500 ml and cooled to −58° C. under stirring, and a 1.01 M of toluene solution 255 ml (258 mmol) of DIBAL was added dropwise, and the mixture was stirred at −55° C. for 15 minutes. At the same temperature, a saturated ammonium chloride aqueous solution 200 ml was added dropwise to the reactant, and the mixture was heated to room temperature and stirred for 30 minutes. Diethyl ether 100 ml was added to the reactant, and the mixture was stirred at room temperature for one hour, and magnesium sulfate was added, and the suspension was filtered with cerite. The filtrate was washed with water, the organic layer was dried over magnesium sulfate, and the solvent was distilled off under reduced pressure to obtain 3(3,5-difluorophenyl)propanal 41.5 g. The yield was 98.8% from 3-(3,5-difluorophenyl)propionic acid ethyl ester.

3rd Step

2-Propyl-1,3-propanediol 22.0 g (186 mol) and the above 3-(3,5difluorophenyl)propanal 30.0 g (176 mmol) were dissolved in toluene 300 ml, and PTS 1 g was added, and the mixture was refluxed with heating for 3 hours while removing water formed with Dien-Stark. The reactant was washed with a saturated sodium bicarbonate aqueous solution, and then with saturated sodium chloride aqueous solution, and dried over anhydrous magnesium sulfate, and the solvent was distilled off. The residue was recrystallized twice from heptane to obtain 5-propyl-2-(4-(3,5-difluorophenyl)ethyl)-1,3-dioxane 7.50 g (27.7 mmol). The yield was 15.7% from 3-(3,5-difluorophenyl)propanal.

4th Step

The above 5-propyl-2-(4(3,5-difluorophenyl)ethyl)-1,3-dioxane 7.50 g (27.7 mmol) was dissolved in THF 70 ml, and cooled to −60° C. under a nitrogen atmosphere. To this solution, 1.60 M hexane solution 21.0 ml (33.6 mmol) of n-butyllithium was added dropwise keeping the liquid temperature below −50° C., and the mixture was stirred for one hour at the same temperature. Then, to the reactant, 0.5 M THF solution 67.2 ml (33.6 mmol) of zinc chloride was added dropwise keeping the liquid temperature below −50° C., and the mixture was heated to room temperature and stirred for 30 minutes. Tetrakistriphenyl phosphin paradium 0.5 g and 3-fluoro-4-trifluoromethoxybromobenzene 8.70 g (33.6 mmol) were added to the solution, and the mixture was refluxed with heating for 3 hours. Water 100 ml was added to the resulting reactant, and the product was extracted with toluene. The extract was washed with 3N-hydrochloric acid, a saturated bicarbonate aqueous solution and then a saturated sodium chloride aqueous solution, and dried over magnesium sulfate, and the solvent was distilled off The residue was purified by silica gel column chromatography (eluent: toluene), and recrystallized twice from a mixed solvent of heptane/ethyl acetate=1/1 to obtain 5-propyl-2-(2-(4-(3-fluoro-4-trifluoromethoxyphenyl)-3,5-difluorophenyl)ethyl)-1,3-dioxane 1.60 g (3.57 mmol). The yield was 12.9% from 5-propyl-2-(4-(3,5-difluorophenyl) ethyl)-1,3-dioxane.

$^1$H-NMR(CDCl$_3$) δ(ppm): 7.45–7.24 (m,3H), 6.90–6.80(m,2H), 4.46(t,1H), 4.19–4.01(m,2H), 3.44–3.19(m,2H), 2.85–2.16(m,2H), 1.28–0.82(m,9H)

C-I point 57.8° C.

EXAMPLE 3

Production of the compound (No. 22), 5-propyl-2-(4-(3-fluoro-4-trifluoro methoxyphenyl)cyclohexyl)-1,3-dioxane (in formula (1), R=n-propyl group, n1=n2=0, A=(a), Za=Zb=a single bond, $Q_1$=a fluorine atom, $Q_2$=a hydrogen atom, Y=a trifluoromethoxy group)

1st Step

To Grignard reagent prepared from 3-fluoro-4-trifluoromethoxy bromobenzene 70.0 g (270 mmol) and magnesium in dried THF 300 ml at room temperature, a THF (200 ml) solution of cyclohexanedione monoethyleneketal 42.1 g (270 mmol) was added dropwise at room temperature, and the mixture was stirred for 3 hours at room temperature. The reactant was added to one liter of 6N-hydrochloric acid, and the product was extracted with diethylether. The extract was washed with water, a saturated sodium bicarbonate aqueous solution, and then water, and dried over anhydrous magnesium sulfate, and the solvent was distilled off under reduced pressure. To the residue, para-toluene sulfonic acid 5 g and toluene 500 ml were added. The mixture was refluxed with heating for 3 hours while removing water formed with Dien-Stark. The reactant was washed with water, a saturated sodium bicarbonate aqueous solution, and then water, and dried over anhydrous magnesium sulfate, and the solvent was distilled off under reduced pressure. The residue was purified by silica gel column chromatography (eluent: heptane/ethyl acetate=4/1). Such obtained purified material was hydrogenated in the presence of 5% palladium carbon 5 g as a catalyst in ethanol 300 ml. The catalyst was filtered off, the solvent was distilled off under reduced pressure, formic acid 20 g and toluene 200 ml were added to the residue, and the mixture was refluxed for 3 hours. After cooling, water 300 ml was added to the reactant, and the organic layer was fractionated, washed with water, a saturated sodium bicarbonate solution, and then water, and dried over anhydrous magnesium sulfate, and the solvent was distilled off. The residue was purified by silica gel column chromatography (eluent: heptane/ethyl acetate=3/1) to obtain 4-(3-fluoro-4-trifluoromethoxyphenyl)cyclohexanone 22.0 g (84.5 mmol). The yield was 31.3% from 3-fluoro-4-trifluoromethoxybromobenzene.

2nd Step

To dried MTP 10.0 g (29.2 mmol), THF 100 ml was added, and potassium-t-butoxide 3.30 g (29.4 mmol) was added. The mixture was stirred for about one hour. To the reactant, a Th solution (50 ml) of the above 4-(3-fluoro-4-trifluoromethoxyphenyl)cyclohexanone 6.0 g (23.1 mmol) was added dropwise, and the mixture was stirred for 2 hours. Water 150 ml was added to the reactant, the product was extracted with diethylether. The extract was washed with a sodium chloride aqueous solution, dried over anhydrous magnesium sulfate, and the solvent was distilled off. The residue was purified by silica gel column chromatography (eluent: toluene). The resulting purified material was stirred in mixture solvent of 3N-hydrochloric add 200 ml and acetone 200 ml for 5 hours, and the product was extracted with toluene. The extract was washed with a saturated sodium bicarbonate aqueous solution and then with water, and dried over anhydrous magnesium sulfate. Toluene was distilled off to obtain 4(3-fluoro-4-trifluoromethoxyphenyl) cyclohexanecarboaldehyde 3.6 g (13.3 mmol). The yield was 57.6% from 4-(3-fluoromethoxy phenyl) cyclohexanone.

3rd Step

2-Propyl-1,3-propanediol 2.2 g (18.5 mol) and 4-(3-fluoro-4-trifluoromethoxyphenyl) cyclohexanecarboaldehyde 3.6 g (13.3 mmol) were dissolved in toluene 50 ml, and PTS 0.5 g was added, and the mixture was refluxed with heating for 3 hours while removing water formed with Dien-Stark. The reactant was washed with a saturated sodium bicarbonate aqueous solution, and then with saturated sodium chloride aqueous solution, and dried over anhydrous magnesium sulfate, and the solvent was distilled off. The residue was recrystallized twice from heptane to obtain 5-propyl-2-(4-(3-fluoro-4-trifluoromethoxy phenyl) cyclohexyl-1,3-dioxane 1.22 g (3.12 mmol). The yield was 23.5% from 4-(3-fluoro-4-trifluoromethoxyphenyl) cyclohexanecarboaldehyde.

$^1$H-NMR(CDCl$_3$) δ(ppm): 7.18–6.82 (m,3H), 4.14–3.90(m,3H), 3.23–3.07(m,2H), 2.38(m,1H), 1.92–0.72(m,16H)

C-S×1 point 52.0° C., S×1-S×2 point 83.2° C., S×2-I point 117.5° C.

EXAMPLE 4

Production of the compound (No. 11), 5-propyl-2-(2-(4-trifluoro methylphenyl)ethyl-1,3-dioxane (in formula (1), R=n-propyl group, n1=n2=0, A=(b), Za=Zb =a single bond, $Q_1=Q_2$=a hydrogen atom, Y=a trifluoromethyl group)

1st Step

Dimethoxyethane 700 ml was added to 60% sodium hydride 24.8 g (620 mmol), the mixture was stirred at room temperature while a solution of ethyl diethylphosphonoacetate 139 g (620 mmol) in dimethoxyethane (100 ml) was added dropwise. After the generation of hydrogen gas was stopped, the solution was cooled to 10° C., and a solution of 4-trifluoromethylbenzaldehyde 100 g (574 mmol) in dimethoxyethane (100 ml) was added dropwise keeping the liquid temperature below 25° C. After addition, the mixture was stirred for 30 minutes, the reactant was added to water one liter, and the product was extracted with diethylether. The extract was washed with a sodium chloride aqueous solution, and dried over anhydrous magnesium sulfate, and the solvent was distilled off under reduced pressure. The residue was purified by silica gel column chromatography (eluent: heptane/ethyl acetate=3/1). Such obtained purified material was hydrogenated in the presence of 5% palladium carbon as a catalyst in ethanol 300 ml. The catalyst was filtered off, the solvent was distilled off at reduced pressure to obtain 3-(4-trifluoromethylphenyl)propionic acid ethylester 81.0 g (329 mmol). The yield was 57.3% from 4-trifluoro methylbenzaldehyde.

2nd Step

The above 3-(4-trifluoromethylphenyl)propionic acid ethylester 81.0 g (329 mmol) was stirred in toluene 500 ml while the temperature was cooled to −60° C., and a 1.01 M of toluene solution 329 ml (332 mmol) of DIBAL was added dropwise, and the mixture was stirred at −55° C. for 15 minutes. At the same temperature, a saturated ammonium chloride aqueous solution 200 ml was added dropwise to the reactant, and the mixture was heated to room temperature and stirred for 30 minutes. Ether 100 ml was added to the reactant, and the mixture was stirred at room temperature for one hour, and magnesium sulfate was added, and the suspension was filtered with cerite. The filtrate was washed with water, the organic layer was dried over magnesium sulfate, and the solvent was distilled off under reduced pressure. The residue was purified by silica gel column chromatography (eluent: toluene) to obtain 3-(4-trifluoromethylphenyl)propanal 62.5 g (309 mmol). The yield was 93.9% from 3-(4-trifluorophenyl)propionic acid ethylester.

3rd Step

2-Propyl-1,3-propanediol 17.4 g (147 mol) and the above 3-(4-trifluoromethylphenyl)propanal 20.0 g (98.9 mmol) were dissolved in toluene 200 ml, and PTS 1 g was added, and the mixture was refluxed with heating for 3 hours while removing water formed with Dien-Stark. The reactant was washed with a saturated sodium bicarbonate aqueous solution, and then with saturated sodium chloride aqueous solution, and dried over anhydrous magnesium sulfate, and the solvent was distilled off. The residue was purified by silica gel column chromatography (eluent: toluene), and recrystallized twice from ethanol to obtain 5-propyl-2-(2-(4-trifluoromethylphenyl)ethyl)-1,3-dioxane 10.8 g (35.7 mmol). The yield was 36.1% from 3-(4-trifluoromethylphenyl) propanal.

$^1$H-NMR(CDCl$_3$) δ(ppm): 7.41 (dd,4H), 4.41(t,1H), 4.18–4.00(m,2H), 3.41–3.16(m,2H), 2.88–2.70(m,2H), 2.14–1.80(m,3H), 1.35–0.81(m,7H)

C-I point 72.6° C.

EXAMPLE 5

Production of the compound (No. 261), 5-propyl-4-(2-(4-trifluoro methylphenyl)butyl-1,3-dioxane (in formula (1), R=n-propyl group, n1=n2=0, A=(c), Za=Zb=a single bond, $Q_1=Q_2$=a hydrogen atom, Y=a trifluoromethyl group)

1st Step

Dimethoxyethane 180 ml was added to 60% sodium hydride 6.52 g (163 mmol), the mixture was stirred at room temperature while a solution of ethyl diethylphosphonoacetate 36.5 g (163 mmol) in dimethoxyethane (50 ml) was added dropwise. After the generation of hydrogen gas was stopped, the solution was cooled to 5° C., and a solution of 3-(4-trifluoromethylphenyl)propanal 30.0 g (148 mmol), which was obtained in 3rd step of Example 4, in dimethoxyethane (50 ml) was added dropwise keeping the liquid temperature below 25 ° C. After addition, the mixture was stirred for 30 minutes at room temperature, the reactant was added to water 200 ml, and the product was extracted with diethylether. The extract was washed with a sodium chloride aqueous solution, and dried over anhydrous magnesium sulfate, and the solvent was distilled off under reduced pressure. The residue was purified by silica gel column chromatography (eluent: heptane/ethyl acetate=3/1). Such obtained purified material was hydrogenated in the presence of 5% palladium carbon as a catalyst in ethanol 300 ml. After hydrogenation, the catalyst was :filtered off, the solvent was distilled off at reduced pressure to obtain 5-(4-trifluoro methylphenyl)pentanoic acid ethylester 13.3 g (48.5 mmol). The yield was 32.8% from 3-(4-trifluoromethylphenyl) propanal.

2nd Step

The above 5-(4-trifluoromethylphenyl)pentanoic acid ethylester 12.2 g (44.5 mmol) was stirred in toluene 70 ml while the temperature was cooled to −60° C., and a 1.01 M of toluene solution 46.0 ml (46.5 mmol) of DIBAL was added dropwise, and the mixture was stirred at −60° C. for 15 minutes. At the same temperature, a saturated ammonium chloride aqueous solution 40 ml was added dropwise to the reactant, and the mixture was heated to room temperature and stirred for 30 minutes. Diethyl ether 100 ml was added to the reactant, and the mixture was stirred at room temperature for one hour, and magnesium sulfate was added, and the suspension was filtered with cerite. The filtrate was washed with water, the organic layer was dried over magnesium sulfate, and the solvent was distilled off under reduced pressure. The residue was purified by silica gel column chromatography (eluent: toluene) to obtain 5-(4-trifluoromethylphenyl)pentanal 7.50 g (32.6 mmol). The yield was 73.3% from 5-(4-trifluorophenyl)pentanoic add ethylester.

3rd Step

2-Propyl-1,3-propanediol 5.90 g (49.9 mmol) and the above 5-(4-trifluoromethylphenyl)pentanal 7.50 g (32.6 mmol) were dissolved in toluene 70 ml, and PTS 1 g was added, and the mixture was refluxed with heating for 3 hours while removing water formed with Dien-Stark. The reactant was washed with a saturated sodium bicarbonate aqueous solution, and then with saturated sodium chloride aqueous solution, and dried over anhydrous magnesium sulfate, and the solvent was distilled off. The residue was purified by silica gel column chromatography (eluent: toluene), and recrystallized twice from ethanol to obtain 5-propyl-2-(4-(4-trifluoromethylphenyl)butyl)-1,3-dioxane 5.55 g (16.7 mmol). The yield was 51.2% from 5-(4-trifluoromethylphenyl) pentanal.

$^1$H-NMR(CDCl$_3$) δ(ppm): 7.40 (dd,4H), 4.42(t,1H), 4.16–3.98(m,2H;), 3.41–3.16(m,2M), 2.76–2.59(m, 2H), 2.10–0.81(m,14H)

C-I point 50.9° C.

EXAMPLE 6

Production of the compound (No. 175), 5-propyl-2-(4-(4-(3-fluoro-4-chlorophenyl)-3,5-difluorophenyl)cyclohexyl)-1,3-dioxane (in formula (1), R=n-propyl group, n1=0, n2=1, A=(a), ring A1=3,5-difluoro-1,4-phenylene, Za=Zb=a single bond, Q$_1$=a fluorine atom, Q$_2$=a hydrogen atom, Y=a chlorine atom)

1st Step

To Grignard reagent prepared from 3,5-difluorobromobenzene 100 g (518 mmol) and magnesium in dried THF 300 ml at room temperature, a THF (300 ml) solution of cyclohexanedione monoethyleneketal 74.6 g (517 mmol) was added dropwise at room temperature, and the mixture was stirred for 3 hours at room temperature. The reactant was added to one liter of 2N-hydrochloric acid, and the product was extracted with diethylether. The extract was washed with water, a saturated sodium bicarbonate aqueous solution, and then water, and dried over anhydrous magnesium sulfate, and the solvent was distilled off under reduced pressure. To the residue, para-toluene sulfonic acid 5 g and toluene 800 ml were added. The mixture was refluxed with heating while removing water formed with Dien-Stark. The reactant was washed with water, a saturated sodium bicarbonate aqueous solution, and then water, and dried over anhydrous magnesium sulfate, and the solvent was distilled off under reduced pressure. The residue was purified by silica gel column chromatography (eluent: heptane/ethyl acetate=3/1). Such obtained purified material was hydrogenated in the presence of 5% palladium carbon 5 g as a catalyst in ethanol 500 ml. The catalyst was filtered off, the solvent was distilled off under reduced pressure, formic acid 40 g and toluene 300 ml were added to the residue, and the mixture was refluxed for 3 hours. After cooling, water 500 ml was added to the reactant, and the organic layer was fractionated, washed with water, a saturated sodium bicarbonate aqueous solution, and then water, and dried over anhydrous magnesium sulfate, and the solvent was distilled off. The residue was purified by silica gel column chromatography (eluent: heptane/ethyl acetate=3/1) to obtain 4-(3,5-difluorophenyl)cyclohexanone 29.4 g (140 mmol). The yield was 27.0% from 3,5-difluorobromobenzene.

2nd Step

To dried MTP 10.0 g (29.2 mmol), THF 100 ml was added, and potassium-t-butoxide 3.30 g (29.4 mmol) was added. The mixture was stirred for about one hour. To the reactant, a THF solution (50 ml) of the above 4-(3,5-difluorophenyl)cyclohexanone 5.0 g (23.8 mmol) was added dropwise, and the mixture was stirred for 2 hours. Water 150 ml was added to the reactant, the product was extracted with diethylether. The extract was washed with a sodium chloride aqueous solution, dried over anhydrous magnesium sulfate, and the solvent was distilled off. The residue was purified by silica gel column chromatography (eluent: toluene). The resulting purified material was stirred in mixture solvent of 3N-hydrochloric add 200 ml and acetone 200 ml for 5 hours at room temperature, and the product was extracted with toluene. The extract was washed with a saturated sodium bicarbonate aqueous solution and then with water, and dried over anhydrous magnesium sulfate. Toluene was distilled off to obtain 4-(3,5-difluorophenyl)cyclohexanecarboaldehyde 5.0 g (22.3 mmol). The yield was 93.7% from 4-(3,5-difluorophenyl) cyclohexanone.

3rd Step

2-Propyl-1,3-propanediol 3.5 g (29.6 mol) and 4-(3,5-difluorophenyl) cyclohexanecarboaldehyde 5.0 g (22.3 mmol) were dissolved in toluene 50 ml, and PTS 0.5 g was added, and the mixture was refluxed with heating for 3 hours while removing water formed with Dien-Stark. The reactant was washed with a saturated sodium bicarbonate aqueous solution, and then with saturated sodium chloride aqueous solution, and dried over anhydrous magnesium sulfate, and the solvent was distilled off. The residue was recrystallized twice from heptane to obtain 5-propyl-2-(4-(3,5-difluorophenyl)cyclohexyl-1,3-dioxane 2.3 g (7.1 mmol). The yield was 24.0% from 4-(3,5-difluorophenyl) cyclohexanecarbo aldehyde.

4th Step

The above 5-propyl-2-(4-(3,5-difluorophenyl) cyclohexyl-1,3-dioxane 1.3 g (4.0 mmol) was dissolved in THF 10 ml, and cooled to −65° C. under a nitrogen atmosphere. To this solution, 1.68 M hexane solution 3.0 ml (5.0 mmol) of n-butyllithium was added dropwise keeping the liquid temperature below −55° C., and the mixture was stirred for one hour at the same temperature. Then, to the reactant, 0.5 M THF solution 10 ml (5.0 mmol) of zinc chloride was added dropwise keeping the liquid temperature below −50° C., and the mixture was heated to room temperature and stirred for 30 minutes. Tetrakistriphenylphosphin paradium 0.5 g and 3-fluoro-4-chlorobromobenzene 1.1 g (5.3 mmol) were added to the solution, and the mixture was refluxed with heating for 3 hours. Water 30 ml was added to the resulting reactant, and the product was extracted with toluene. The extract was washed with 3N-hydrochloric acid, a saturated bicarbonate aqueous solution and then a saturated sodium chloride aqueous solution, and dried over magnesium sulfate, and the solvent was distilled off. The residue was purified by silica gel column chromatography (eluent: toluene), and recrystallized twice from a mixed solvent of heptane/ethyl acetate=1/1 to obtain 5-propyl-2-(4-(4-(3-fluoro-4-chlorophenyl)-3,5-difluorophenyl) cyclohexyl)-1,3-dioxane 1.7 g (3.8 mmol). The yield was 95.0% from 5-propyl-2-(4-(3,5-difluorophenyl)ethyl)-1,3-dioxane.

$^1$H-NMR(CDCl$_3$) δ(ppm): 7.54–7.14 (m,3H), 6.95–6.72(m,2H), 4.25–4.01(m,3H), 3,43–3.18(m,2H), 2.63–2.37(m, 1H), 2.04–0.82(m, 17H)

C-N point 110.1° C., N-I point 227.9° C.

EXAMPLE 7

Production of the compound (No. 362), 4-(5-pentyl-1,3-dioxane-2-yl) cyclohexanecarboxylic acid 3,4,5-trifluorophenylester (in formula (1), R=n-pentyl group, n1=n2=0, A=(a), Za=a single bond, Zb=—COO—, $Q_1=Q_2$=a fluorine atom, Y=a fluorine atom)

1st Step

To dried MTP 50.0 g (146 mmol), THF 500 ml was added, and potassium-t-butoxide 18.0 g (160 mmol) was added. The mixture was stirred for about one hour. To the reactant, a THF solution (100 ml) of 4-oxocyclohexane carboxylic acid methylester 21.9 g (140 mmol) was added dropwise, and the mixture was stirred for 2 hours. Water 500 ml was added to the reactant, the product was extracted with diethylether. The extract was washed with a sodium chloride aqueous solution, dried over anhydrous magnesium sulfate, and the solvent was distilled off. The residue was purified by silica gel column chromatography (eluent: toluene). Such resulting purified material was stirred in mixed solvent of 2N-hydrochloric acid 500 ml and acetone 500 ml for 5 hours at room temperature, and the product was extracted with toluene. The extract was washed with a saturated sodium bicarbonate aqueous solution and then with water, and dried over anhydrous magnesium sulfate. Toluene was distilled off to obtain 4-formylcyclohexane carboxylic acid methyl ester 18.8 g (111 mmol). The yield was 79.2% from 4-oxocyclohexane carboxylic acid methylester.

2nd Step

2-Pentyl-1,3-propanediol 17.0 g (116 mol) and 4-formylcyclohexane carboxylic acid methyl ester 18.8 g (111 mmol) were dissolved in toluene 120 ml, and PTS 1.0 g was added, and the mixture was refluxed with heating for 3 hours while removing water formed with Dien-Stark. The reactant was washed with a saturated sodium bicarbonate aqueous solution, and then with saturated sodium chloride aqueous solution, and dried over anhydrous magnesium sulfate, and the solvent was distilled off. The residue was purified by silica gel column chromatography (eluent: toluene/ethyl acetate=4/1) to obtain 4-(5-pentyl-1,3-dioxane-2-yl)cyclohexanecarboxylic acid methylester 28.2 g (94.5 mmol). The yield was 85.1% from 4-formylcyclohexanecarboxylic acid methylester.

3rd Step 4-(5-Pentyl-1,3-dioxane-2-yl)cyclohexanecarboxylic acid methylester 28.2 g (94.5 mmol) was added in ethanol 100 ml, and cooled to 7° C., and 2N-sodium hydroxide 70 ml was added dropwise. The mixture was heated to room temperature, and stirred for one hour, and 2N-sodium hydroxide 70 ml was added dropwise. After st g the mixture father one hour at room temperature, 2N-sodium hydroxide 50 ml was added dropwise, and the mixture was stirred further one hour at room temperature. 6N-Hydrochloric acid 65 ml was added to the reactant, and the product was extracted with diethylether. The extract was washed with water, a saturated sodium bicarbonate aqueous solution and then water, and dried over magnesium sulfate, and the solvent was distilled off. The residue 27.3 g was purified by silica gel column chromatography (eluent: toluene/ethyl acetate=1/1), and recrystallized from a mixed solvent of heptane/ethanol =20/1 to obtain 4-(5-pentyl-1,3-dioxane-2-yl)cyclohexanecarboxylic acid 2.3 g (8.1 mmol). The yield was 8.6% from 4-(5-pentyl-1,3-dioxane-2-yl)cyclohexane carboxylic acid methylester.

4th Step

To 200 ml of three necked flask equipped with a calcium chloride tube, methylene chloride 10 ml, the said $^4$-(5-pentyl-1,3-dioxane-2-yl)cyclohexanecarboxylic acid 1.5 g (5.3 mmol), 3,4,5-trifluorophenol 1.0 g (6.9 mmol) and 4-dimethylaminopyridine 0.2 g (1.6 mmol) were charged, and the mixture was cooled to 0° C. with stirring, and a solution of dicyclohexylcarbodiimide 1.6 g (7.9 mmol) in methylene chloride (8 ml) was added dropwise for two minutes. The mixture was heated to room temperature and stirred at the same temperature for 3 hours. The reactant was filtered, and the filtrate was washed with 5N-hydrochloric acid 20 ml, and again filtered. The filtrate was washed with a saturated sodium bicarbonate aqueous solution and then water, and dried over magnesium sulfate, and the solvent was distilled off under reduced pressure. The residue was purified by silica gel column chromatography (eluent: toluene/ethyl acetate=4/1), and recrystallized from ethanol and then fom a mixed solvent of ethanol/heptane=9/1 to obtain 4-(5-pentyl-(1,3-dioxane)-2-yl)cyclo hexanecarboxylic acid 3,4,5-trifluorophenylester 1.30 g (3.1 mmol). The yield was 58% from 4-(5-pentyl-(1,3-dioxane)-2-yl) cyclohexanecarboxylic acid.

$^1$H-NMR(CDCl$_3$) δ(ppm): 6.89–6.69(m,2H), 4.22–3.99(m,3H), 3.41–3.15(m,2H), 2.61–0.81(m, 22H)

C-N point 62.1° C., N-I point 74.6° C., (N-SA point 49.3° C.)

EXAMPLE 8

Production of the compound (No. 352), 1-(2-(1,3-dioxane-2-yl)ethyl)cyclohexyl-3,4,5-trifluorobenzene (in formula (1), R=a hydrogen atom, n1=0, n2=1, A=(b), ring A1=1,4-cyclohexylene, Za=Zb=a single bond, $Q_1=Q_2$=a fluorine atom, Y=a fluorine atom)

1st Step

To dried 1,3-dioxane-2-ylethyltriphenylphosphoniumbromide 48.0 g (105 mmol), THF 500 ml was added, and potassium-t-butoxide 11.8 g (105 mmol) was added. The mixture was stirred for about one hour. To the reactant, a THF solution (200 ml) of 4-(3,5-difluorophenyl)cyclohexanone 20.0 g (87.6 mmol), which was obtained by the said 1st step of Example 6, was added dropwise at room temperature, and the mixture was stirred for 2.5 hours. Water 500 ml was added to the reactant, the product was extracted with toluene. The extract was washed with a sodium chloride aqueous solution, dried over anhydrous magnesium sulfate, and the solvent was distilled off. The residue was purified by silica gel column chromatography (eluent: toluene). Such obtained purified material was hydrogenated in the presence of 5% palladium carbon as a catalyst in ethanol 100 ml. The catalyst was filtered off, the filtrate was concentrated, the resulting residue was purified by silica gel column chromatography (eluent: toluene) and recrystallized from ethanol to obtain 1-(2-(1, 3-dioxane-2-yl)ethyl)cyclohexyl-3,4,5-trifluorobenzene 15.2 g (46.3 mmol). The yield was 52.9% from 4-(3,5-difluorophenyl)cyclohexanone.

C-I point 69.8° C.

EXAMPLE 9

Production of the compound (No. 33), 1-(2-(5-propyl-1, 3-dioxane-2-yl)ethyl)cyclohexyl-3,4,5-trifluorobenzene (in formula (1), R=n-propyl group, n1=0, n2=1, A=(b), ring A1=1,4-cyclohexylene, Za=Zb=a single bond, $Q_1=Q_2$=a fluorine atom, Y=a fluorine atom)

1st Step 1-(2-(1,3-Dioxane-2-yl)ethyl)cyclohexyl-3,4,5-trifluorobenzene 3.7 g (11 mmol) obtained in Example 8 and formic acid 25.0 g (540 mmol) were added to toluene 20 ml, and the mixture was refluxed with heating for 3 hours. The reactant was cooled to room temperature, water 100 ml was added, and the product was extracted with toluene. The extract was washed with water, a saturated sodium bicarbonate aqueous solution, and water, and dried over anhydrous magnesium sulfate, and the solvent was distilled off to obtain crude 3-(4-(3,4,5-trifluorophenyl)cyclohexyl) propanal 3.5 g. The product and 2-propyl-1,3-propanediol 2.3 g (20 mmol) were dissolved in toluene 20 ml, PTS 0.5 g was added. The mixture was refluxed with heating for 3 hours while removing water formed with Dien-Stark. The reactant was washed with a saturated sodium bicarbonate aqueous solution, and then with saturated sodium chloride aqueous solution, and dried over anhydrous magnesium sulfate, and the solvent was distilled off. The residue was purified by silica gel column chromatography (eluent: toluene) and recrystallized twice from ethanol to obtain 1-(2-(5-propyl-1,3-dioxane-2-yl)ethyl)cyclohexyl-3,4,5-trifluorobenzene 1.4 g (3.8 mmol). The yield was 34.5% from 1-(2-(1,3-dioxane-2-yl)ethyl)cyclohexyl-3,4,5-trifluorobenzene.

$^1$H-NMR(CDCl$_3$) δ(ppm): 6.87–6.70(m,2H), 4.42(t, 1H), 4.17–3.99(m,2H), 3.43–3.18(m,2H), 2.54–2.25 (m,1H), 1.93–0.81(m,21H)

C-I point 88.6° C.

Based on the description of Examples 1–9 and the column of the detailed description of the present specification, we can produce the following compounds of Nos. 1–370. In addition, the compounds of Examples 1–9 are added again in the list.

No. 1

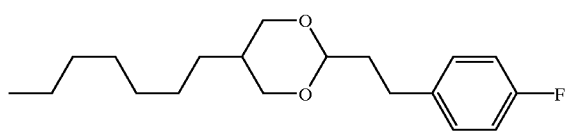

No. 2

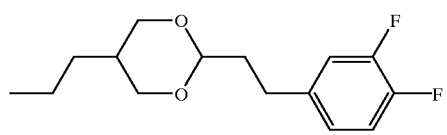

No. 3

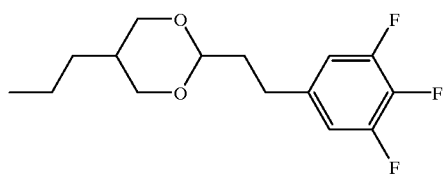

No. 4

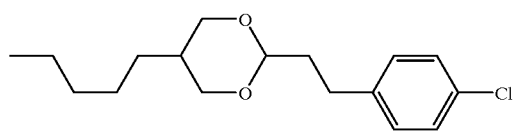

-continued
No. 5
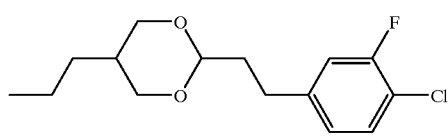
No. 6
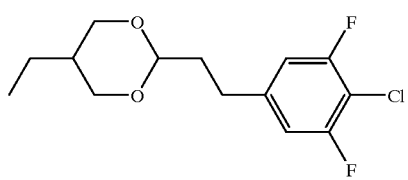
No. 7
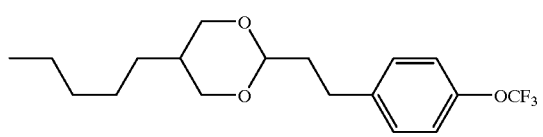
No. 8
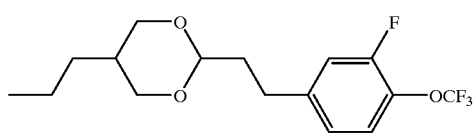
No. 9
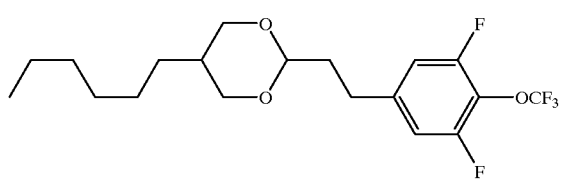
No. 10
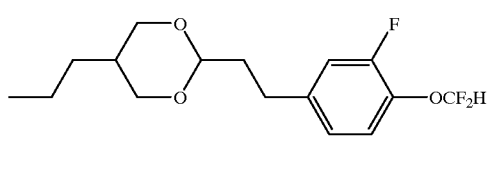
No. 11
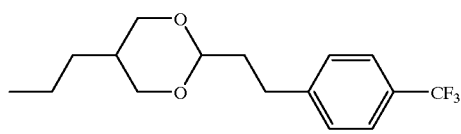
No. 12
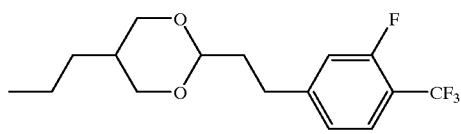
No. 13
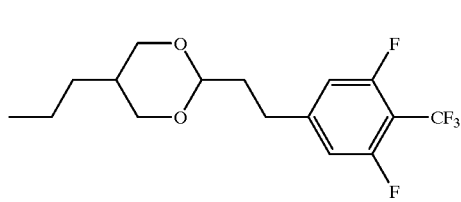
No. 14
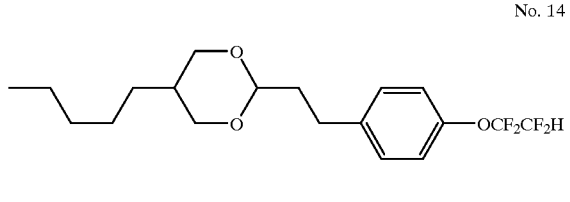
No. 15
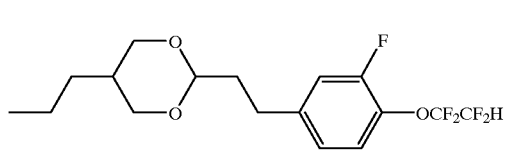
No. 16
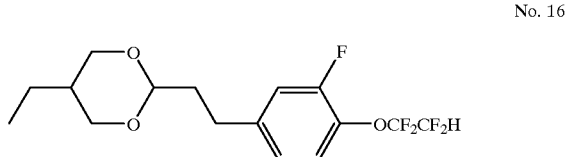
No. 17
No. 18
No. 19
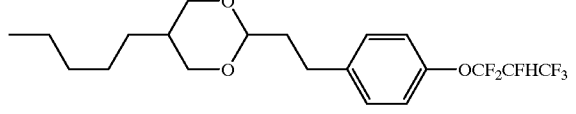
No. 20
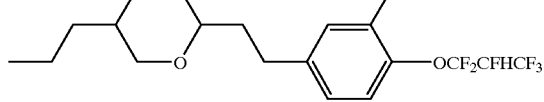
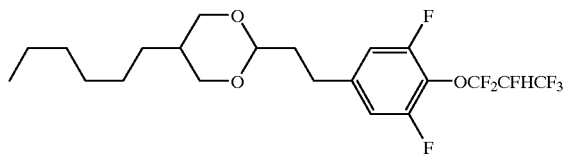
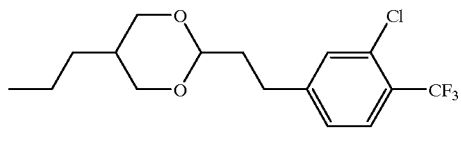

-continued
No. 21
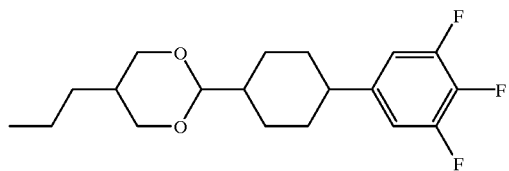
No. 22
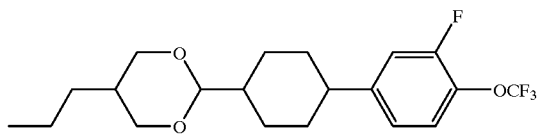
No. 23
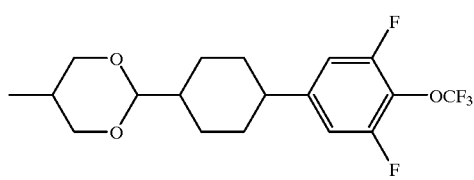
No. 24
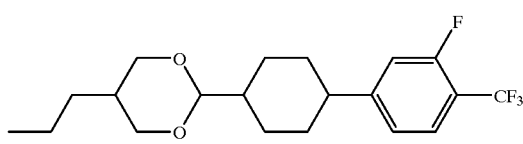
No. 25
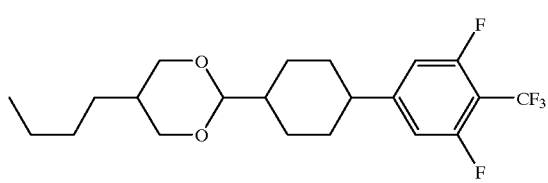
No. 26
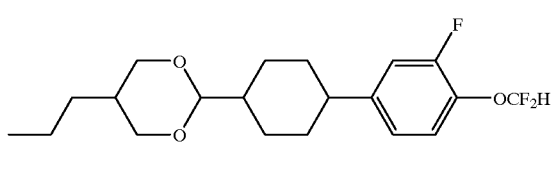
No. 27
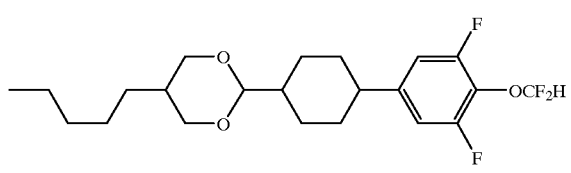
No. 28
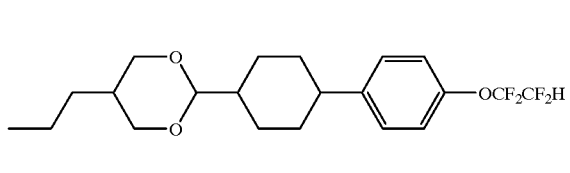
No. 29
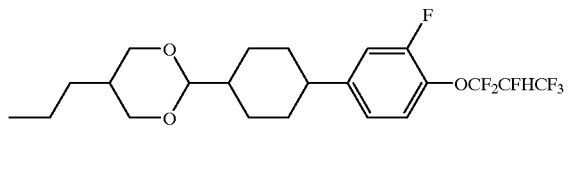
No. 30
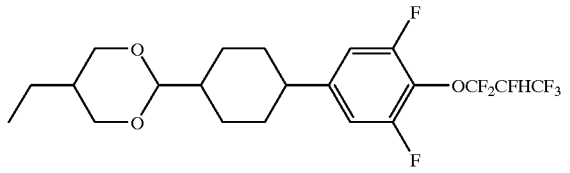
No. 31
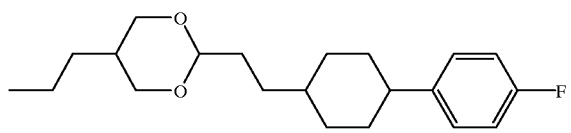
No. 32
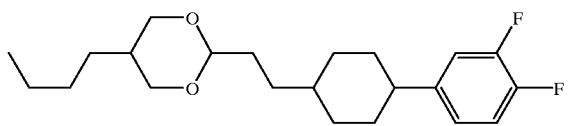
No. 33
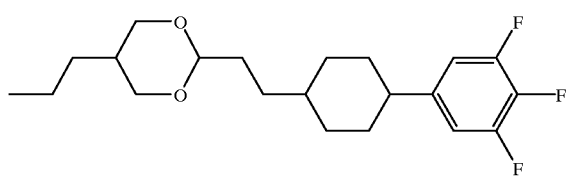
No. 34
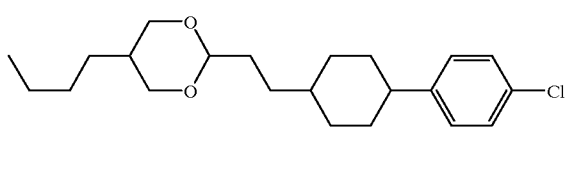
No. 35
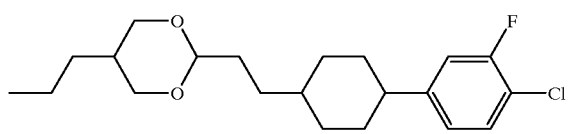
No. 36
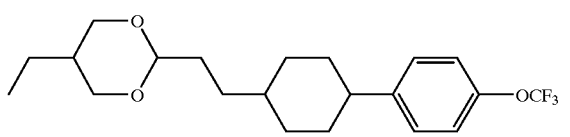

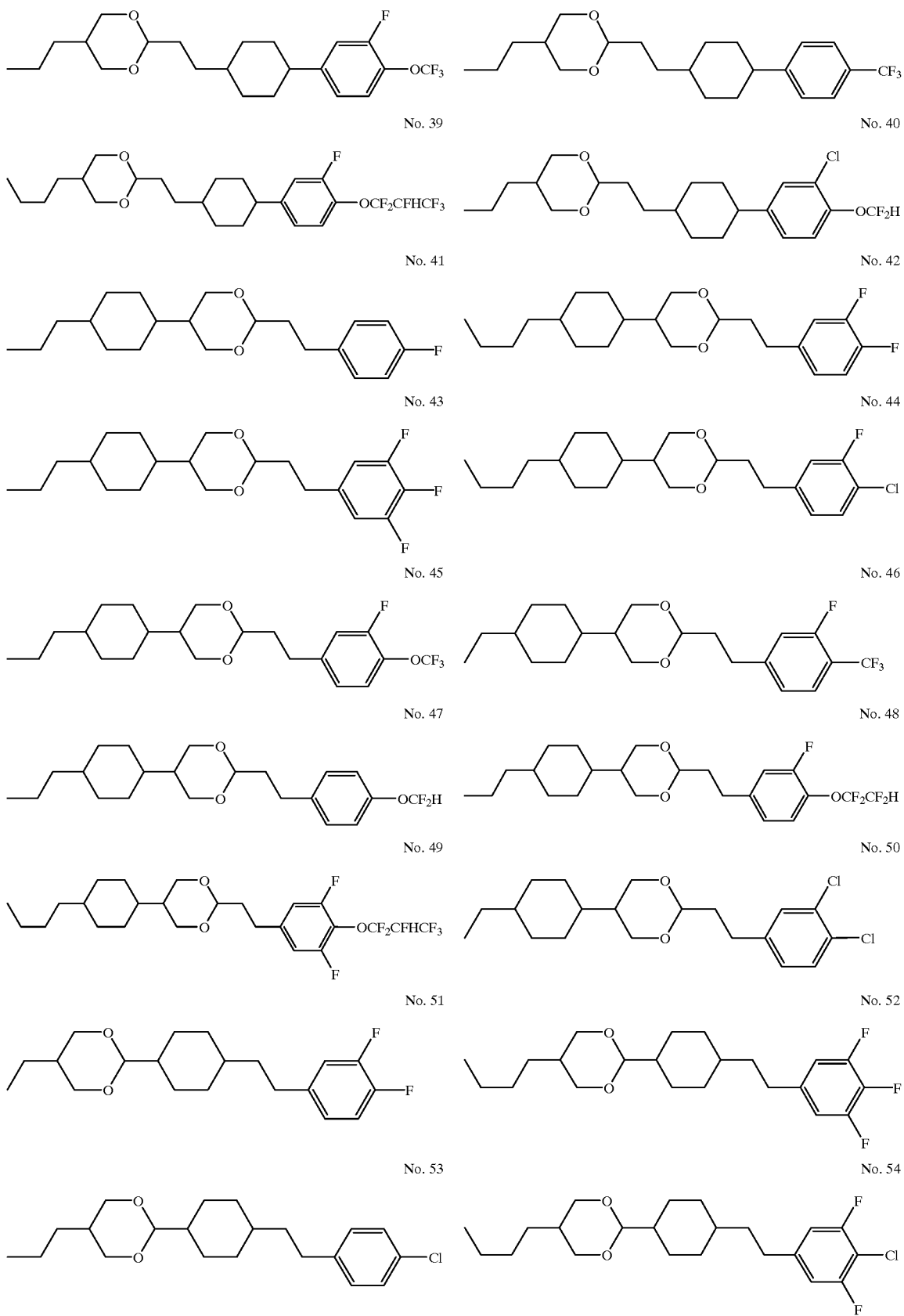

-continued
No. 55
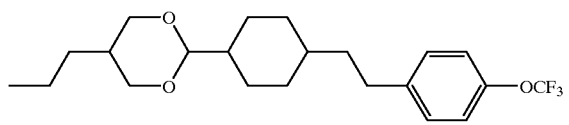
No. 56
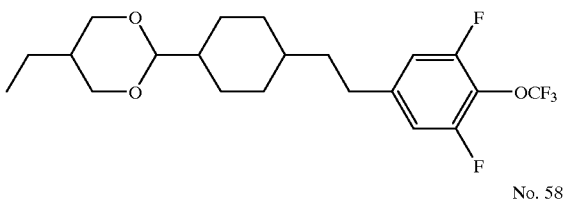
No. 57
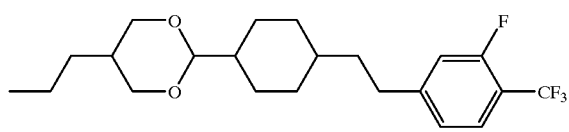
No. 58
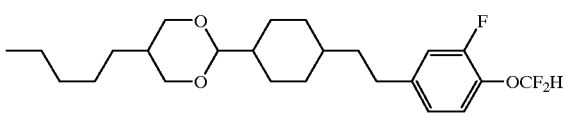
No. 59
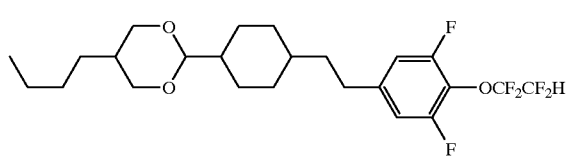
No. 60
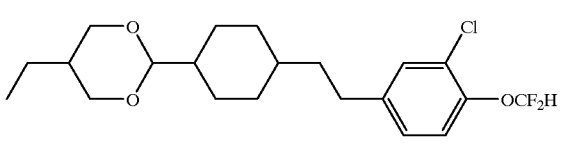
No. 61
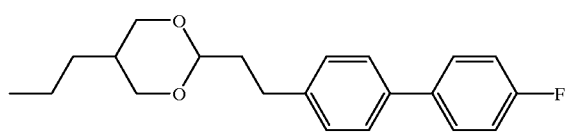
No. 62
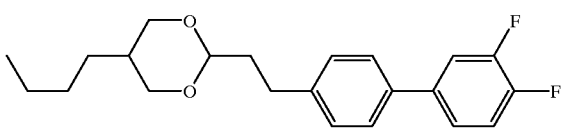
No. 63
No. 64
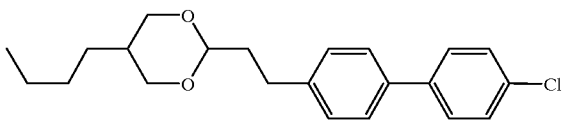
No. 65
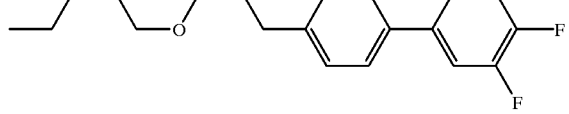
No. 66
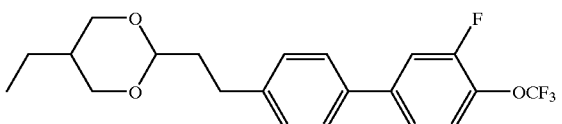
No. 67
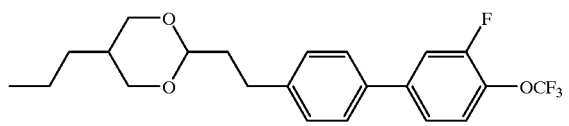
No. 68
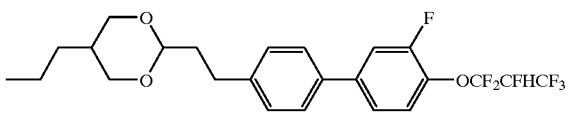
No. 69
No. 70
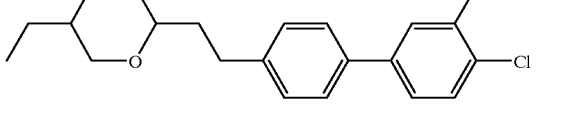
No. 71
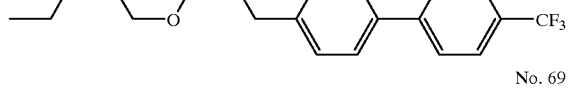
No. 72
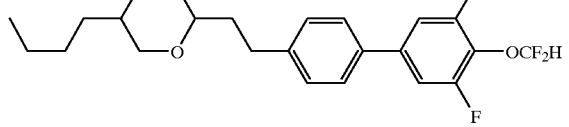
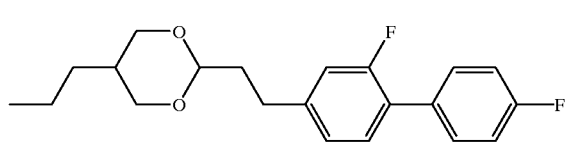

-continued
No. 73
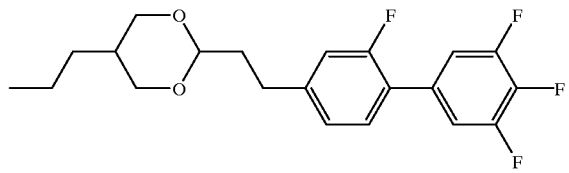
No. 74
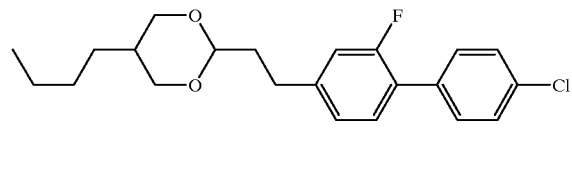
No. 75 No. 76
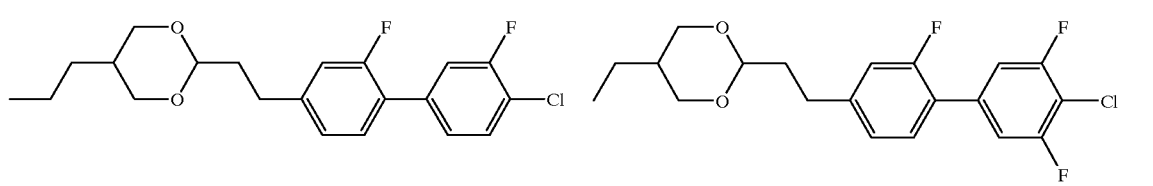
No. 77 No. 78
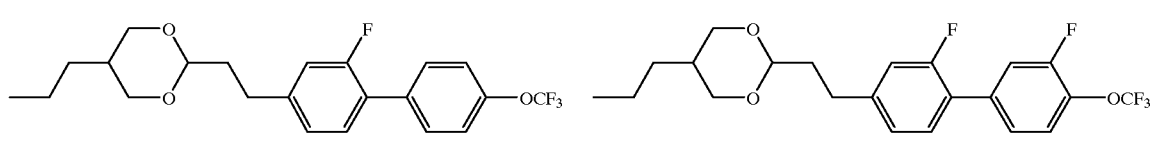
No. 79 No. 80
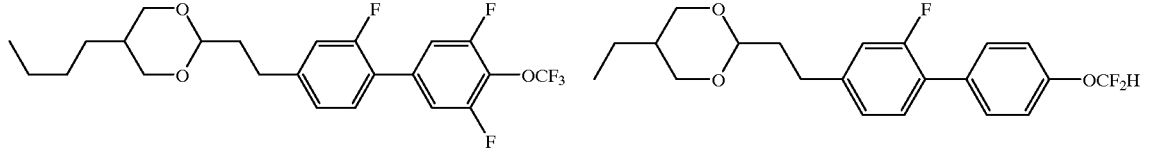
No. 81 No. 82
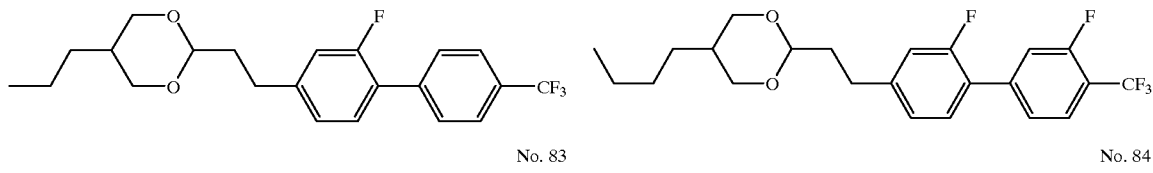
No. 83 No. 84
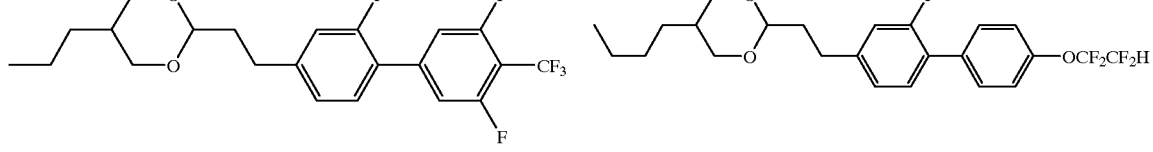
No. 85 No. 86
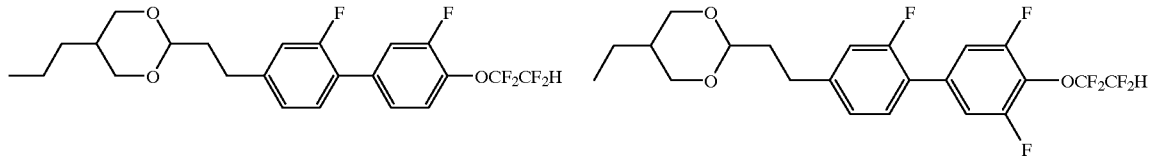
No. 87 No. 88
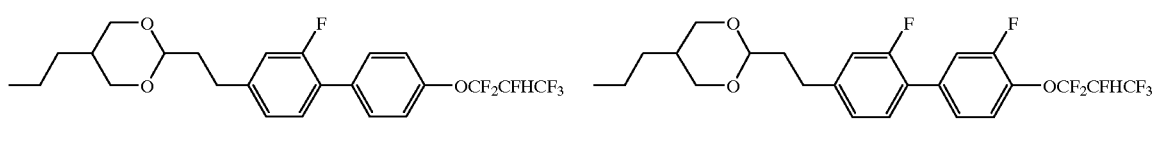

-continued

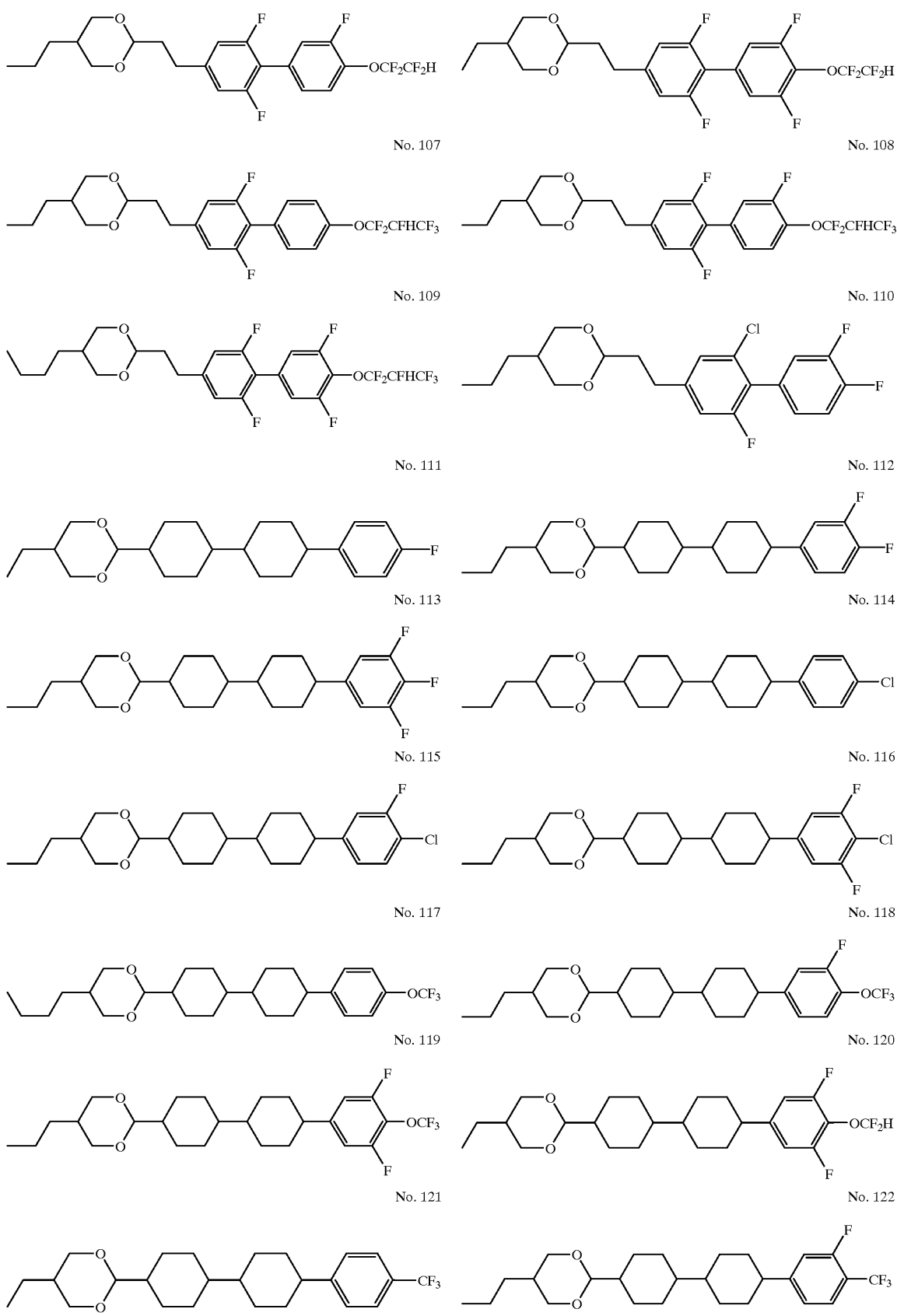

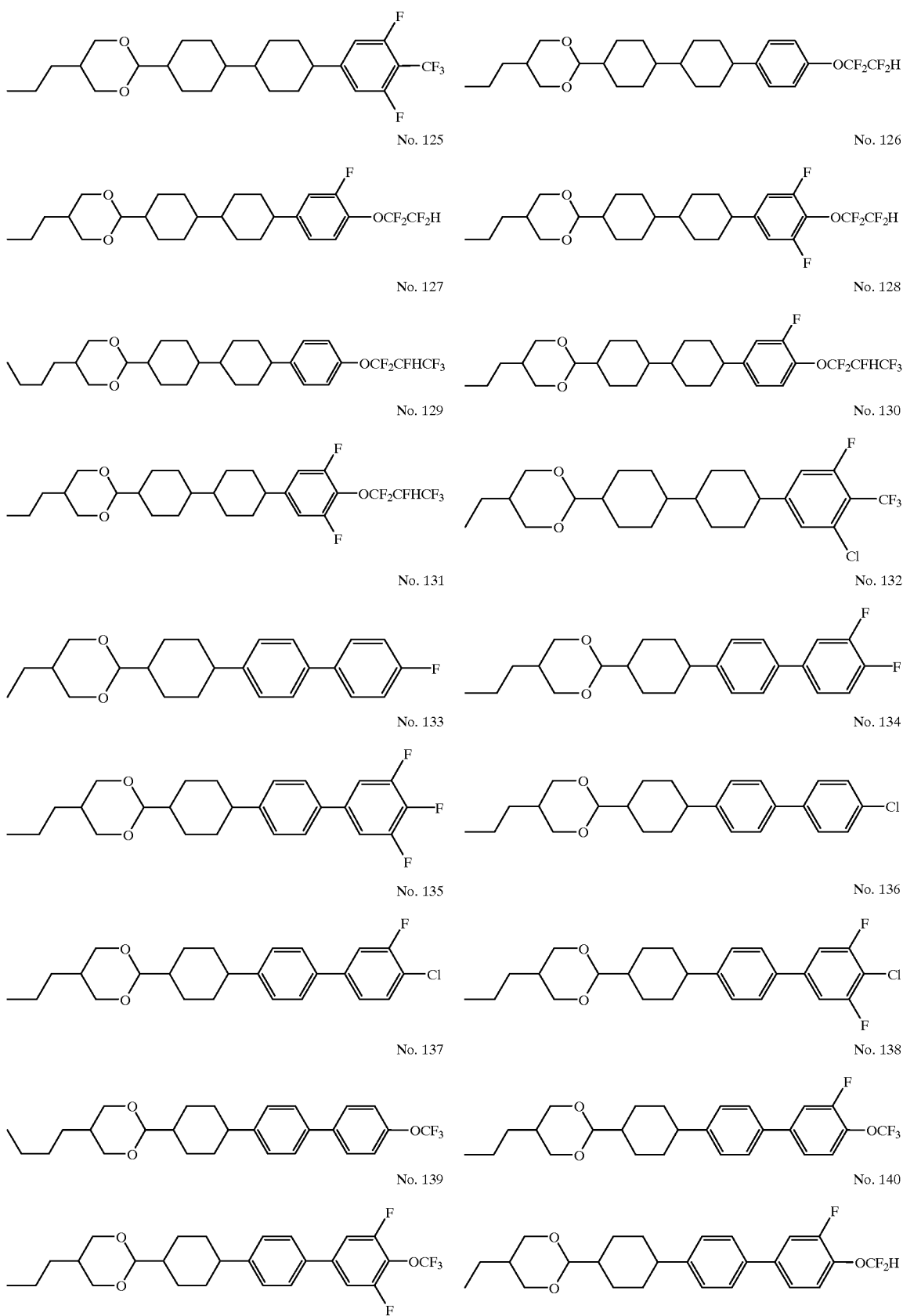

-continued

No. 141

No. 142

No. 143

No. 144

No. 145

No. 146

No. 147

No. 148

No. 149

No. 150

No. 151

No. 152

No. 153

No. 154

No. 155

No. 156

No. 157

No. 158

-continued

No. 159
No. 160
No. 161
No. 162
No. 163
No. 164
No. 165
No. 166
No. 167
No. 168
No. 169
No. 170
No. 171
No. 172
No. 173
No. 174
No. 175
No. 176

-continued
No. 177
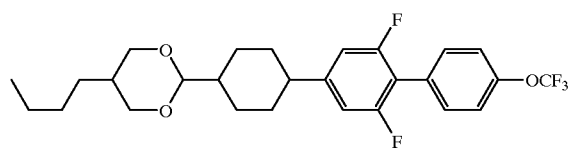
No. 178
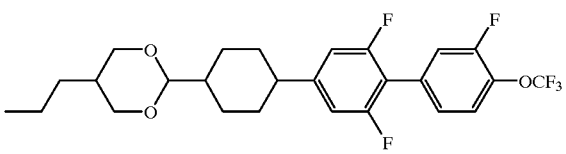
No. 179
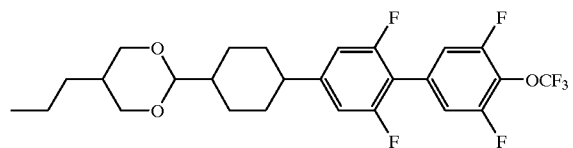
No. 180
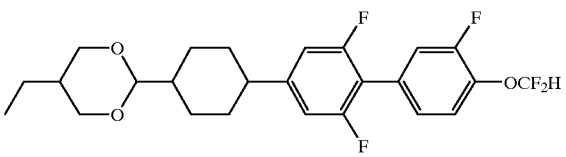
No. 181
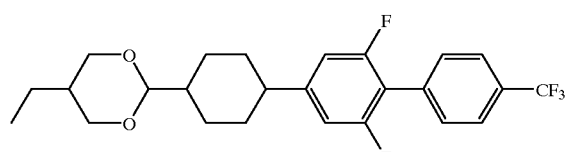
No. 182
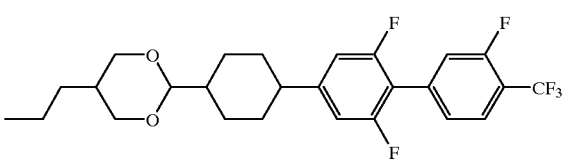
No. 183
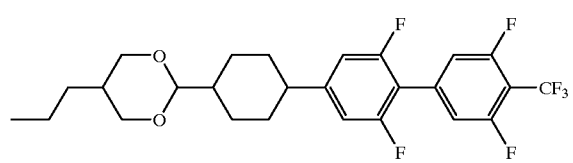
No. 184
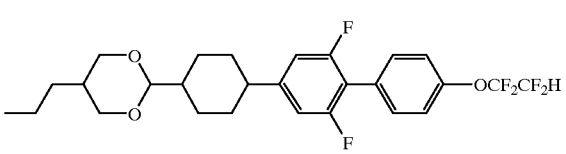
No. 185
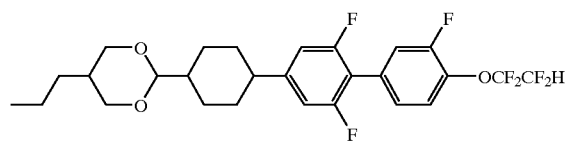
No. 186
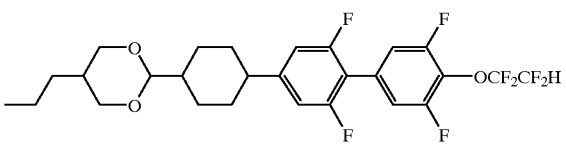
No. 187
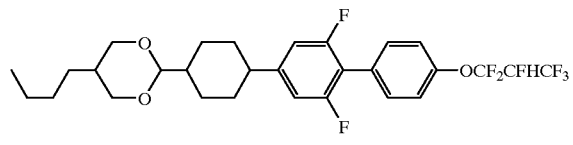
No. 188
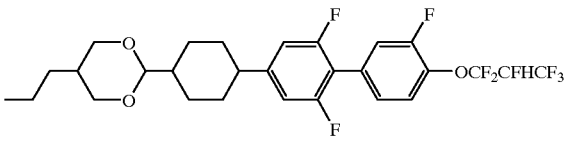
No. 189
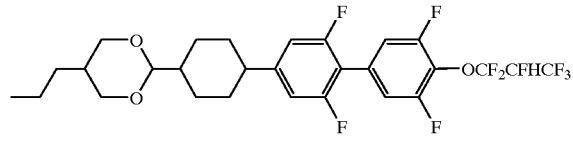
No. 190
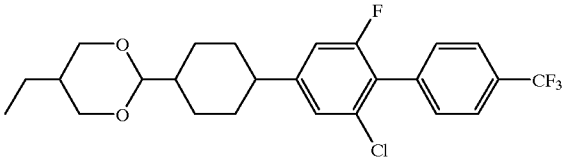
No. 191
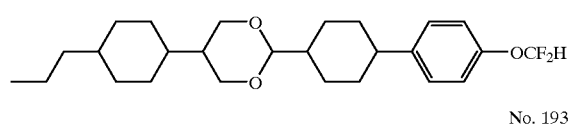
No. 192
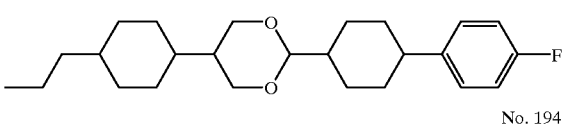
No. 193
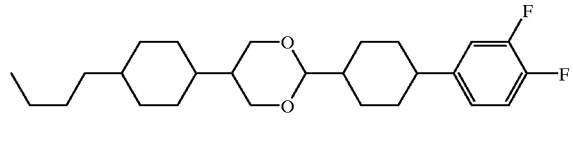
No. 194
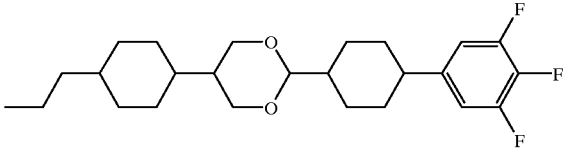

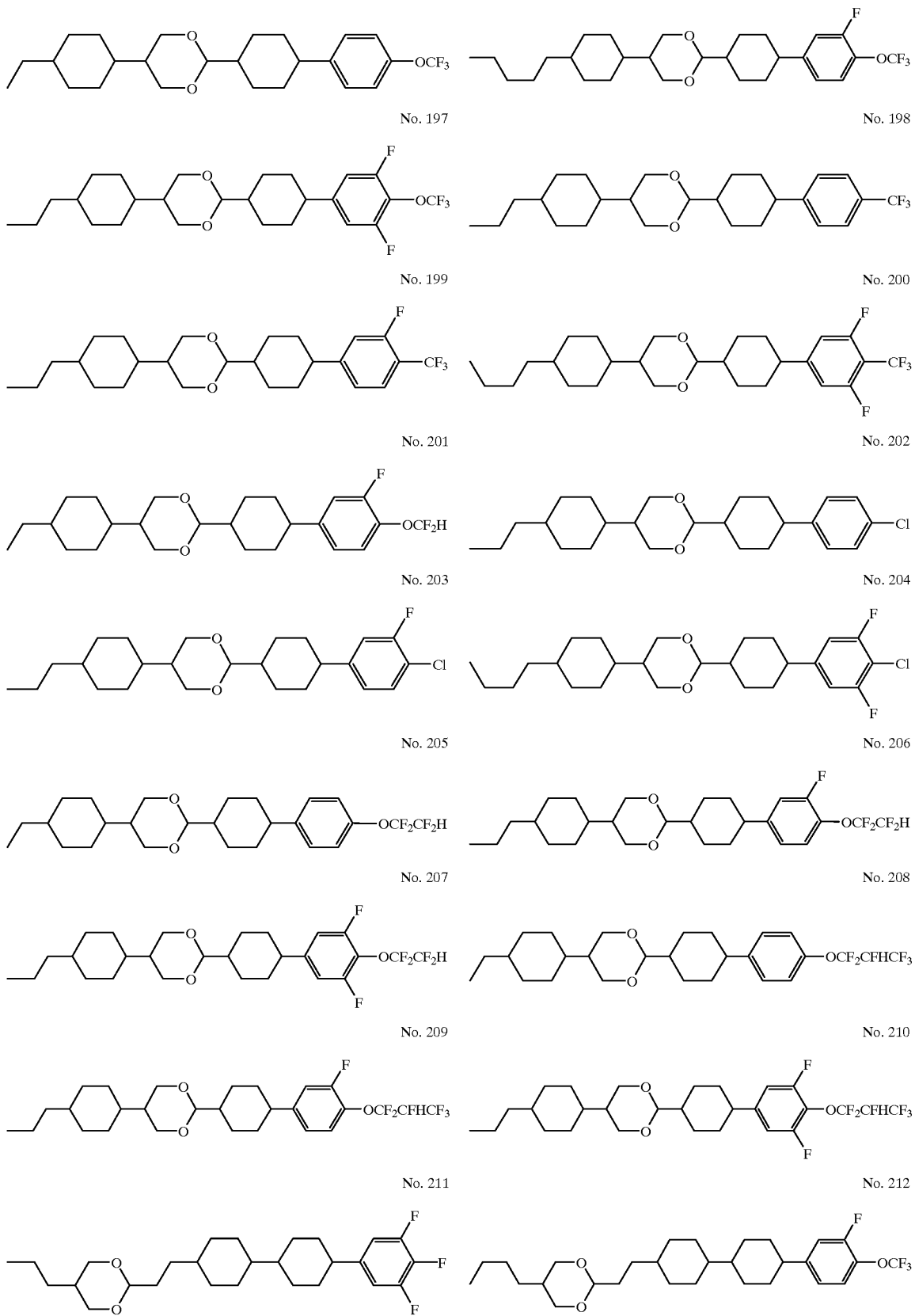

-continued
No. 213
No. 214
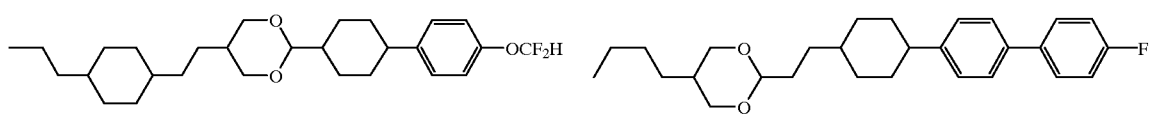
No. 215
No. 216
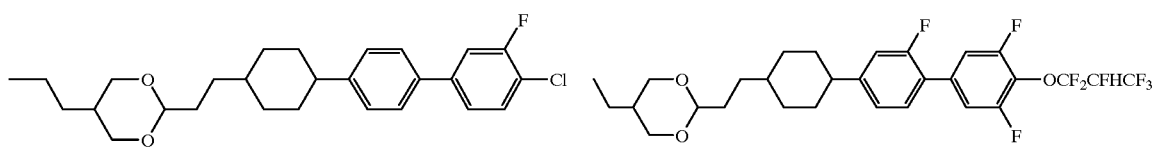
No. 217
No. 218
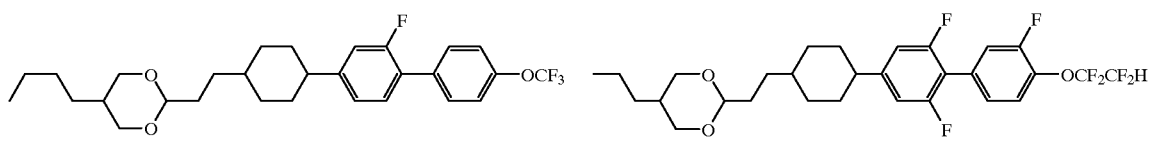
No. 219
No. 220
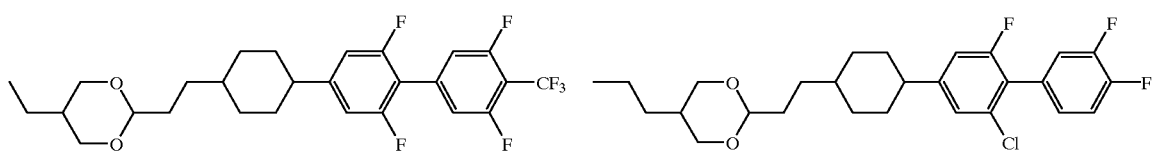
No. 221
No. 222
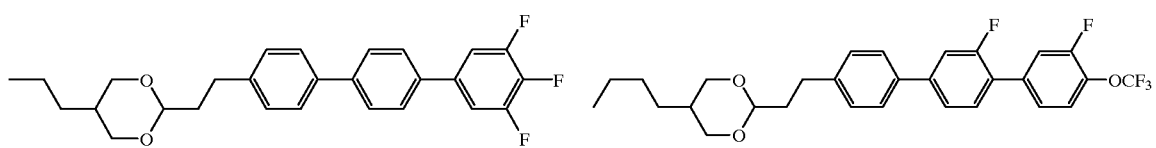
No. 223
No. 224
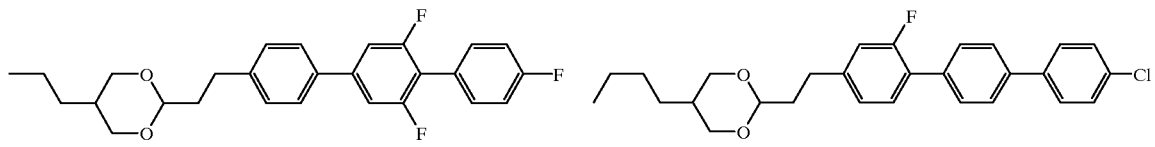
No. 225
No. 226
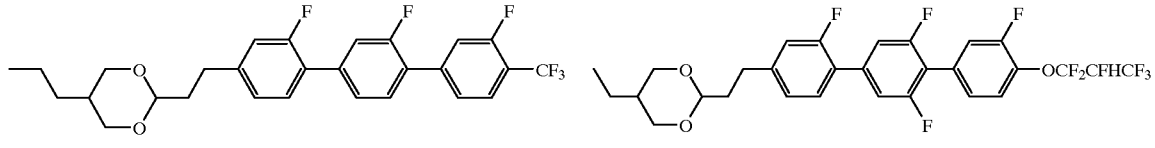
No. 227
No. 228
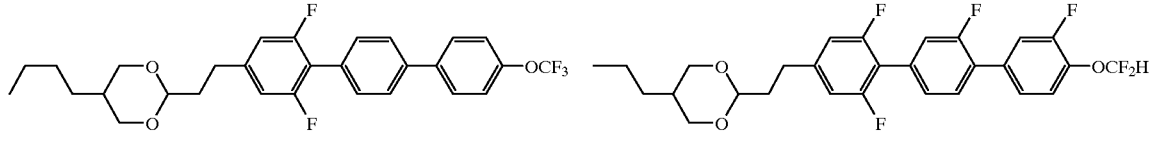
No. 229
No. 230
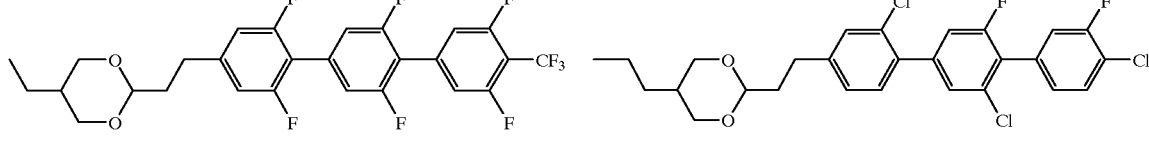

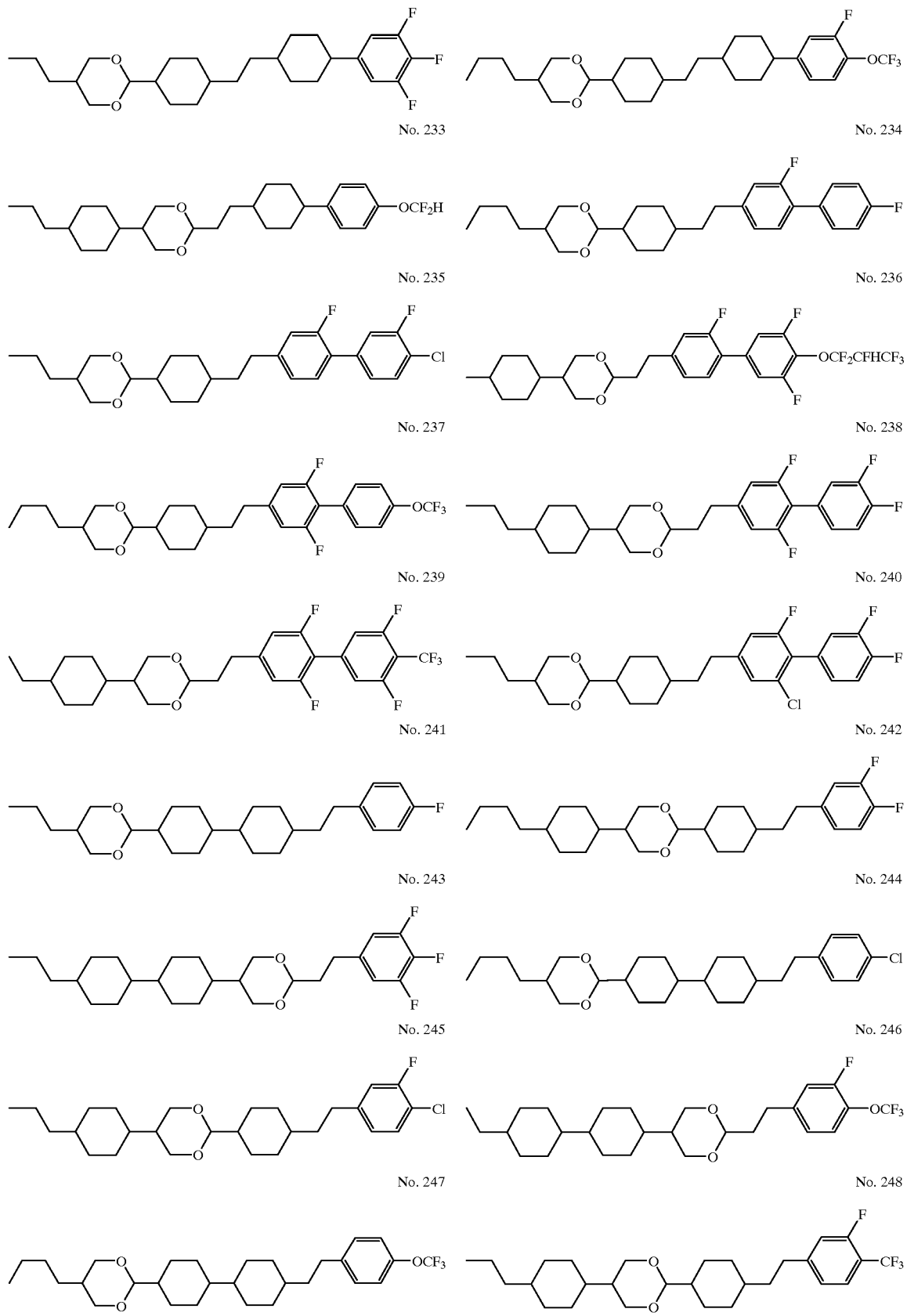

-continued
No. 249
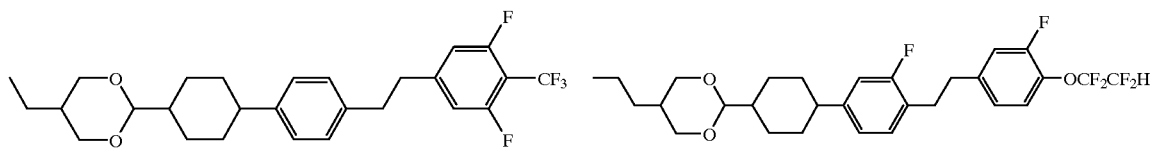
No. 250
No. 251
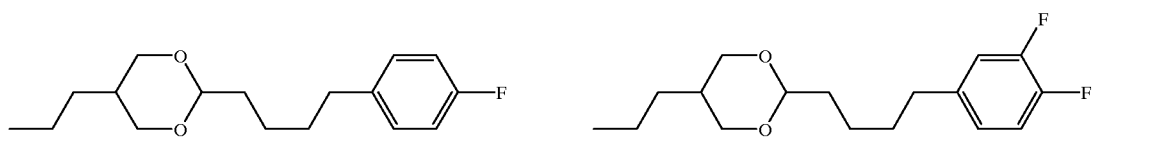
No. 252
No. 253
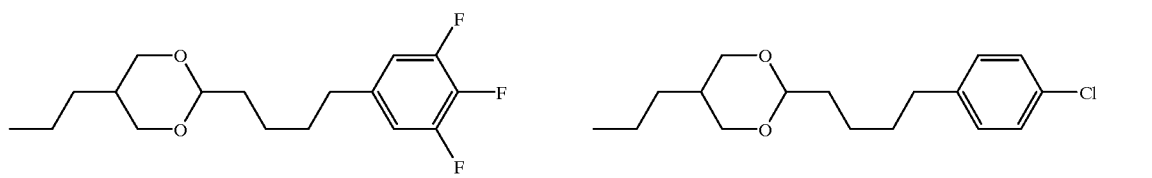
No. 254
No. 255
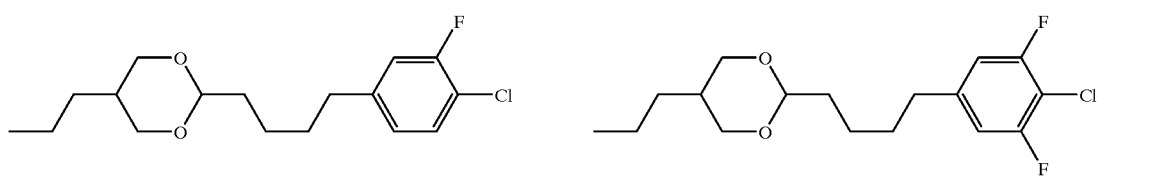
No. 256
No. 257
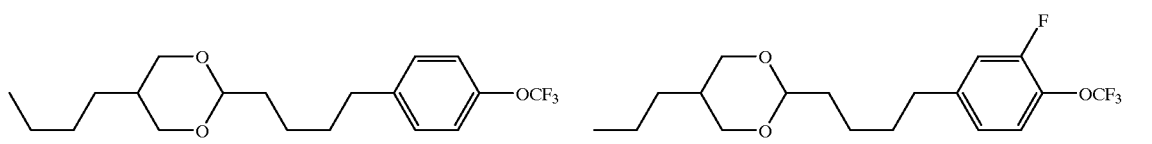
No. 258
No. 259
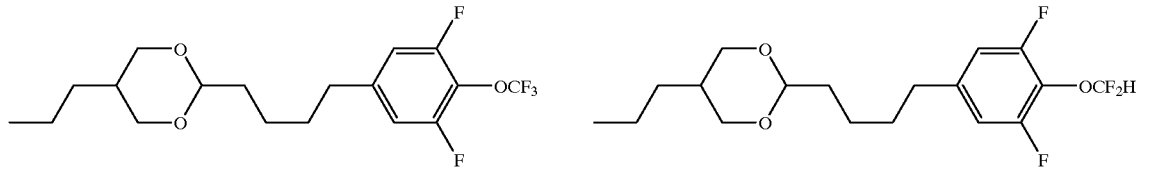
No. 260
No. 261
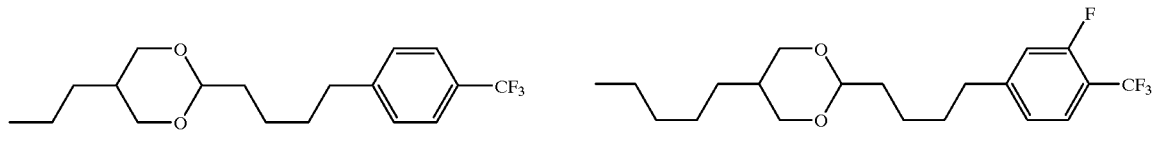
No. 262
No. 263
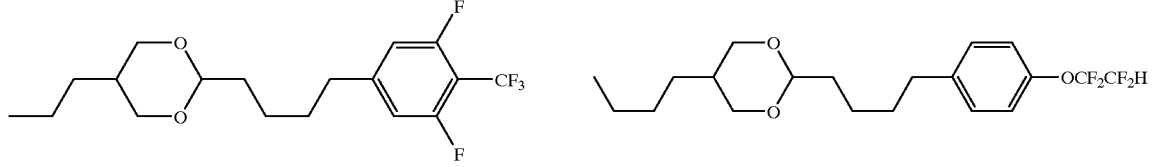
No. 264

-continued
No. 265
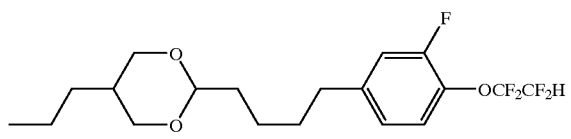
No. 266
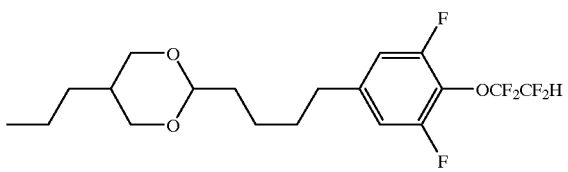
No. 267
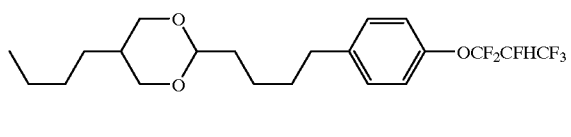
No. 268
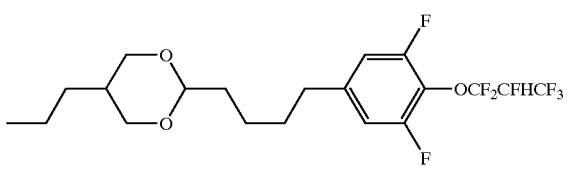
No. 269
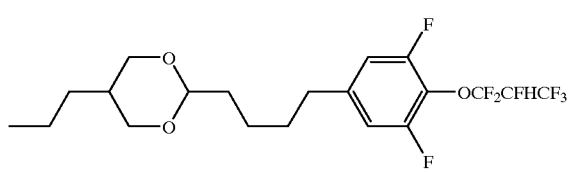
No. 270
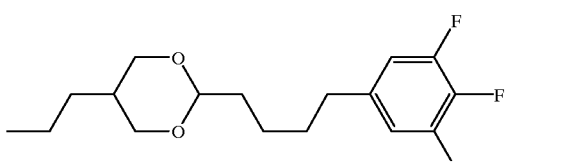
No. 271
No. 272
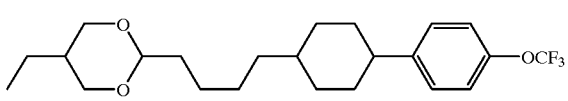
No. 273
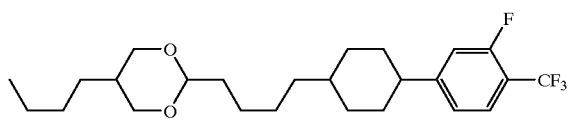
No. 274
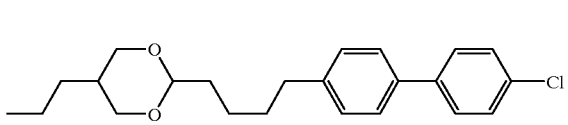
No. 275
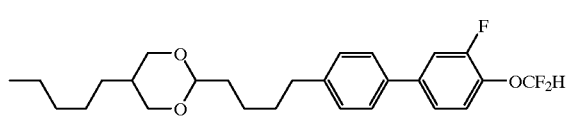
No. 276
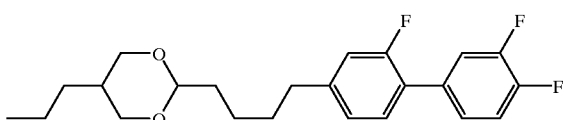
No. 277
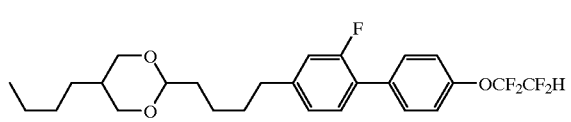
No. 278
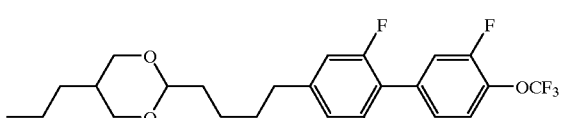
No. 279
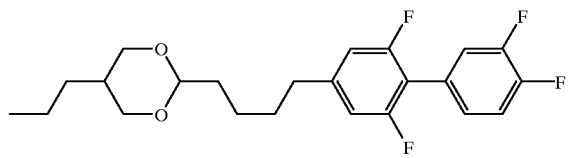
No. 280
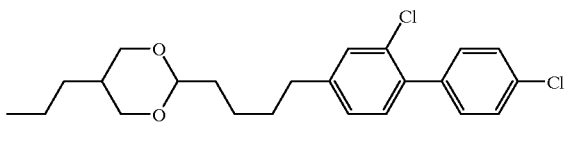
No. 281
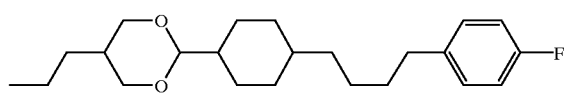
No. 282
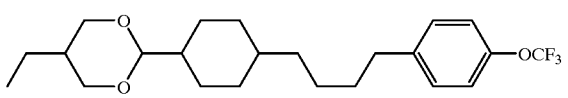

-continued
No. 283
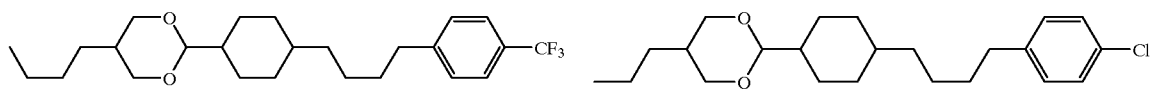
No. 284
No. 285
No. 286
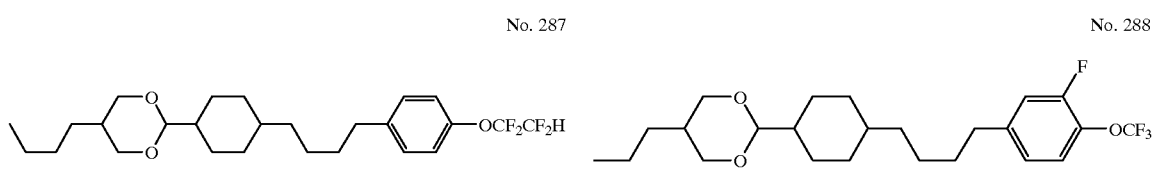
No. 287
No. 288
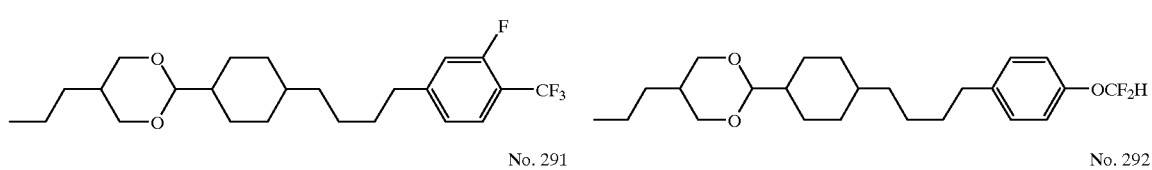
No. 289
No. 290
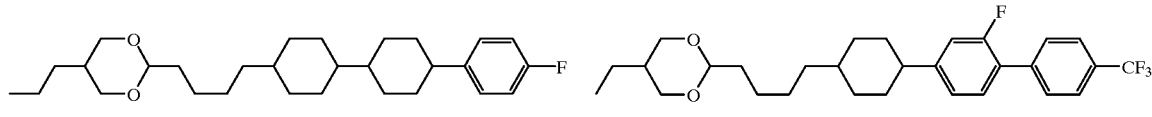
No. 291
No. 292
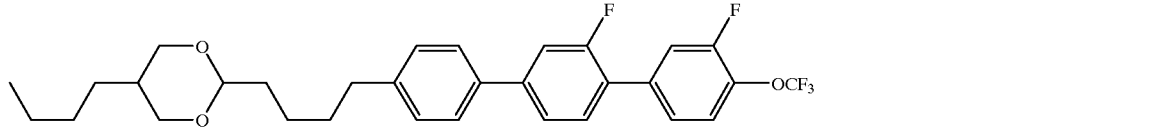
No. 293
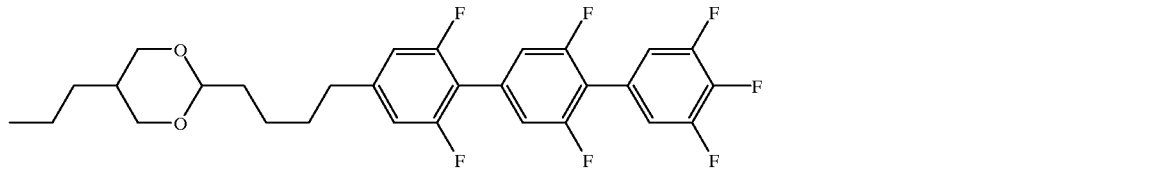
No. 294
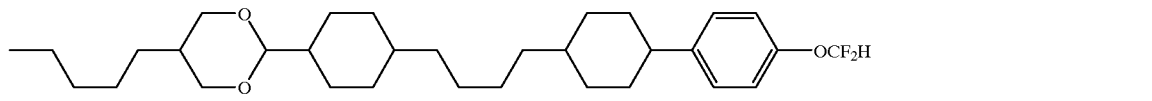
No. 295
No. 296
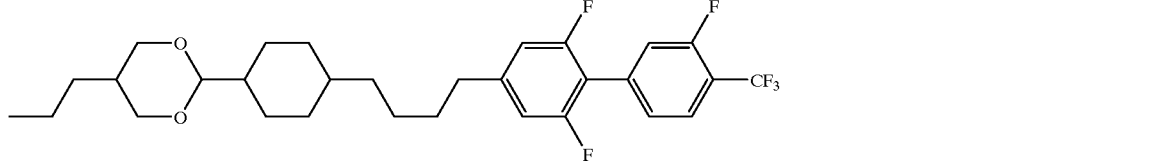
No. 297
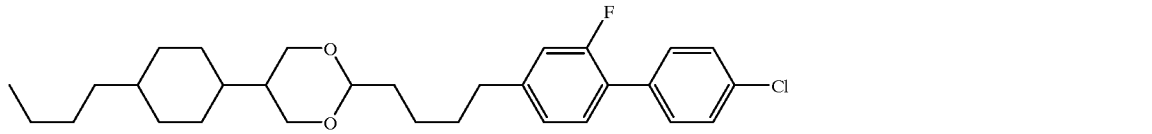

-continued
No. 298
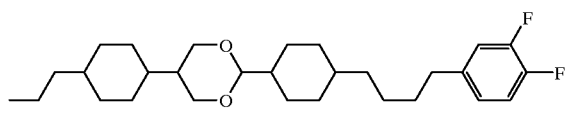
No. 299
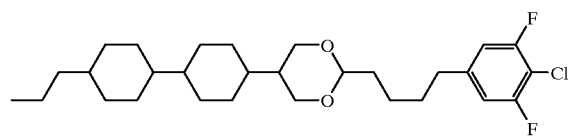
No. 300
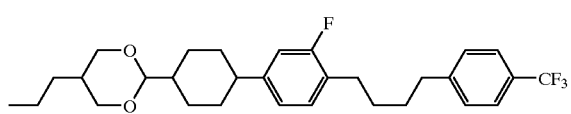
No. 301
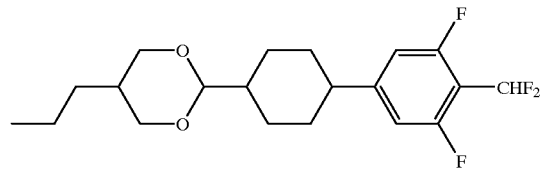
No. 302
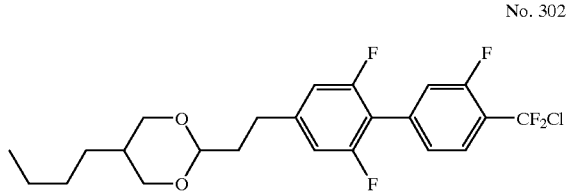
No. 303
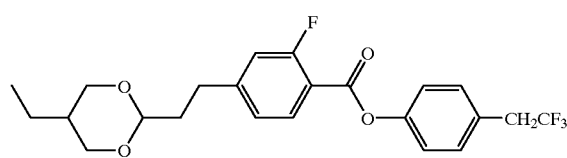
No. 304
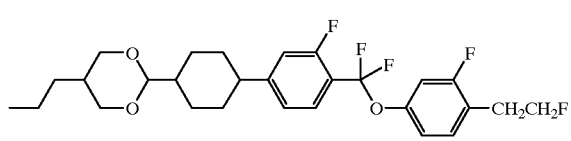
No. 305
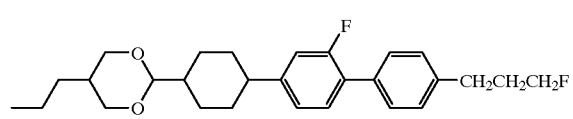
No. 306
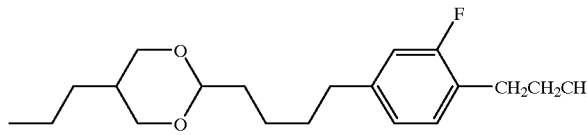
No. 307
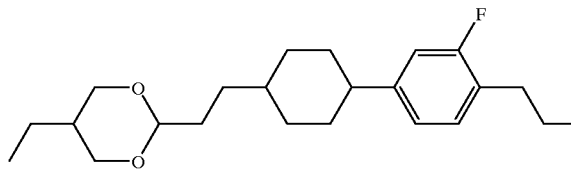
No. 308
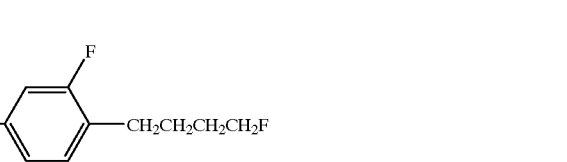
No. 309
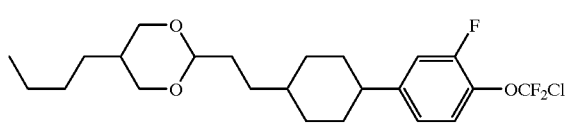
No. 310
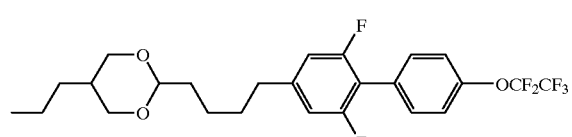
No. 311
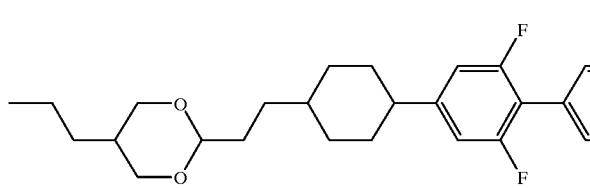
No. 312
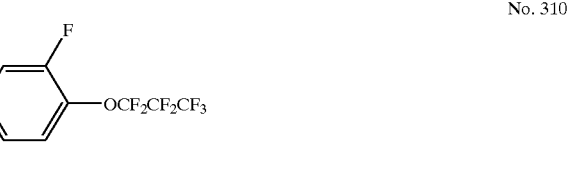

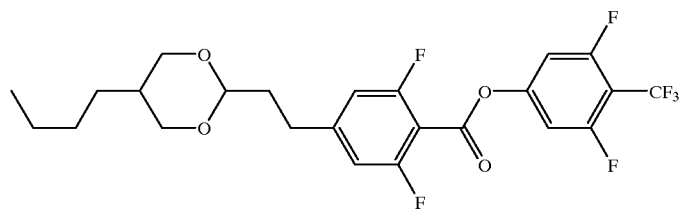
No. 313
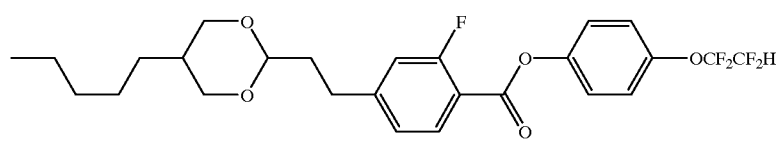
No. 314
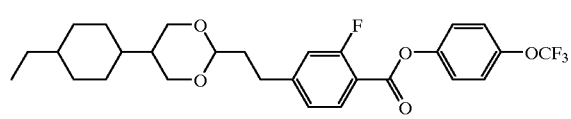
No. 315
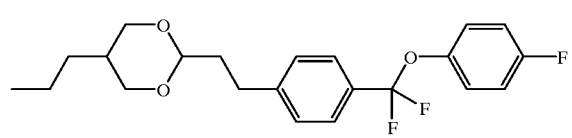
No. 316
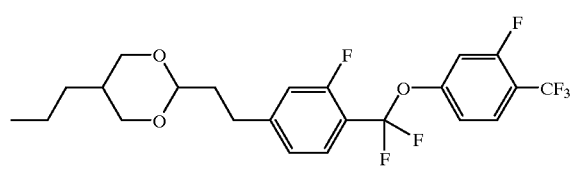
No. 317
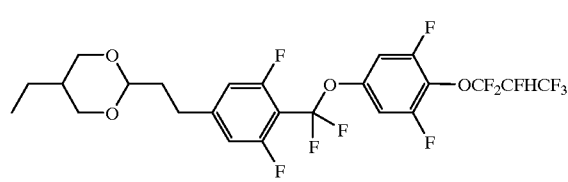
No. 318
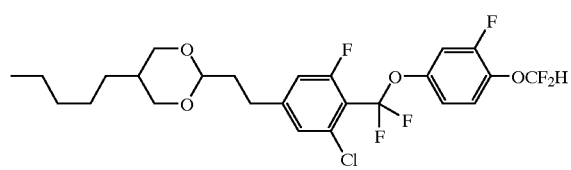
No. 319
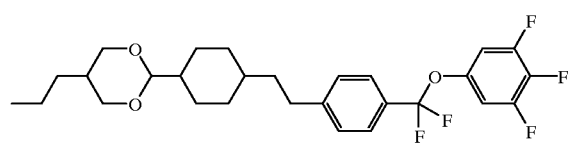
No. 320
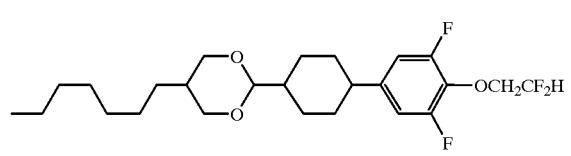
No. 321
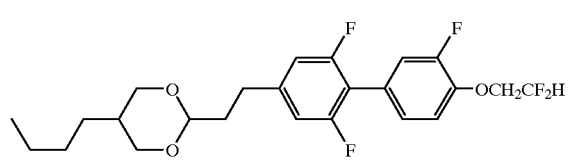
No. 322
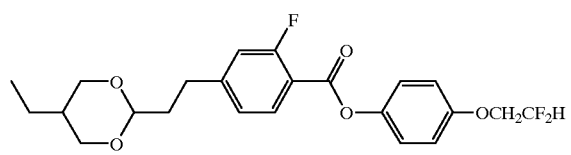
No. 323
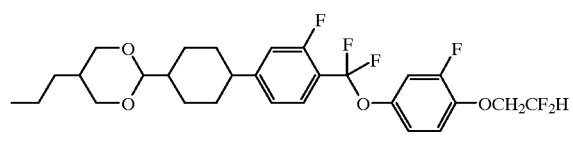
No. 324
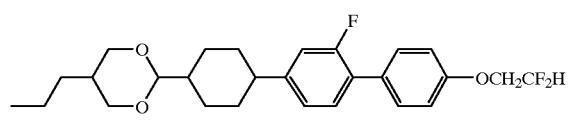
No. 325
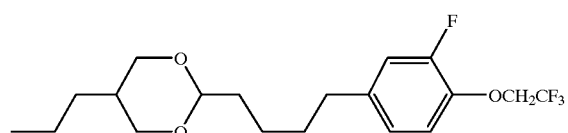
No. 326

No. 327
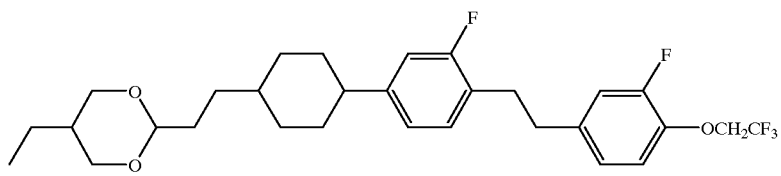
No. 328
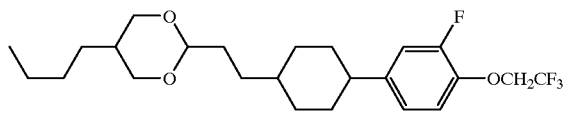
No. 329
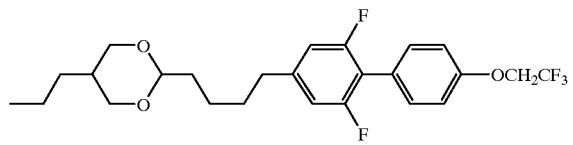
No. 330
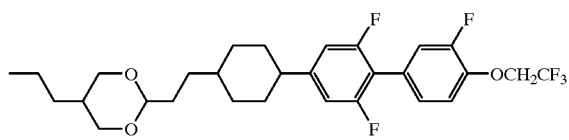
No. 331
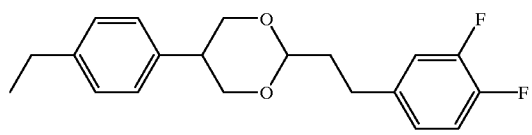
No. 332
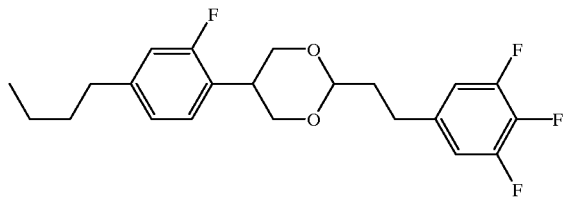
No. 333
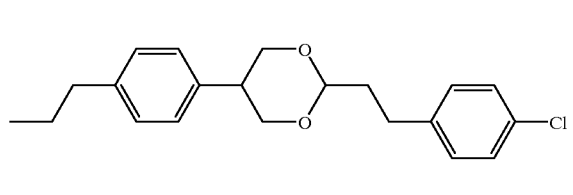
No. 334
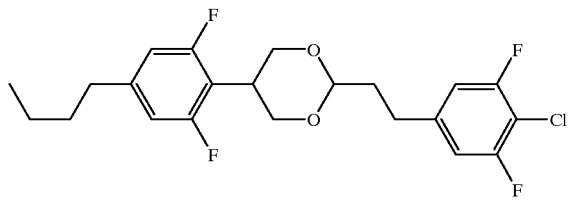
No. 335
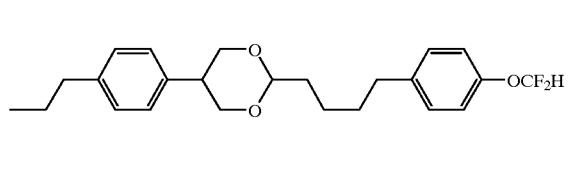
No. 336
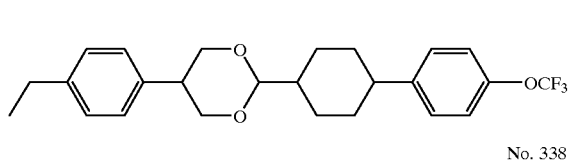
No. 337
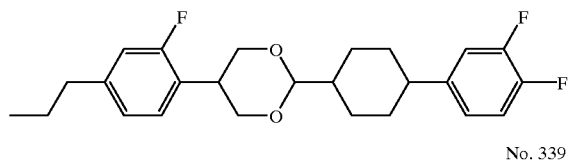
No. 338
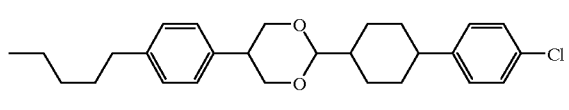
No. 339
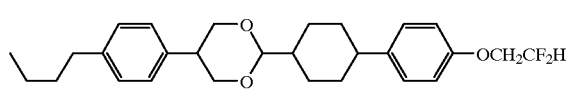
No. 340
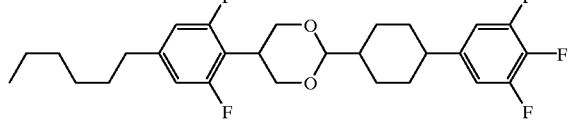
No. 341
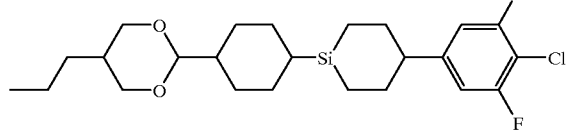

-continued
No. 342
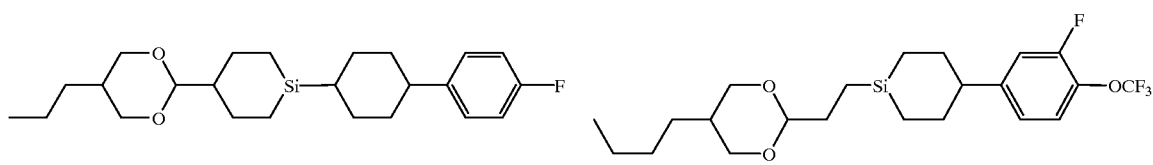
No. 343
No. 344
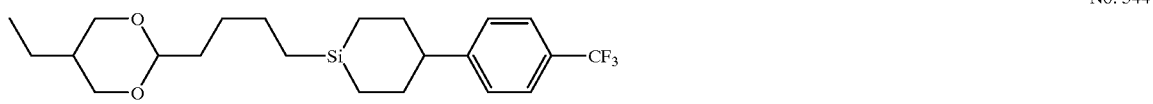
No. 345
No. 346
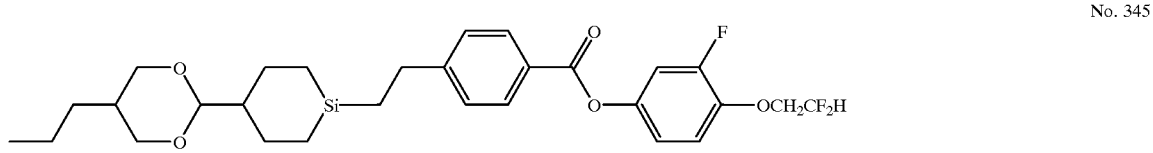
No. 347
No. 348
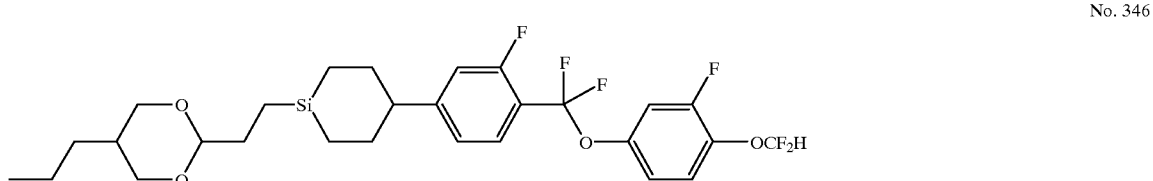
No. 349
No. 350
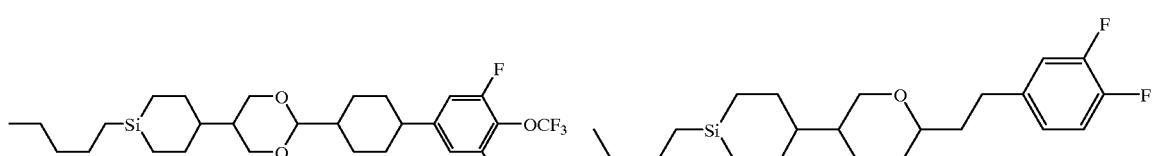
No. 351
No. 352
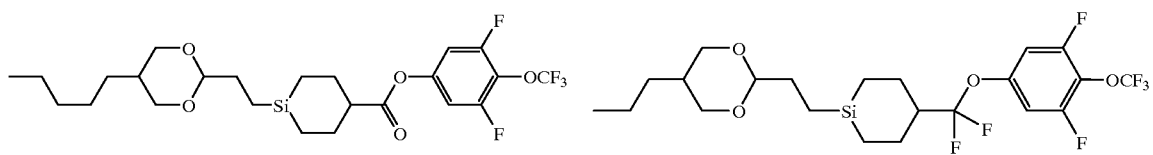
No. 353
No. 354
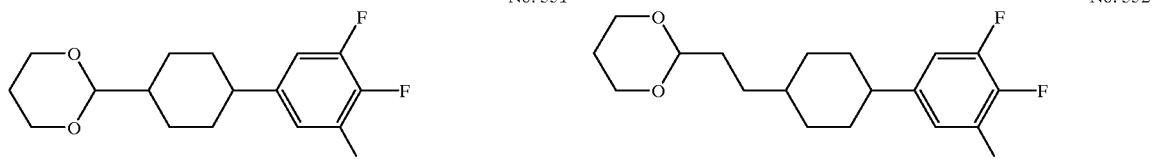
No. 355
No. 356
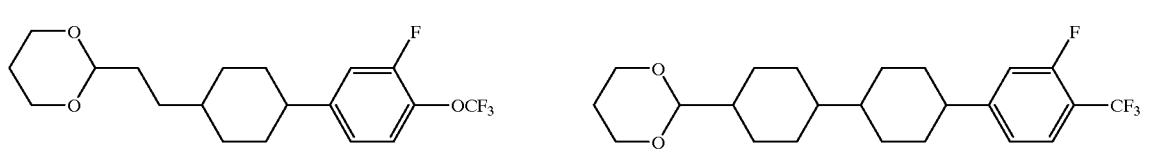
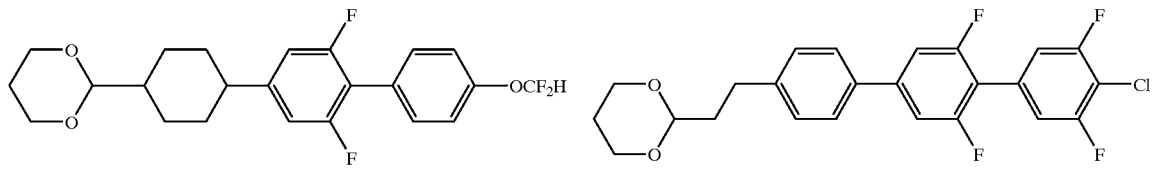

-continued

No. 357
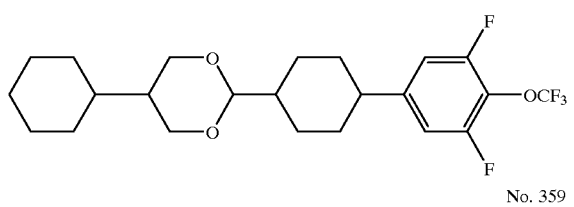

No. 358
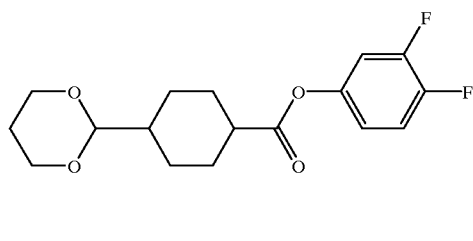

No. 359
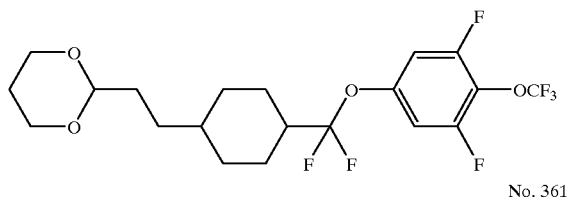

No. 360
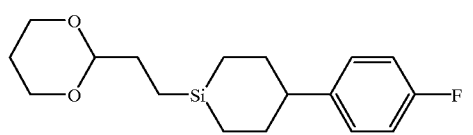

No. 361
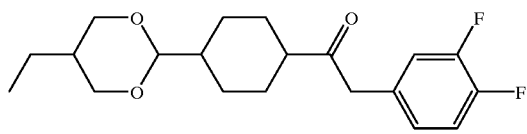

No. 362
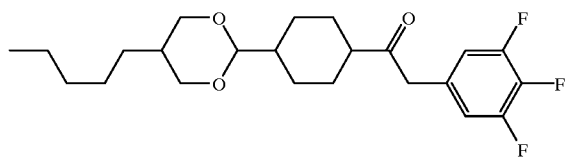

No. 363
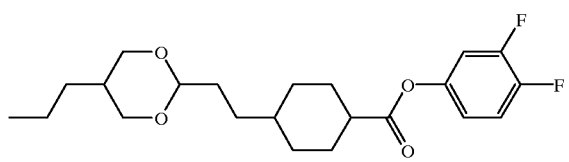

No. 364
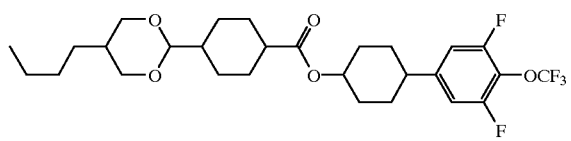

No. 365
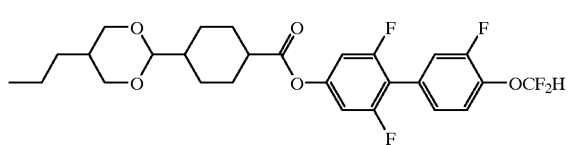

No. 366
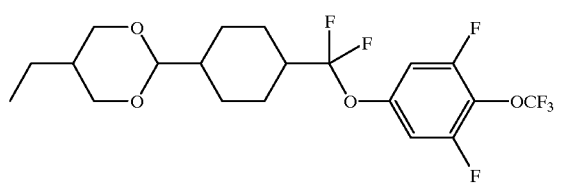

No. 367
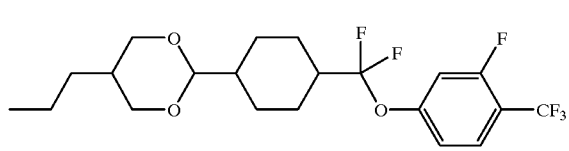

No. 368
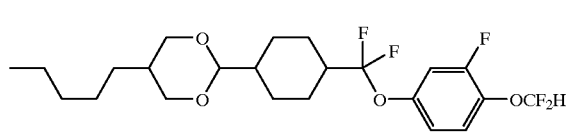

No. 369
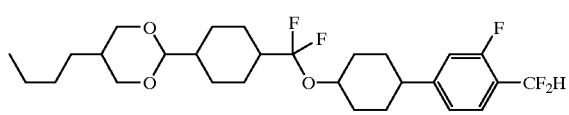

No. 370

EXAMPLE 10 (Using Example 1)

| | |
|---|---|
| 4-(4-propylcyclohexyl)benzonitrile | 24% |
| 4-(4-pentylcyclohexyl)benzonitrile | 36% |
| 4-(4-heptylcyclohexyl)benzonitrile | 25% |
| 4-(4-(4-pentylcyclohexyl)phenylbenzonitrile | 15% |

A liquid crystal composition (A1) was prepared from the said four compounds. % is represented by weight, hereinafter. The clearing point of the nematic liquid crystal composition is 71.7° C., the threshold voltage is 1.79 V at a cell thickness of 9.2 μm, Δε1 is 11.0, Δn is 0.137, and the viscosity is 26.6 mPa.s at 20° C.

A liquid crystal composition (B1) is prepared from 85% of the above liquid crystal composition and 15% of 5-propyl-2-(4-(3,4,5-trifluorophenyl)-cyclohexyl)-1,3-dioxane (Compound No. 21) obtained from Example 1. The clearing point of the composition is 65.3° C., the threshold voltage is 1.46 V at a cell thickness of 9.2 μm, Δε1 is 12.9, Δn is 0.126, and the viscosity is 32.3 mPa.s at 20° C. The properties of the compound No. 21 are calculated by extrapolation from the mixing ratio of the above compositions: clearing point is 29.0° C., $\Delta\epsilon 1$ is 23.7, $\Delta n$ is 0.064, and the viscosity is 64.6 mPa.s at 20° C.

EXAMPLE 11 (Comparing Example 1)

A liquid crystal composition (B1-R) is prepared from 85% of the above liquid crystal composition (A1) and 15% of 5-(4-propylcyclohexyl)-2-(3,4,5-trifluorophenyl)-1,3-dioxane (Compound of formula (14)). The clearing point of the composition is 69.6° C., the threshold voltage is 1.60 V at a cell thickness of 9.2 μm, $\Delta\epsilon 1$ is 11.7, $\Delta n$ is 0.127, and the viscosity is 29.2 mPa.s at 20° C. The properties of the compound of formula (14) are calculated by extrapolation from the mixing ratio of the above compositions: clearing point is 57.7° C., $\Delta\epsilon 1$ is 15.7, $\Delta n$ is 0.070, and the viscosity is 43.9 mPa.s at 20° C.

From the result, comparing with the dioxane ring and the cyclohexane ring of the compound of formula (14), those of the compound (No. 21) of the present invention are reversed. Accordingly, in comparison with the compound of formula (14), the compound No. 21 of the present invention shows, in spite of lower clearing point of 29° C., the $\Delta\epsilon$ is increased to about 1.5 times.

EXAMPLE 12 (Using Example 2)

A liquid crystal composition (B2) is prepared from 85% of the above liquid crystal composition (A1) and 15% of 5-propyl-2-(2-(4-(3-fluoro-4-trifluoromethoxyphenyl)-3,5-difluorophenyl)ethyl)-1,3-dioxane (Compound No. 98) obtained from example 2. The clearing point of the composition is 652.8° C., the threshold voltage is 1.40 V at a cell thickness of 9.3 μm, $\Delta\epsilon 1$ is 13.6, $\Delta n$ is 0.132, and the viscosity is 33.8 mPa.s at 20° C. The properties of the compound No. 98 are calculated by extrapolation from the mixing ratio of the above compositions: clearing point is 12.0° C., $\Delta\epsilon$ is 28.3, $\Delta n$ is 0.104, and the viscosity is 74.6 mPa.s at 20° C.

EXAMPLE 13 (Comparing Example 2)

A liquid crystal composition (B2-R) is prepared from 85% of the above liquid crystal composition (A1) and 15% of 5-propyl-2-(4-(3-fluoro-4trifluoromethoxyphenyl)-3,5-difluorophenyl)-1,3-dioxane (Compound of formula (17)). The clearing point of the composition is 65.1° C., the threshold voltage is 1.40 V at a cell thickness of 9.1 μm, $\Delta\epsilon 1$ is 13.2, $\Delta n$ is 0.133, and the viscosity is 30.8 mPa.s at 20° C. The properties of the compound of formula (17) are calculated by extrapolation from the mixing ratio of the above compositions: clearing point is 27.7° C., $\Delta\epsilon$ is 25.7, $\Delta n$ is 0.110, and the viscosity is 54.6 mPa.s at 20° C.

From the result, comparing with the compound of formula (17), the compound No. 98 of the present invention has an ethylene group at 2-position on the dioxane ring of the compound of formula (17), and the $\Delta\epsilon$ is increased in about 3.3.

EXAMPLE 14 (Using Example 3)

A liquid crystal composition (B3) is prepared from 85% of the above liquid crystal composition (A1) and 15% of 5-propyl-2-(4-(3-fluoro-4-trifluoromethoxy phenyl)-cyclohexyl-1,3-dioxane (Compound No. 22) obtained from Example 3. The clearing point of the composition is 69.2° C., the threshold voltage is 1.56 V at a cell thickness of 9.3 μm, $\Delta\epsilon 1$ is 12.2, $\Delta n$ is 0.128, and the viscosity is 30.0 mPa.s at 20° C. The properties of the compound No. 22 are calculated by extrapolation from the mixing ratio of the above compositions: clearing point is 55.0° C., $\Delta\epsilon 1$ is 19.0, $\Delta n$ is 0.077, and the viscosity is 49.3 mPa.s at 20° C.

EXAMPLE 15 (Using Example 4)

A liquid crystal composition (B4) is prepared from 85% of the above liquid crystal composition (A1) and 15% of 5-propyl-2-(2-(4-trifluoromethylphenyl)ethyl-1,3-dioxane (Compound No. 11) obtained from example 4. The clearing point of the composition is 45.8° C., the threshold voltage is 1.39 V at a cell thickness of 9.1 μm, $\Delta\epsilon 1$ is 11.4, $\Delta n$ is 0.115, and the viscosity is 26.9 mPa.s at 20° C. The properties of the compound No. 11 are calculated by extrapolation from the mixing ratio of the above compositions: clearing point is –101.0° C., $\Delta\epsilon 1$ is 13.7, and the viscosity is 28.5 mPa.s at 20° C.

EXAMPLE 16 (Using Example 5)

A liquid crystal composition (B5) is prepared from 85% of the above liquid crystal composition (A1) and 15% of 5-propyl-4(2-(4-trifluoromethylphenyl)butyl-1,3-dioxane (Compound No. 261) obtained from Example 5. The clearing point of the composition is 45.2° C., the threshold voltage is 1.43 V at a cell thickness of 9.0 μm, $\Delta\epsilon 1$ is 11.2, $\Delta n$ is 0.116, and the viscosity is 27.9 mPa.s at 20° C. The properties of the compound No. 261 are calculated by extrapolation from the mixing ratio of the above compositions: clearing point is –105.0° C., $\Delta\epsilon 1$ is 12.3, and the viscosity is 35.3 mPa.s at 20° C.

EXAMPLE 17 (Using Example 6)

A liquid crystal composition (B6) is prepared from 85% of the above liquid crystal composition (A1) and 15% of 5-propyl-2-(4-(4-(3-fluoro-4-chlorophenyl)-3,5-difluorophenyl)cyclohexyl)-1,3-dioxane (Compound No. 175) obtained from example 6. The clearing point of the composition is 83.0° C., the threshold voltage is 1.70 V at a cell thickness of 8.9 μm, $\Delta\epsilon 1$ is 14.0, $\Delta n$ is 0.142, and the viscosity is 40.5 mPa.s at 20° C. The properties of the compound No. 275 are calculated by extrapolation from the mixing ratio of the above compositions: clearing point is 147.0° C., $\Delta\epsilon$ is 31.0 $\Delta n$ is 0.170, and the viscosity is 119.1 mPa.s at 20° C.

EXAMPLE 18 (Using Example 7)

A liquid crystal composition (B7) is prepared from 85% of the above liquid crystal composition (A1) and 15% of 4-(5-pentyl-1,3-dioxane-2-yl) cyclohexanecarboxylic acid 3,4,5-trifluorophenylester (Compound No. 362) obtained from Example 7. The clearing point of the composition is 70.3° C., the threshold voltage is 1.49 V at a cell thickness of 8.9 μm, $\Delta\epsilon 1$ is 12.2, $\Delta n$ is 0.126, and the viscosity is 32.3 mPa.s at 20° C. The properties of the compound No. 362 are calculated by extrapolation from the mixing ratio of the above compositions: clearing point is 62.4° C., $\Delta\epsilon$ is 19.0, $\Delta n$ is 0.064, and the viscosity is 64.9 mPa.s at 20° C.

EXAMPLE 19 (Using Example 8)

A liquid crystal composition (B8) is prepared from 85% of the above liquid crystal composition (A1) and 15% of 1-(2-(1,3-dioxane-2-yl)ethyl) cyclohexyl-3,4,5-trifluorobenzene (Compound No. 352) obtained from Example 8. The clearing point of the composition is 50.0° C., the threshold voltage is 1.40 V at a cell thickness of 8.9

μm, Δε1 is 12.8, Δn is 0.114, and the viscosity is 37.6 mPa.s at 20° C. The properties of the compound No. 352 are calculated by extrapolation from the mixing ratio of the above compositions: clearing point is −73.0° C., Δε is 23.0, and the viscosity is 100.2 mPa.s at 20° C.

EXAMPLE 20 (Using Example 9)

A liquid crystal composition (B9) is prepared from 85% of the above liquid crystal composition (A1) and 15% of 1-(2-(5-propyl-1,3-dioxane-2-yl)ethyl) cyclohexyl-3,4,5-trifluorobenzene (Compound No. 33) obtained from Example 9. The clearing point of the composition is 65.7° C., the threshold voltage is 1.57 V at a cell thickness of 9.0 μm, Δε1 is 12.2, Δn is 0.124, and the viscosity is 34.2 mPa.s at 20° C. The properties of the compound No. 33 are calculated by extrapolation from the mixing ratio of the above compositions: clearing point is 31.7° C., Δε is 19.0, Δn is 0.050, and the viscosity is 77.0 mPa.s at 20° C.

Industrial Applicability

The compounds of the present invention are characterized by a high voltage holding ratio and large Δε, by using the compounds of the present invention as constitutional components of liquid crystal compositions, driving at low voltage can be realized with liquid crystal display device of a TFT mode, which has been impossible hitherto.

What is claimed is:

1. A dioxane derivative represented by general formula (I):

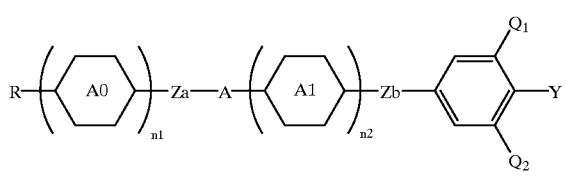

(1)

wherein R represents an alkyl group of 1–20 carbon atoms or a hydrogen atom, n1 and n2, each independently, are an integer of 0–2, n1+n2≦2, $Q_1$ and $Q_2$, each independently, are a hydrogen atom, fluorine atom or chlorine atom, A represents (a), (b) or (c), (a)
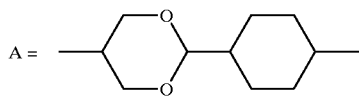

(b)
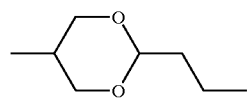

(c)
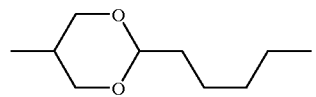

ring A0 and A1 represent a 1,4-cyclohexylene group or a 1,4-phenylene group, in which 1 or more hydrogen atoms may be replaced by a fluorine atom or a chlorine atom, and one or two carbon atoms may be replaced by a silicon atom in the 1,4-cyclohexylene in A, ring A0 and ring A1, Za and Zb, each independently, represent a single bond, —CH$_2$CH$_2$—, —CH$_2$CH$_2$CH$_2$CH$_2$—, OCH$_2$, —CH$_2$O—, COO— or —CF$_2$O—, Y represents a hydrogen atom, a halogen atom, or a halogenated alkyl group of 1–5 carbon atoms, in which one or more not-adjacent methylene groups may be replaced by an oxygen atom or a sulfur group, in the case of n1=0 and n2=1, and A is (b), ring A1 is

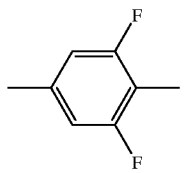

in the case of Y is a fluorine atom or a chlorine atom, Q1 and Q2, each independently, represent a fluorine atom or a chlorine atom; and in the case of A is (a) and Zb is a single bond, n1+n2=1, further, each element constituting the compound may be replaced by its isotope.

2. A dioxane derivative according to claim 1, wherein n1+n2=1, and A=(b).

3. A liquid crystal composition comprising at least one dioxane derivative according to claim 1 as the first component, and at least one compound selected from the group consisting of compounds represented by general formulas (2), (3) and (4) as the second component,

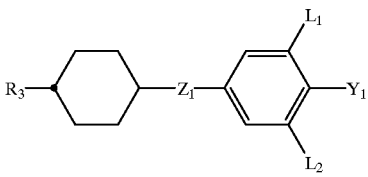

(2)

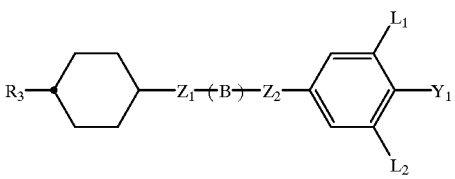

(3)

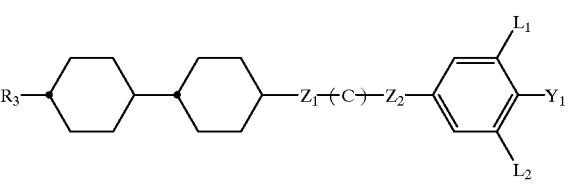

(4)

wherein $R_3$ is an alkyl group of 1–10 carbon atoms, in the alkyl group, at least one not-adjacent methylene group may be replaced by an oxygen atom or —CH=CH—, and any hydrogen atom may be replaced by a fluorine atom, $Y_1$ represents a fluorine atom, a chlorine atom, OCF$_3$, OCF$_2$H, CF$_3$, CF$_2$H, CFH$_2$, OCF$_2$CF$_2$H or OCF$_2$CFHCF$_3$, $L_1$ and $L_2$, each independently, represent a hydrogen atom or a fluorine atom, $Z_1$ and $Z_2$, each independently, —CH$_2$CH$_2$—, —CH$_2$CH$_2$CH$_2$CH$_2$—, —COO—, —CF$_2$O—, —OCF$_2$—, —CH=CH— or a single bond, ring B represents trans-1,4-cyclohexylene, 1,3-dioxane-2,5-diyl or 1,4-phenylene, wherein the hydrogen atom may be replaced by a fluorine atom, ring C represents trans-1,4-cyclohexylene or 1,4-phenylene, wherein the hydrogen atom may be replaced by a fluorine atom, and each element constituting the compound in each formula may be replaced by its isotope.

4. A liquid crystal composition comprising at least one dioxane derivative according to claim 1 as the first component, and at least one compound selected from the group consisting of compounds represented by general formulas (5) and (6) as the second component,

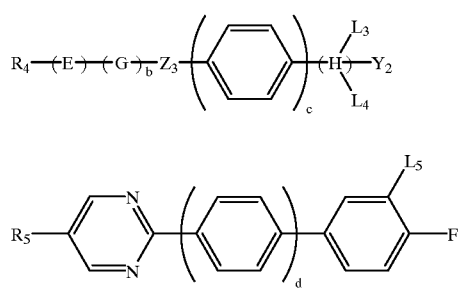

(5)

(6)

wherein $R_4$ and $R_5$, each independently, represent an alkyl group of 1–10 carbon atoms, in the alkyl group, one or more not-adjacent methylene groups may be replaced by an oxygen atom or —CH=CH—, and any hydrogen atom may be replaced by a fluorine atom, $Y_2$ represents —CN or —C≡C—CN, ring E represents trans-1,4-cyclohexylene, 1,4-phenylene, 1,3-dioxane-2,5-diyl or pyrimidine-2,5-diyl, ring G represents trans-1,4-cyclohexylene, pyrimidine-2,5-diyl, or 1,4-phenylene, wherein the hydrogen atom may be replaced by a fluorine atom, ring H represents trans-1,4-cyclohexylene or 1,4-phenylene, $Z_3$ represents —CH$_2$CH$_2$—, —COO— or a single bond, $L_3$, $L_4$ and $L_5$, each independently, represent a hydrogen atom or a fluorine atom, b, c and d, each independently, are 0 or 1, and each element constituting the compound in each formula may be replaced by its isotope.

5. A liquid crystal composition comprising at least one dioxane derivative according to claim 1 as the first component, and at least one compound selected from the group consisting of compounds represented by the said general formulas (2), (3) and (4) as the second component, and at least one compound selected from the group consisting of compounds represented by general formulas (7), (8) and (9) as the third component,

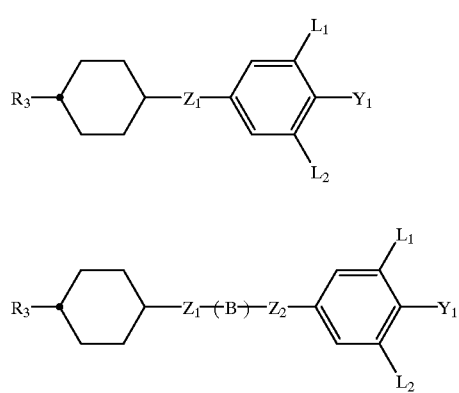

(2)

(3)

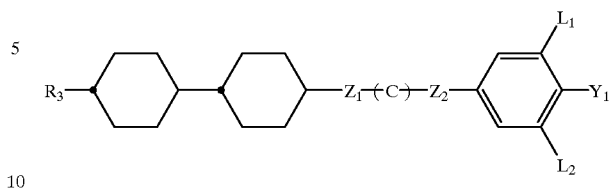

(4)

wherein $R_3$ is an alkyl group of 1–10 carbon atoms, in the alkyl group, at least one not-adjacent methylene group may be replaced by an oxygen atom or —CH=CH—, and any hydrogen atom may be replaced by a fluorine atom, $Y_1$ represents a fluorine atom, a chlorine atom, OCF$_3$, OCF$_2$H, CF$_3$, CF$_2$H, CFH$_2$, OCF$_2$CF$_2$H or OCF$_2$CFHCF$_3$, $L_1$ and $L_2$, each independently, represent a hydrogen atom or a fluorine atom, $Z_1$ and $Z_2$, each independently, represent —CH$_2$CH$_2$—, —CH$_2$CH$_2$CH$_2$CH$_2$—, —COO—, —CF$_2$O—, —OCF$_2$—, —CH=CH— or a single bond, ring B represents trans-1,4-cyclohexylene, 1,3-dioxane2,5diyl or 1,4-phenylene, wherein the hydrogen atom may be replaced by a fluorine atom, ring C represents trans-1,4-cyclohexylene or 1,4phenylene, wherein the hydrogen atom may be replaced by a fluorine atom, and each element constituting the compound in each formula may be replaced by its isotope,

(7)

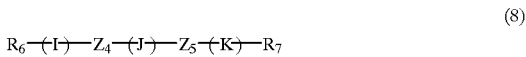

(8)

(9)

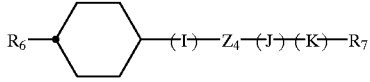

wherein $R_6$ and $R_7$, each independently, represent an alkyl group of 1–10 carbon atoms, in the alkyl group, one or more not-adjacent methylene groups may be replaced by an oxygen atom or —CH=CH—, and any hydrogen atom may be replaced by a fluorine atom, I, J and K, each independently, represent trans-1,4-cyclohexylene, pyrimidine-2,5-diyl or 1,4phenylene, wherein the hydrogen atom may be replaced by a fluorine atom, $Z_4$ and $Z_5$, each independently, represent —CH≡C—, —COO—, —CH$_2$CH$_2$—, —CH=CH— or a single bond, and each element constituting the compound in each formula may be replaced by its isotope.

6. A liquid crystal composition comprising at least one dioxane derivative according to claim 1 as the first component, and at least one compound selected from the group consisting of compounds represented by the said general formulas (5) and (6) as the second component, and at least one compound selected from the group consisting of compounds represented by the said general formulas (7), (8) and (9) as the third component,

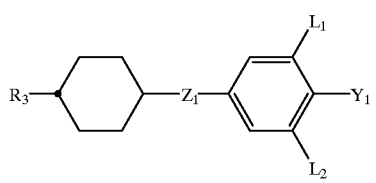

(2)

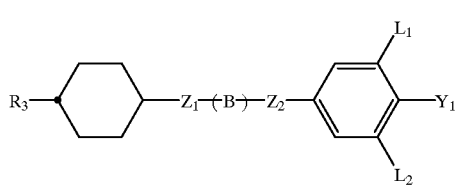

(3)

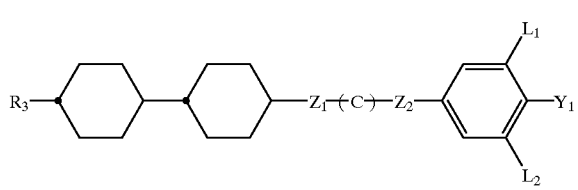

(4)

wherein R₃ is an alkyl group of 1–10 carbon atoms, in the alkyl group, at least one not-adjacent methylene group may be replaced by an oxygen atom or —CH=CH—, and any hydrogen atom may be replaced by a fluorine atom, Y₁ represents a fluorine atom, a chlorine atom, OCF₃, OCF₂H, CF₃, CF₂H, CFH₂, OCF₂CF₂H or OCF₂CFHCF₃, L₁ and L₂ each independently, represent a hydrogen atom or a fluorine atom, Z₁ and Z₂, each independently, represent —CH₂CH₂—, —CH₂CH₂CH₂CH₂—, —COO—, —CF₂O—, —OCF₂—, —CH=CH— or a single bond, ring B represents trans-1,4-cyclohexylene, 1,3-dioxane-2,5diyl or 1,4-phenylene, wherein the hydrogen atom may be replaced by a fluorine atom, ring C represents trans-1,4-cyclohexylene or 1,4-phenylene, wherein the hydrogen atom may be replaced by a fluorine atom, and each element constituting the compound in each formula may be replaced by its isotope,

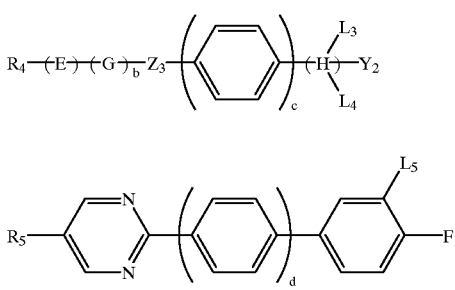

(5)

(6)

wherein R₄ and R₅, each independently, represent an alkyl group of 1–10 carbon atoms, in the alkyl group, one or more not-adjacent methylene groups may be replaced by an oxygen atom or —CH=CH—, and any hydrogen atom maybe replaced by a fluorine atom, Y₂ represents —CN or —C≡C—CN, ring E represents trans-1,4cyclohexylene, 1,4-phenylene, 1,3-dioxane2,5-diyl or pyrimidine-2,5diyl, ring G represents trans-1,4-cyclohexylene, pyrimidine-2,5-diyl, or 1,4-phenylene, wherein the hydrogen atom may be replaced by a fluorine atom, ring H represents trans-1,4cyclohexylene or 1,4-phenylene, Z₃ represents —CH₂CH₂—, —COO— or a single bond, L₃, L₄ and L₅, each independently, represent a hydrogen atom or a fluorine atom, b, c and d, each independently, are 0 or 1, and each element constituting the compound in each formula may be replaced by its isotope,

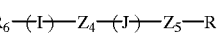

(7)

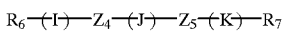

(8)

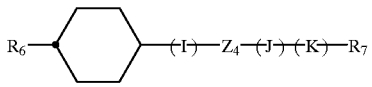

(9)

wherein R₆ and R₇, each independently, represent an alkyl group of 1–10 carbon atoms, in the alkyl group, one or more not-adjacent methylene groups may be replaced by an oxygen atom or —CH=CH—, and any hydrogen atom may be replaced by a fluorine atom, I, J and K, each independently, represent trans-1,4-cyclohexylene, pyrimidine-2,5diyl or 1,4-phenylene, wherein the hydrogen atom may be replaced by a fluorine atom, Z₄ and Z₅, each independently, represent —C≡C—, —COO—, —CH₂CH₂—, —CH=CH— or a single bond, and each element constituting the compound in each formula may be replaced by its isotope.

7. A liquid crystal composition comprising at least one dioxane derivative according to claim 1 as the first component, and at least one compound selected from the group consisting of compounds represented by the said general formulas (2), (3) and (4) as a part of the second component, and at least one compound selected from the group consisting of compounds represented by the said general formulas (5) and (6) as another part of the second component, and at least one compound selected from the group consisting of compounds represented by the said general formulas (7), (8) and (9) as the third component,

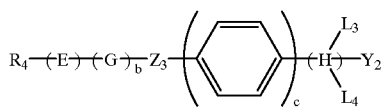

(5)

(6)

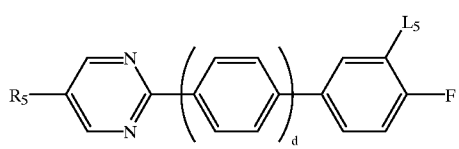

wherein R₄ and R₅, each independently, represent an alkyl group of 1–10 carbon atoms, in the alkyl group, one or more not-adjacent methylene groups may be replaced by an oxygen atom or —CH=CH—, and any hydrogen atom may be replaced by a fluorine atom, Y₂ represents —CN or —C≡C—CN, ring E represents trans-1,4-cyclohexylene, 1,4-phenylene, 1,3-dioxane-2,5-diyl or pyrimidine-2,5-diyl, ring G represents trans-1,4-cyclohexylene, pyrimidine-2,5-diyl, or 1,4-phenylene, wherein the hydrogen atom may be replaced by a fluorine atom, ring H represents trans-1,4-cyclohexylene or 1,4-phenylene, $Z_3$ represents —$CH_2CH_2$—, —COO— or a single bond, $L_3$, $L_4$ and $L_5$, each independently, represent a hydrogen atom or a fluorine atom, b, c and d, each independently, are 0 or 1, and each element constituting the compound in each formula may be replaced by its isotope,

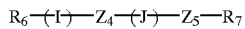
(7)

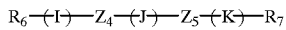
(8)

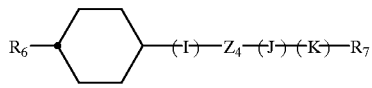
(9)

wherein $R_6$ and $R_7$, each independently, represent an alkyl group of 1–10 carbon atoms, in the alkyl group, one or more not-adjacent methylene groups may be replaced by an oxygen atom or —CH=CH—, and any hydrogen atom may be replaced by a fluorine atom, I, J and K, each independently, represent trans-1,4-cyclohexylene, pyrimidine-2,5-diyl or 1,4-phenylene, wherein the hydrogen atom maybe replaced by a fluorine atom, $Z_4$ and $Z_5$, each independently, represent —C≡C—, —COO—, —$CH_2CH_2$—, —CH=CH— or a single bond, and each element constituting the compound in each formula may be replaced by its isotope.

8. A liquid crystal composition according to claim 9 wherein the liquid crystal composition further contains an optically active compound.

9. A liquid crystal device comprising a liquid crystal composition according to claim 4.

10. A liquid crystal display device comprising the liquid crystal composition according to claim 8.

11. A liquid crystal composition comprising at least two components, at least one of which is a dioxane derivative according to claim 1.

12. A dioxane derivative represented by general formula (I):

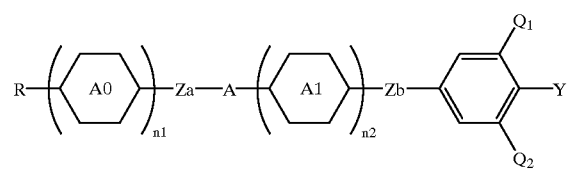
(1)

wherein R represents an alkyl group of 1–20 carbon atoms or a hydrogen atom, n1 and n2 are each zero, $Q_1$ and $Q_2$, each independently, are a hydrogen atom, fluorine atom or chlorine atom,

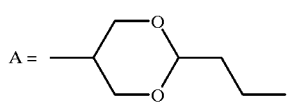
(b)

Za is a single bond and Zb represents a single bond, —$CH_2CH_2$—, —$CH_2CH_2CH_2CH_2$—, $OCH_2$, —$CH_2O$—, COO— or —$CF_2O$—, Y represents a hydrogen atom, a halogen atom, or a halogenated alkyl group of 1–5 carbon atoms, in which one or more not-adjacent methylene groups may be replaced by an oxygen atom or a sulfur group, in the case of Y is a fluorine atom or a chlorine atom, Q1 and Q2, each independently, represent a fluorine atom or a chlorine atom, further, each element constituting the compound may be replaced by its isotope.

13. A dioxane derivative represented by general formula (I):

(1)

wherein R represents an alkyl group of 1–20 carbon atoms or a hydrogen atom, n1 and n2, each independently, are an integer of 0–2, n1+n2=2, $Q_1$ and $Q_2$, each independently, are a hydrogen atom, fluorine atom or chlorine atom,

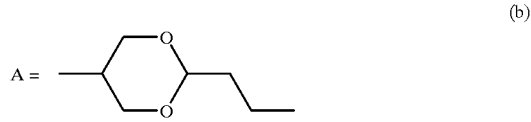
(b)

ring A0 and A1 represent a 1,4-cyclohexylene group or a 1,4-phenylene group, in which 1 or more hydrogen atoms may be replaced by a fluorine atom or a chlorine atom, and one or two carbon atoms may be replaced by a silicon atom in the 1,4-cyclohexylene in, ring A0 and ring A1, Za and Zb, each independently, represent a single bond, —$CH_2CH_2$—, —$CH_2CH_2CH_2CH_2$—, $OCH_2$, —$CH_2O$—, COO— or —$CF_2O$—, Y represents a hydrogen atom, a halogen atom, or a halogenated alkyl group of 1–5 carbon atoms, in which one or more not-adjacent methylene groups may be replaced by an oxygen atom or a sulfur group, in the case of Y is a fluorine atom or a chlorine atom, Q1 and Q2, each independently, represent a fluorine atom or a chlorine atom, further, each element constituting the compound may be replaced by its isotope.

14. A dioxane derivative represented by general formula (I):

(1)

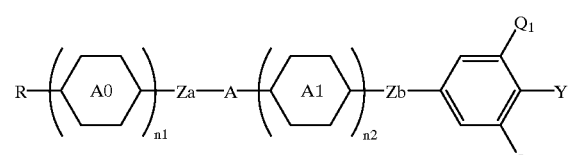

wherein R represents an alkyl group of 1–20 carbon atoms or a hydrogen atom, n1 and n2 are each zero, $Q_1$ and $Q_2$, each independently, are a hydrogen atom, fluorine atom or chlorine atom, (a)

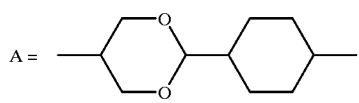

and one or two carbon atoms may be replaced by a silicon atom in the 1,4-cyclohexylene in A, Za is a single bond and Zb represents a single bond, —$CH_2CH_2$—, —$CH_2CH_2CH_2CH_2$—, $OCH_2$, —$CH_2O$—, $COO$— or —$CF_2O$—, Y represents a hydrogen atom, a halogen atom, or a halogenated alkyl group of 1–5 carbon atoms, in which one or more not-adjacent methylene groups may be replaced by an oxygen atom or a sulfur group, in the case of Zb is a single bond, at least one of Q1 and Q2 represents a fluorine atom or a chlorine atom; and in the case of Y is a fluorine atom or a chlorine atom, $Q_1$ and $Q_2$, each independently, represent a fluorine atom or a chlorine atom, further, each element constituting the compound may be replaced by its isotope.

15. A dioxane derivative represented by general formula (I):

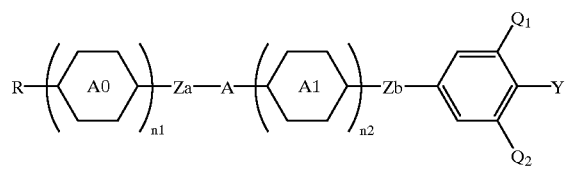

(1)

wherein R represents an alkyl group of 1–20 carbon atoms or a hydrogen atom, n1 and n2, each independently, are an integer of 0–2, n1+n2≦2, Q1 and Q2, each independently, are a hydrogen atom, fluorine atom or chlorine atom, A represents (a), (b) or (c),

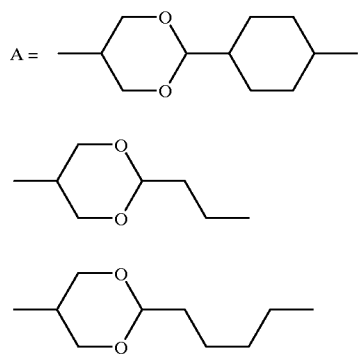

ring A0 and A1 represent a 1,4-cyclohexylene group or a 1,4-phenylene group, in which 1 or more hydrogen atoms may be replaced by a fluorine atom or a chlorine atom, and one or two carbon atoms may be replaced by a silicon atom in the 1,4-cyclohexylene in (a), ring A0 and ring A1, Za and Zb, each independently, represent a single bond, —$CH_2CH_2$—, —$CH_2CH_2CH_2CH_2$—, $OCH_2$, —$CH_2O$—, $COO$— or —$CF_2O$—, Y represents a hydrogen atom, a halogen atom, or a halogenated alkyl group of 1–5 carbon atoms, in which one or more not-adjacent methylene groups may be replaced by an oxygen atom or a sulfur group, in the case of n1=0 and n2=1, and A is (b), and ring A1 is 1,4-phenylene, and Za and Zb are a single bond, at least one of Q1 and Q2 represents a fluorine atom or a chlorine atom; in the case of Y is a fluorine atom or a chlorine atom, Q1 and Q2, each independently, represent a fluorine atom or a chlorine atom; and in the case of A is (c), or Zb is —$CH_2CH_2CH_2CH_2$—, or n1 is not 0, Za is —$CH_2CH_2CH_2CH_2$—, and in the case of A is (a) and Zb is a single bond, n1+n2=1 further, each element constituting the compound may be replaced by its isotope.

16. A dioxane derivative represented by general formula (I):

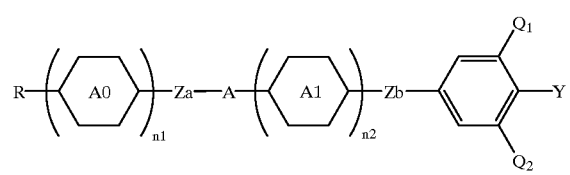

(1)

wherein R represents an alkyl group of 1–20 carbon atoms or a hydrogen atom, n1 and n2, each independently, are an integer of 0–2, n1+n2≦2, $Q_1$ and $Q_2$ both are a fluorine atom, A represents (a), (b) or (c),

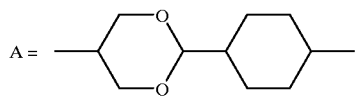

(a)

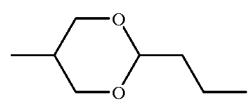

(b)

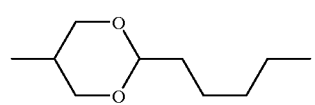

(c)

ring A0 and A1 represent a 1,4-cyclohexylene group or a 1,4-phenylene group, in which 1 or more hydrogen atoms may be replaced by a fluorine atom or a chlorine atom, and one or two carbon atoms may be replaced by a silicon atom in the 1,4-cyclohexylene in (a), ring A0 and ring A1, Za and Zb, each independently, represent a single bond, —$CH_2CH_2$—, —$CH_2CH_2CH_2CH_2$—, $OCH_2$, —$CH_2O$—, $COO$— or —$CF_2O$—, Y represents a hydrogen atom, a halogen atom, or a halogenated alkyl group of 1–5 carbon atoms, in which one or more not-adjacent methylene groups may be replaced by an oxygen atom or a sulfur group, and in the case of A is (a) and Zb is a single bond, n1+n2=1, further, each element constituting the compound may be replaced by its isotope.

17. A liquid crystal composition comprising at least two components, at least one of which is a dioxane derivative according to claim 12.

18. A liquid crystal composition comprising at least two components, at least one of which is a dioxane derivative according to claim 13.

19. A liquid crystal composition comprising at least two components, at least one of which is a dioxane derivative according to claim 14.

20. A liquid crystal composition comprising at least two components, at least one of which is a dioxane derivative according to claim 15.

21. A liquid crystal composition comprising at least two components, at least one of which is a dioxane derivative according to claim 16.

\* \* \* \* \*